US012029761B2

(12) United States Patent
Zhu et al.

(10) Patent No.: US 12,029,761 B2
(45) **Date of Patent: *Jul. 9, 2024**

(54) GUIDANCE AND NAVIGATION CONTROL PROTEINS AND METHOD OF MAKING AND USING THEREOF

(71) Applicants: SYSTIMMUNE, INC., Redmond, WA (US); SICHUAN BAILI PHARMACEUTICAL CO. LTD., Sichuan (CN)

(72) Inventors: Yi Zhu, Sichuan (CN); Ole Olsen, Everett, WA (US); Dong Xia, Redmond, WA (US); David Jellyman, Duvall, WA (US); Katrina Bykova, Seattle, WA (US); Anne-Marie Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Camilla Wang, Sammamish, WA (US); Zeren Gao, Redmond, WA (US); Hui Huang, Redmond, WA (US)

(73) Assignee: SYSTIMMUNE, INC., Redmond, WA (US)

( * ) Notice: Subject to any disclaimer, the term of this patent is extended or adjusted under 35 U.S.C. 154(b) by 508 days.

This patent is subject to a terminal disclaimer.

(21) Appl. No.: 17/040,513

(22) PCT Filed: Mar. 26, 2019

(86) PCT No.: PCT/US2019/024105

§ 371 (c)(1),
(2) Date: Sep. 22, 2020

(87) PCT Pub. No.: WO2019/191120

PCT Pub. Date: Oct. 3, 2019

(65) Prior Publication Data

US 2021/0024630 A1 Jan. 28, 2021

Related U.S. Application Data

(60) Provisional application No. 62/648,880, filed on Mar. 27, 2018, provisional application No. 62/648,888, filed on Mar. 27, 2018.

(51) Int. Cl.

| | |
|---|---|
| ***A61P 35/00*** | (2006.01) |
| ***A61K 35/17*** | (2015.01) |
| ***A61P 35/02*** | (2006.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| ***C12N 5/09*** | (2010.01) |
| ***G01N 33/574*** | (2006.01) |

(52) U.S. Cl.

CPC .............. *A61K 35/17* (2013.01); *A61P 35/00* (2018.01); *A61P 35/02* (2018.01); *C07K 14/70503* (2013.01); *C07K 14/7051* (2013.01); *C07K 14/70532* (2013.01); *C07K 14/70578* (2013.01); *C07K 16/2803* (2013.01); *C07K 16/2809* (2013.01); *C07K 16/2827* (2013.01); *C07K 16/2863* (2013.01); *C07K 16/2878* (2013.01); *C12N 5/0638* (2013.01); *C12N 5/0693* (2013.01); *G01N 33/57488* (2013.01); *C07K 2317/24* (2013.01); *C07K 2317/31* (2013.01); *C07K 2317/52* (2013.01); *C07K 2317/524* (2013.01); *C07K 2317/526* (2013.01); *C07K 2317/55* (2013.01); *C07K 2317/622* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 2012/0141484 | A1 | 6/2012 | Garcia-Martinez | |
| 2017/0224818 | A1* | 8/2017 | Lindhofer | C07K 16/2887 |
| 2017/0320959 | A1 | 11/2017 | Swanson et al. | |
| 2020/0157224 | A1* | 5/2020 | Zhu | C07K 16/00 |
| 2022/0002406 | A1* | 1/2022 | Zhu | C07K 16/2878 |

FOREIGN PATENT DOCUMENTS

| | | | | |
|---|---|---|---|---|
| WO | WO2016173605 | A1 | 11/2016 | |
| WO | WO-2017011342 | A1 * | 1/2017 | C07K 16/468 |
| WO | WO-2017180913 | A2 * | 10/2017 | A61K 39/3955 |
| WO | WO-2019005639 | A2 * | 1/2019 | A61P 35/00 |

OTHER PUBLICATIONS

Michaelson et al, mAbs 1:2, 128-141; Mar./Apr. 2009. (Year: 2009).*

* cited by examiner

*Primary Examiner* — Meera Natarajan
*Assistant Examiner* — Cheom-Gil Cheong
(74) *Attorney, Agent, or Firm* — Feng Wan

(57) ABSTRACT

The application provides guidance and navigation control (GNC) proteins. In one embodiment, the guidance and navigation control (GNC) protein, comprising a binding domain for a T cell activating receptor, a binding domain for a tumor associated antigen, a bind domain for an immune checkpoint receptor, and a binding domain for a T cell co-stimulating receptor. The binding domain for the tumor associated antigen is not adjacent to the binding domain for the T cell co-stimulating receptor. In one embodiment, the binding domain for the T cell activating receptor is adjacent to the binding domain for the tumor associated antigen (TAA).

21 Claims, 24 Drawing Sheets

Specification includes a Sequence Listing.

FIGURE 1. GNC proteins are characterized by their composition of multiple antigen binding domains (AgBD) and linkers.
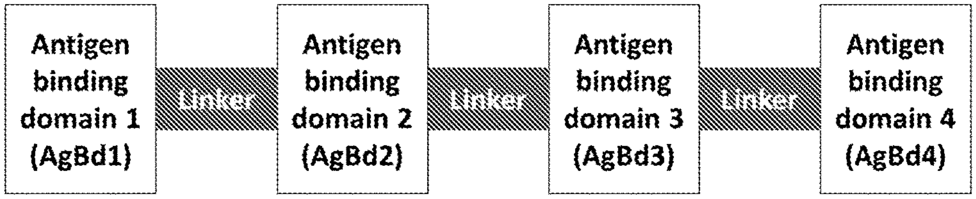

FIGURE 2A. General format of a tetra-specific GNC antibody with an EGFRvIII AgBD (SI-39E18).
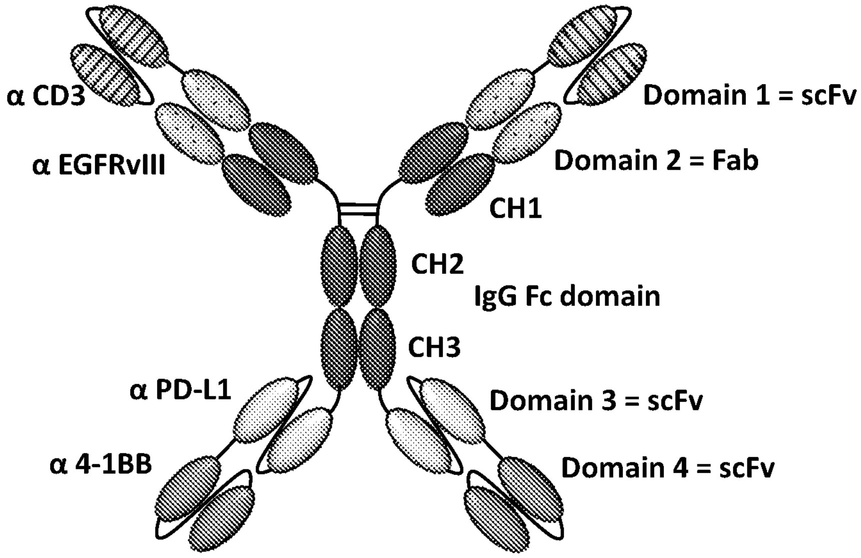

FIGURE 2B. General format of a tetra-specific GNC antibody with an ROR1 AgBD (SI-35E20).
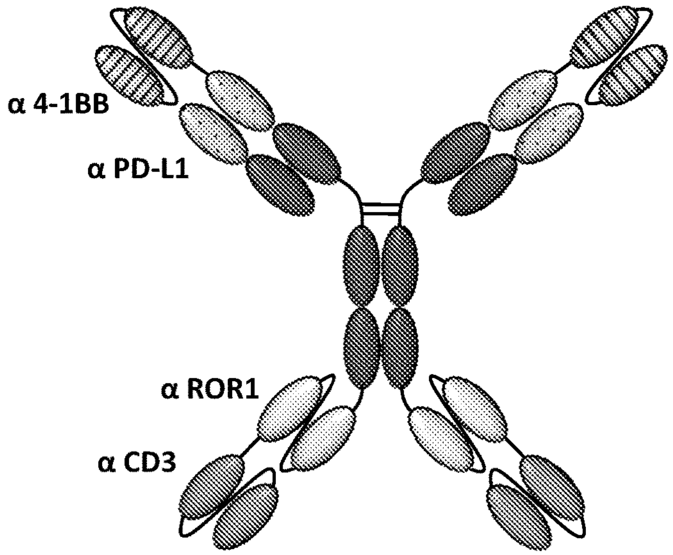
FIGURE 2C. General format of a tetra-specific GNC antibody with an CD19 AgBD (SI-38E17).
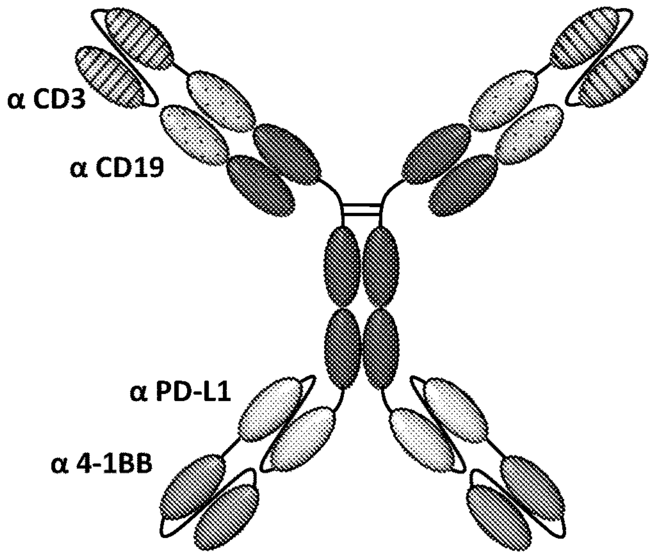

FIGURE 3. A tetra-specific GNC antibody binds to both a T cell and a tumor cell through multiple AgBDs.
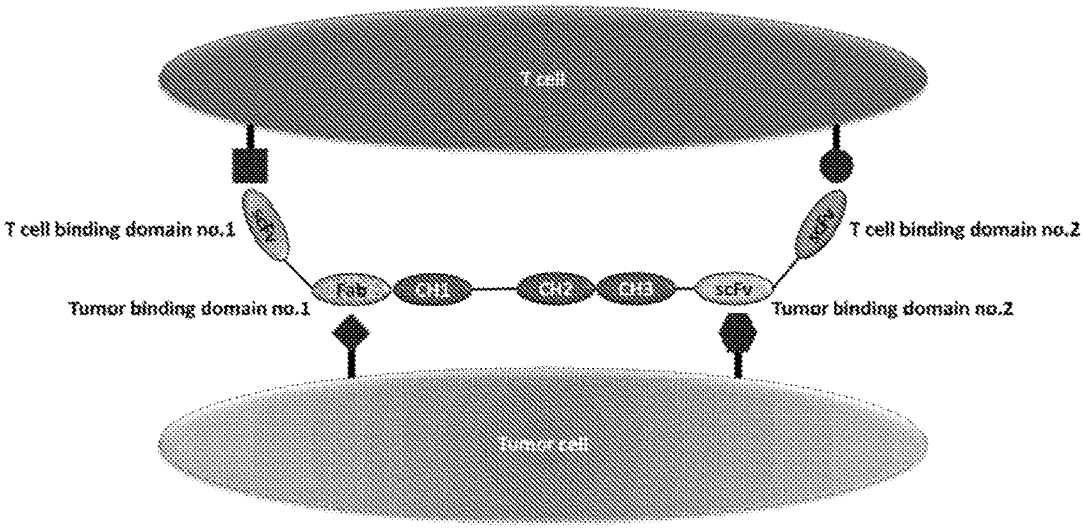

FIGURE 4. The binding of tetra-specific GNC antibodies to human ROR1 transfected CHO cells.
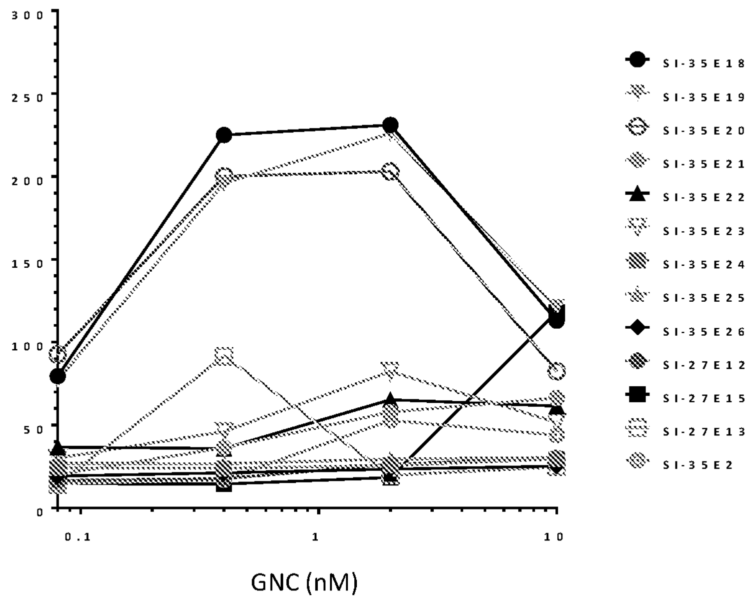

FIGURE 5. The binding of tetra-specific GNC antibodies to human 41BB transfected CHO cells.
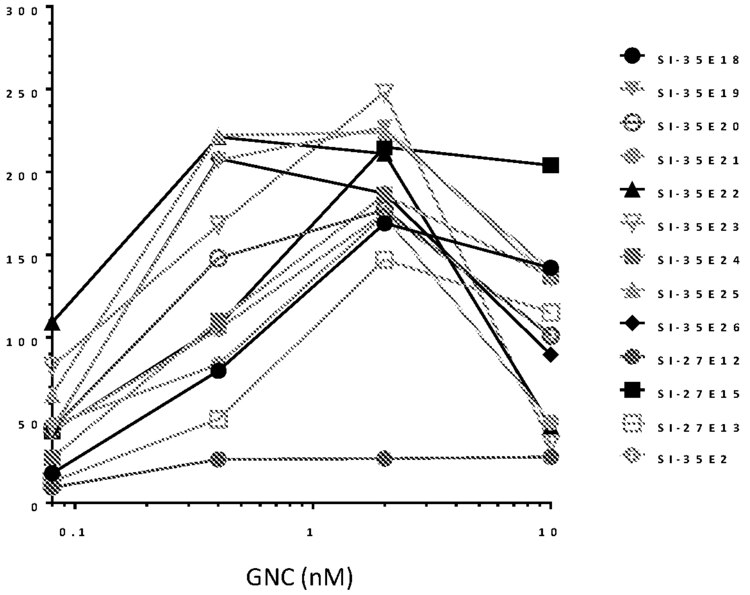

FIGURE 6. The binding of tetra-specific GNC antibodies to human PD-L1 transfected CHO cells.
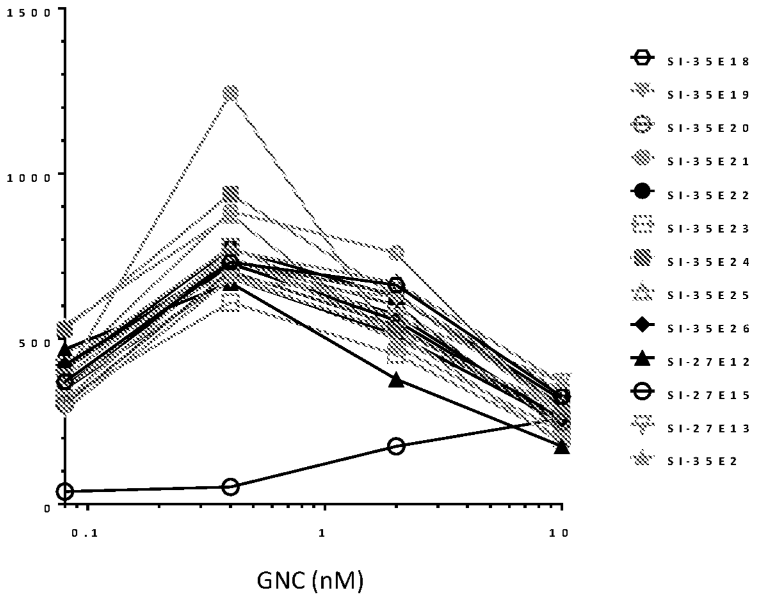

FIGURE 7. Tetra-specific GNC antibodies with the binding domain 323H7 which is specific for the Ig domain of ROR1 meditated RTCC of the B-ALL cell line Kasumi2 with PBMC as effectors.
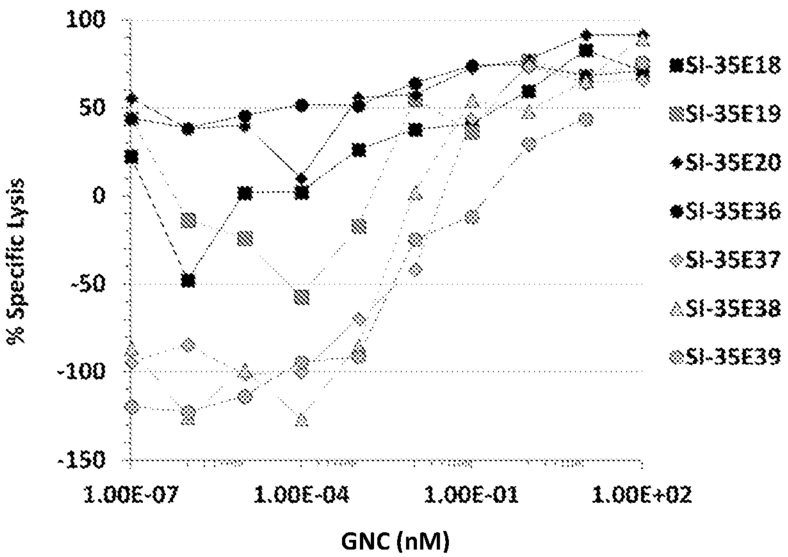

FIGURE 8. Tetra-specific GNC antibodies with the binding domain 323H7 which is specific for the Ig domain of ROR1 meditated RTCC of the B-ALL cell line Kasumi2 with CD8+, CD45RO+ memory T cells as effectors.
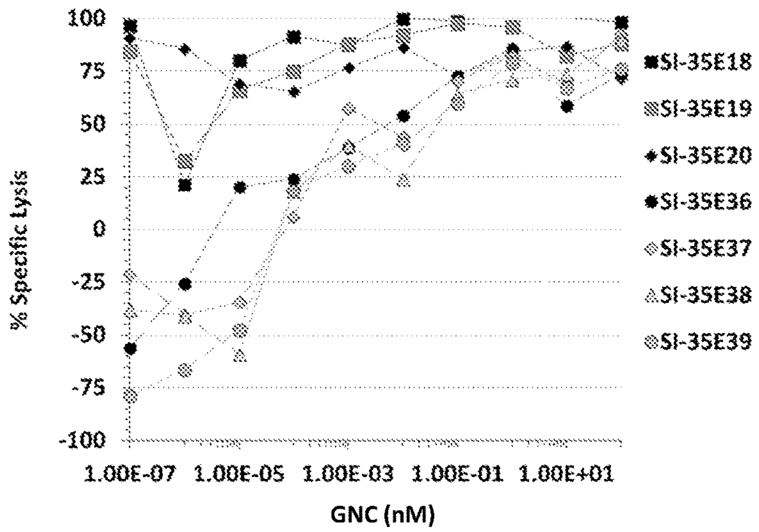

FIGURE 9. Tetra-specific GNC antibodies with the binding domain 323H7 which is specific for the Ig domain of ROR1 meditated RTCC of the B-ALL cell line Kasumi2 with CD8+, CD45RA+ naive T cells as effectors.
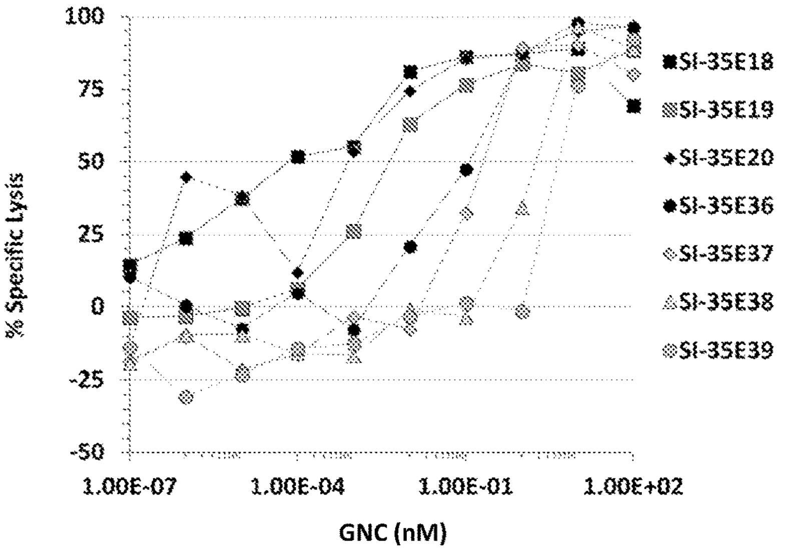

FIGURE 10. Tetra-specific GNC antibodies with the binding domain 338H4, which is specific for the Frizzled domain of ROR1 meditated RTCC of the B-ALL cell line Kasumi2 with PBMC as effectors.
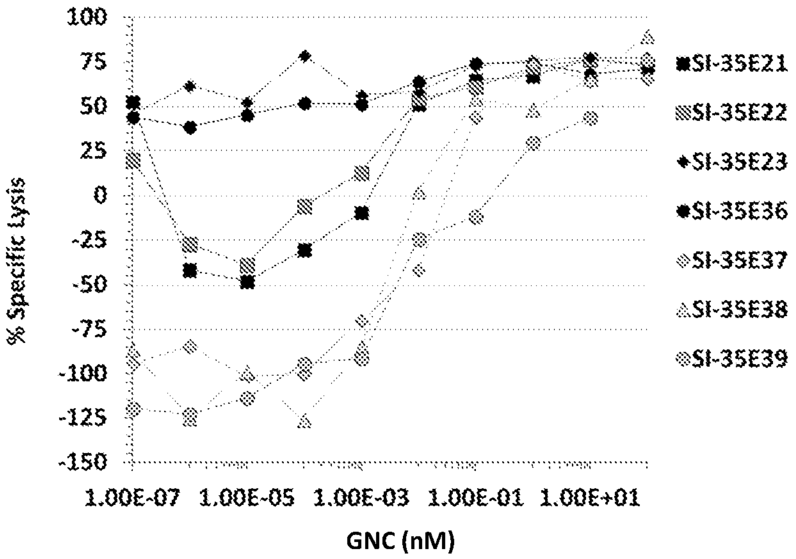

FIGURE 11. Tetra-specific GNC antibodies with the binding domain 338H4 which is specific for the Frizzled domain of ROR1 meditated RTCC of the B-ALL cell line Kasumi2 with CD8+, CD45RO+ memory T cells as effectors.
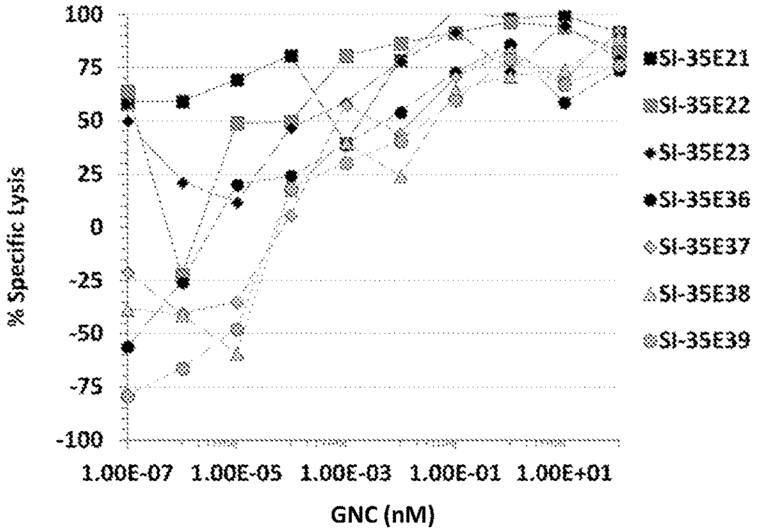

FIGURE 12. Tetra-specific GNC antibodies with the binding domain 338H4, which is specific for the Frizzled domain of ROR1 meditated RTCC of the B-ALL cell line Kasumi2 with CD8+, CD45RA+ naive T cells as effectors.
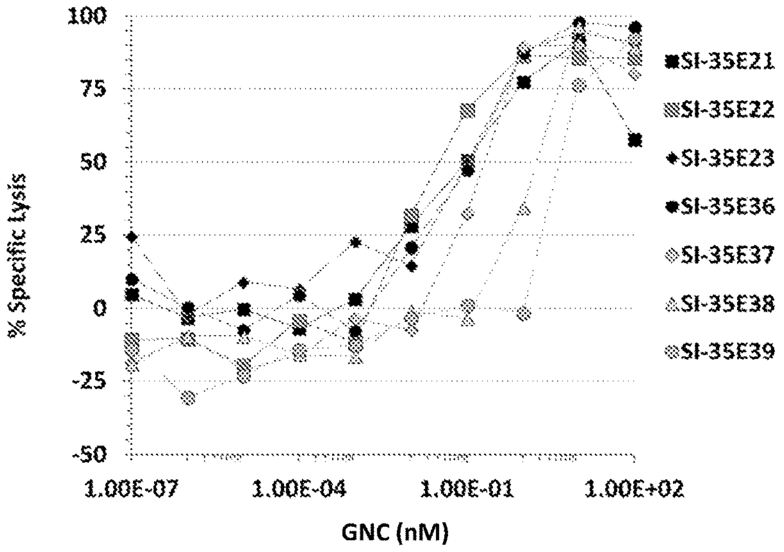

Figure 13. Redirected panT cell activity against bladder cancer cell line UM-UC-3- EGFRvIII in response to treatment with EGFRvIII targeting tetra-specific GNC antibodies.
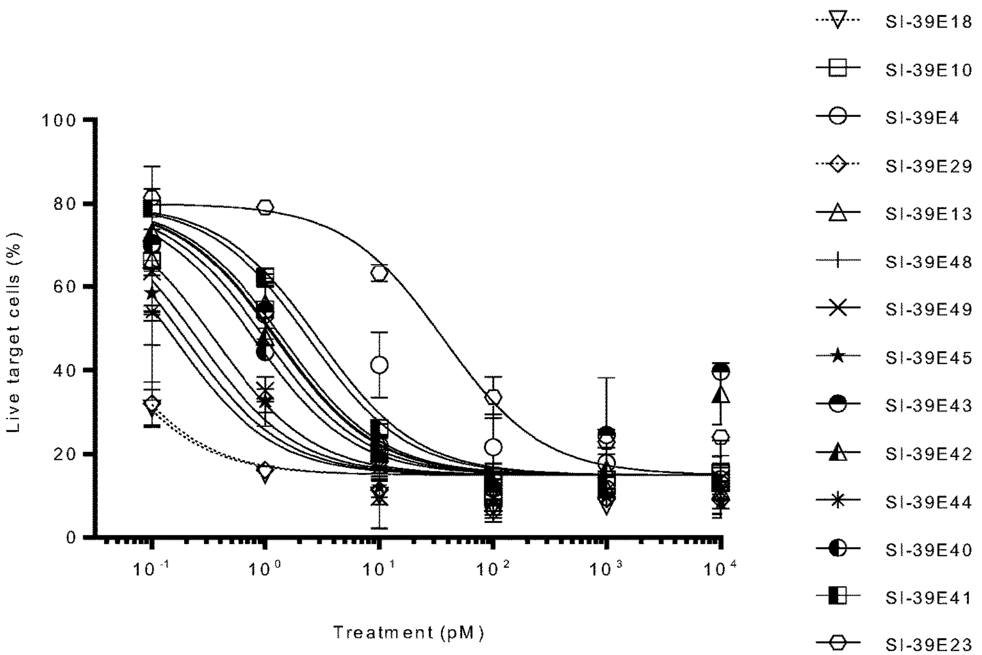

Figure 14. CD8 T cell proliferation in response to treatment with EGFRvIII targeting tetra-specific GNC antibodies.
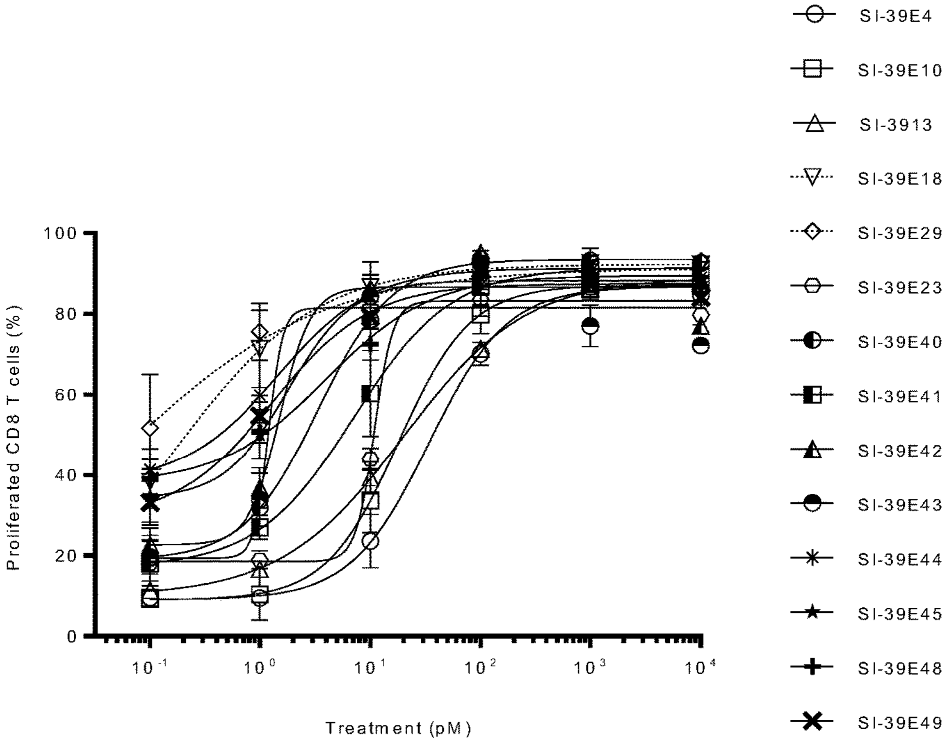

Figure 15. IFNγ secretion in response to treatment with EGFRvIII targeting tetra-specific GNC antibodies.
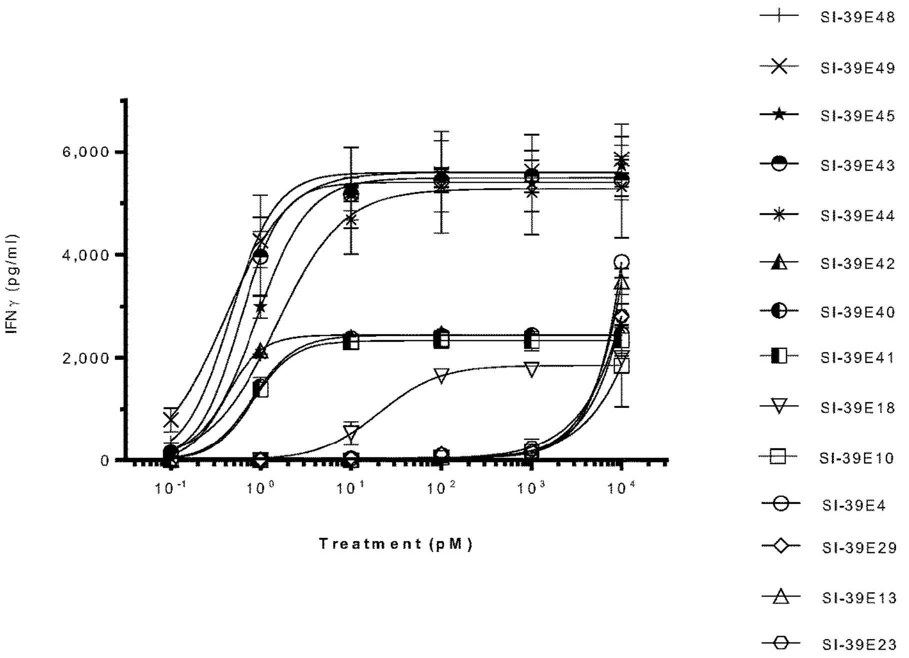

Figure 16. Redirected naïve T cell cytotoxicity against bladder cancer cell line UM-UC-3- EGFRvIII.
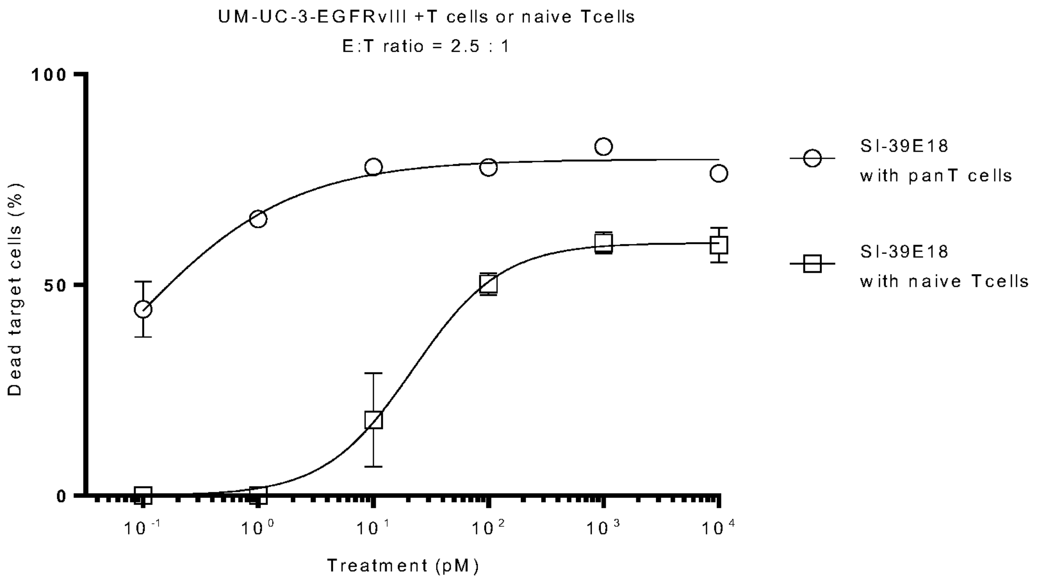

Figure 17. Response of PBMC to treatment with EGFRvIII targeting tetra-specific GNC antibodies, proliferation of CD8 T cells.
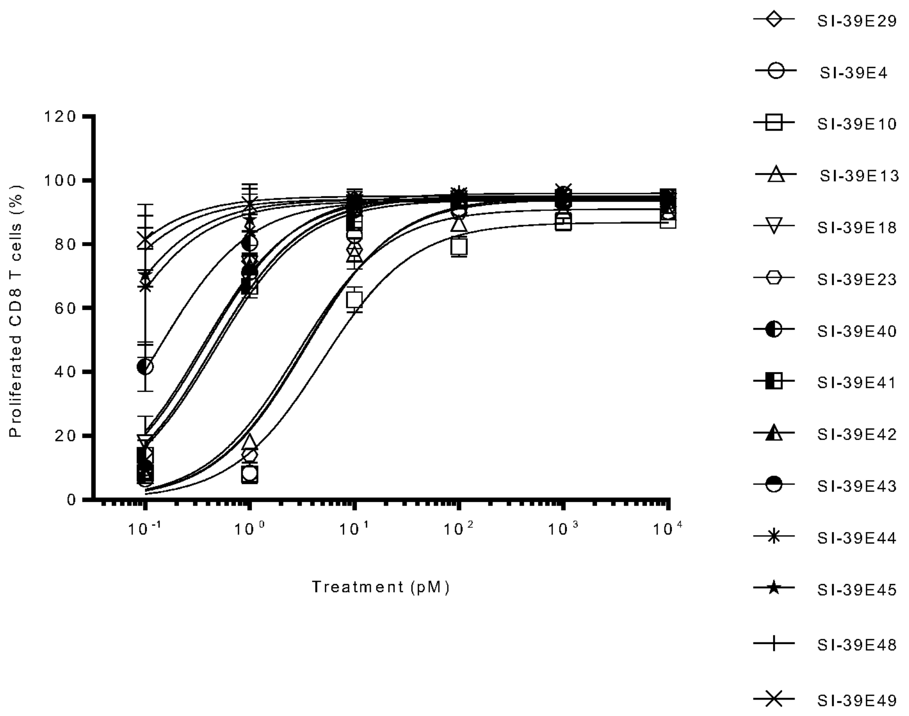

Figure 18. Redirected panT cell activity against bladder cancer cell line UM-UC-3- EGFRvIII in the presence of monocytes in response to treatment with EGFRvIII targeting tetra-specific GNC antibodies.
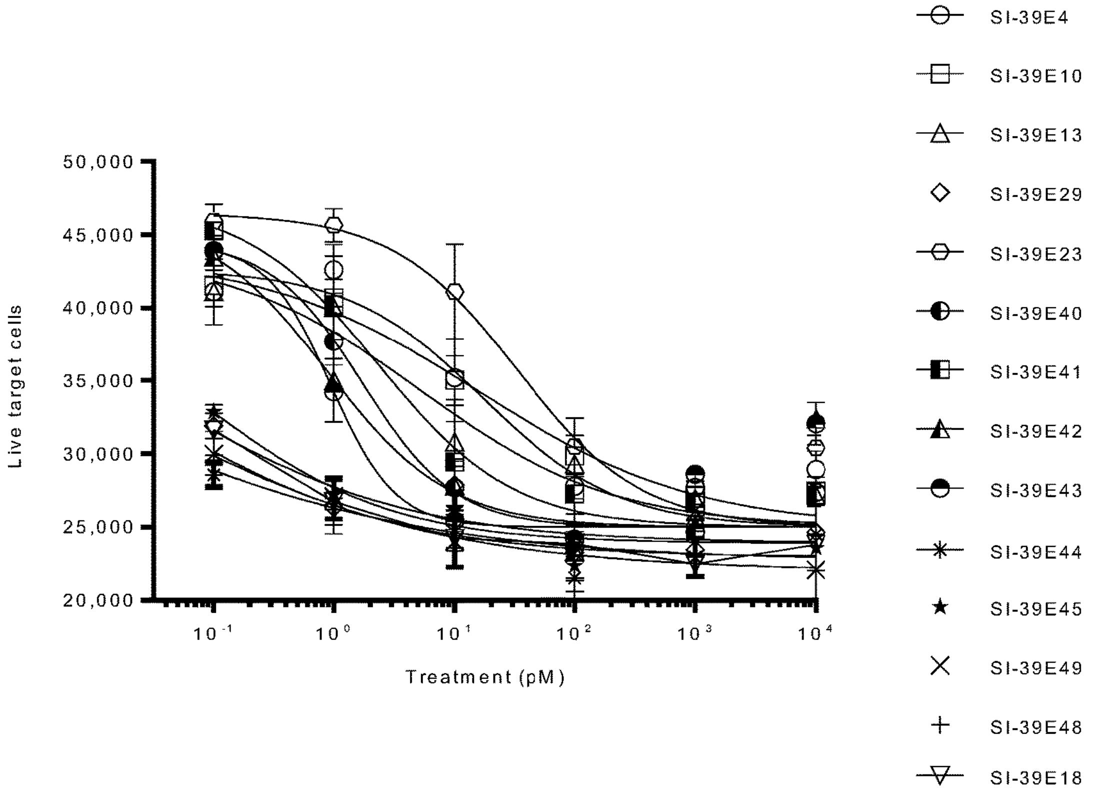

Figure 19. Functional impact of PD-L1 and 4-1BB domains on activity of tetra-specific GNC antibodies. Redirected PBMC cytotoxicity against bladder cancer cell line UM-UC-3-EGFRvIII.
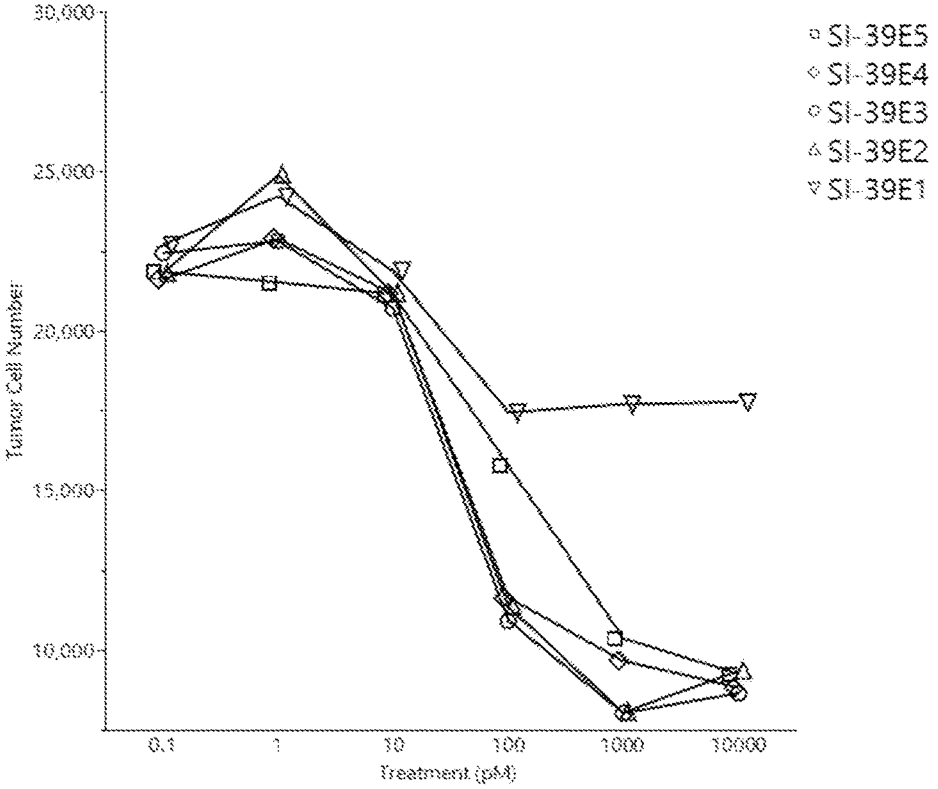

Figure 20. Redirected panT cell activity against Kasumi-2 target cell line in response to treatment with ROR1 targeting tetra-specific GNC antibodies.
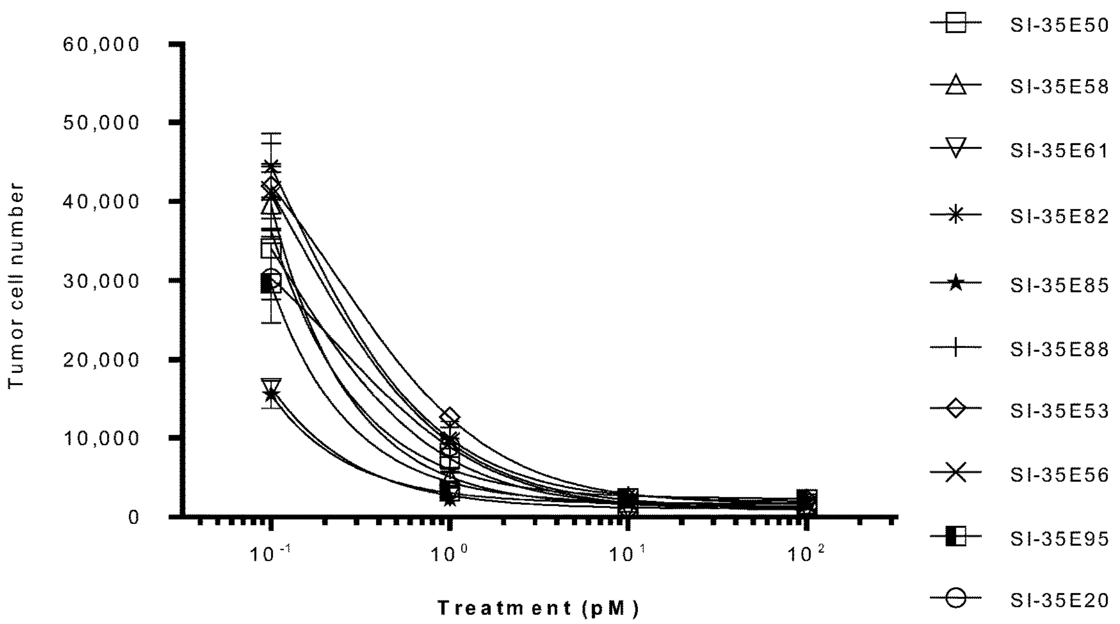

Figure 21. Redirected PBMC activity against Kasimu-2 tumor cell line in response to treatment with CD19 targeting tetra-specific GNC antibodies.
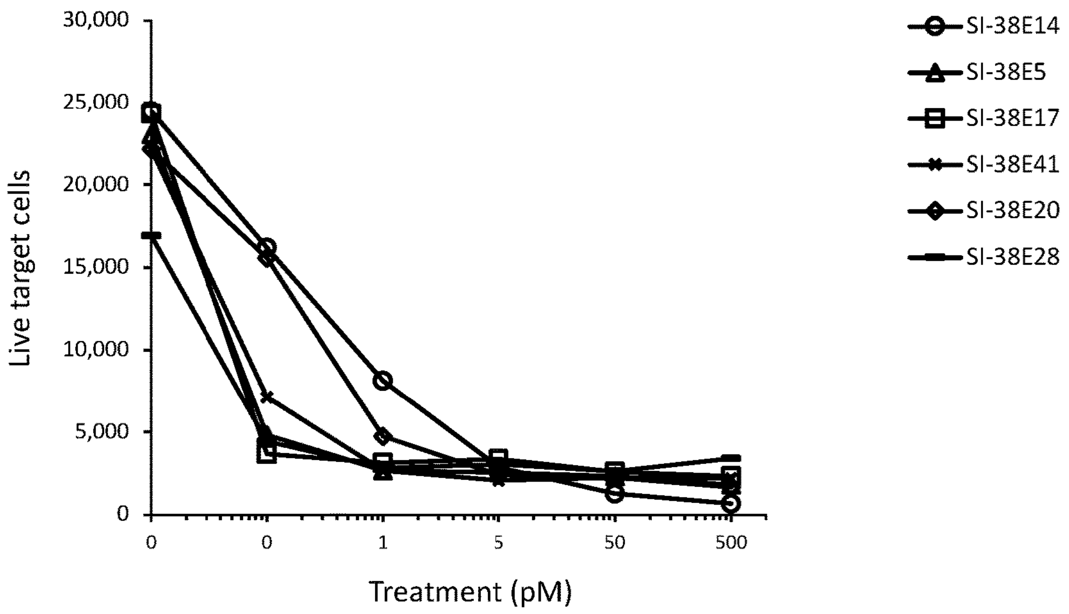

Figure 22. CD8 T cells proliferation in response to treatment with CD19 targeting tetra-specific GNC antibodies.
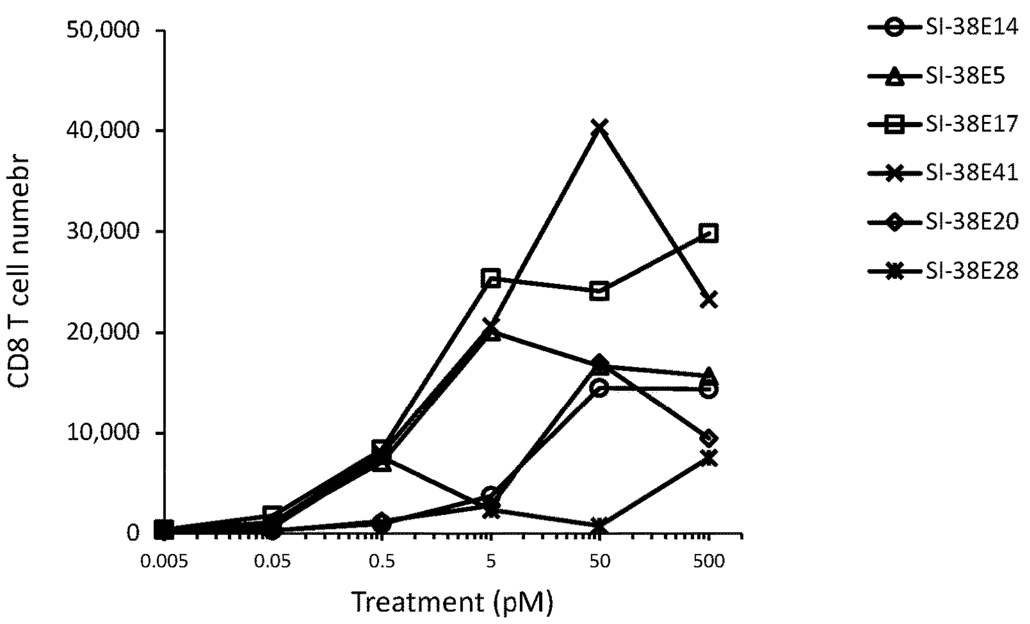

Figure 23. IFNγ production by PBMC in response to treatment with CD19 targeting tetra-specific GNC antibodies.
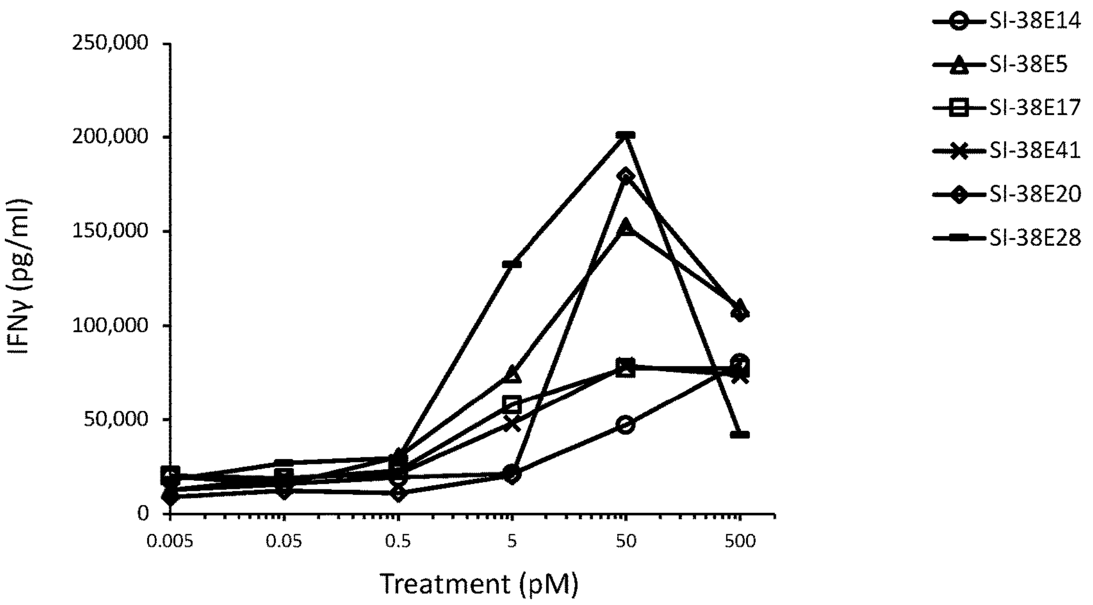

GUIDANCE AND NAVIGATION CONTROL PROTEINS AND METHOD OF MAKING AND USING THEREOF

CROSS REFERENCE TO RELATED APPLICATIONS

This application claims the benefit of U.S. Provisional Patent Application No. 62/648,880 filed Mar. 27, 2018, and U.S. Provisional Patent Application No. 62/648,888 filed Mar. 27, 2018, the entire disclosures of which are expressly incorporated by reference herein.

TECHNICAL FIELD

The present application generally relates to the technical field of Guidance and Navigation Control (GNC) proteins with multi-specific binding activities against surface molecules on both immune cells and tumor cells, and more particularly relates to making and using GNC proteins.

BACKGROUND

Cancer cells develop various strategies to evade the immune system. One of the underlaying mechanisms for the immune escape is the reduced recognition of cancer cells by the immune system. Defective presentation of cancer specific antigens or lack of thereof results in immune tolerance and cancer progression. In the presence of effective immune recognition tumors use other mechanisms to avoid elimination by the immune system. Immunocompetent tumors create suppressive microenvironment to downregulate the immune response. Multiple players are involved in shaping the suppressive tumor microenvironment, including tumor cells, regulatory T cells, myeloid-derived suppressor cells, stromal cells, and other cell types. The suppression of immune response can be executed in a cell contact-independent manner via secretion of immunosuppressive cytokines or elimination of essential survival factors from the local environment. The cell contact-dependent suppression relies on molecules expressed on the cell surface, e.g. Programmed Death Ligand 1 (PD-L1), T-lymphocyte-associated protein 4 (CTLA-4), and others [Dunn, et al., 2004, Immunity, 21(2): 137-48; Adachi & Tamada, 2015, Cancer Sci., 106(8): 945-50].

As the mechanisms by which tumors evade recognition by the immune system continue to be better understood, new treatment modalities that target these mechanisms have recently emerged. On Mar. 25, 2011, the U. S. Food and Drug Administration (FDA) approved 1pilimurnab injection (Yervoy, Bristol-Myers Squibb) for the treatment of unresectable or metastatic melanoma. Yervoy binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumor. A few years later in 2014 the FDA approved Keytruda (Pembrolizumab, Merck) and Opdivo (Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumors thereby eliminating the inhibitory signal through PD-1 into the T cell resulting in re-activation of the antigen-specific T cell leading to again, in many patients, eradication of the tumor. Since then additional clinical trials have been performed comparing the single monoclonal antibody Yervoy to the combination of the monoclonal antibodies Yervoy and Opdivo in the treatment of advanced melanoma which showed improvement in overall survival and progression-free survival in the patients treated with the combination of antibodies. (Hodi et al., 2016, Lancet Oncol. 17(11):1558-1568, Hellman et al., 2018, Cancer Cell 33(5): 853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371:2189-2199). Those patients that have a low tumor mutational load mostly do not show an objective clinical response (Snyder et al., 2014, NEJM 371:2189-2199, Hellman et al., 2018, Cancer Cell 33(5): 853-861).

In recent years other groups have developed an alternate approach that does not require the presence of neoepitope presentation by antigen-presenting cells to activate T cells. One example is the development of a bi-specific antibody where the binding domain of an antibody which is specific for a tumor associated antigen, e.g., CD19, is linked to and antibody binding domain specific for CD3 on T cells thus creating a bi-specific T cell engager or BiTe molecule. In 2014, the FDA approved a bi-specific antibody called Blinatumumab for the treatment of Precursor B-Cell Acute Lymphoblastic Leukemia. Blinatumumab links the scFv specific for CD19 expressed on leukemic cells with the scFv specific for CD3 expressed on T cells (Bejnjamin and Stein 2016, Ther Adv Hematol 7(3):142-146). However, despite an initial response rate of >50% in patients with relapsed or refractory ALL many patients are resistant to Blinatumumab therapy or relapse after successful treatment with Blinatumumab. Evidence is emerging that the resistant to Blinatumumab or who relapse after Blinatumumab treatment is attributable to the expression of immune checkpoint inhibitory molecules expressed on tumor cells, such as PD-L1 that drives an inhibitory signal through PD-1 expressed on activated T cells (Feucht et al., 2016, Oncotarget 7(47): 76902-76919). In a case study of a patient who was resistant to therapy with Blinatumumab, a second round of Blinatumumab therapy was performed but with the addition of a monoclonal antibody, pembrolizumab (Keytruda, Merck), which specifically binds to PD-1 and blocks the interaction of T cell-expressed PD-1 with tumor cell expressed PD-L1, resulted in a dramatic response and reduction of tumor cells in the bone marrow from 45% to less than 5% in this one patient (Feucht et al., 2016, Oncotarget 7(47):76902-76919). These results show that combining a bi-specific BiTe molecule with one or more monoclonal antibodies can significantly increase clinical activity compared to either agent alone. Despite the promising outcome, the cost leading to the combined therapy must be high due to multiple clinical trials and the difficulty in recruiting representative populations.

Adoptive cell therapy with chimeric antigen receptor T cells (CAR-T) is another promising immunotherapy for treating cancer. The clinical success of CAR-T therapy has revealed durable complete remissions and prolonged survival of patients with CD19-positive treatment-refractory B cell malignancies (Gill & June. 2015. Immunol Rev, 263: 68-89). However, the cost and complexity associated with the manufacture of a personalized and genetically modified CAR-T immunotherapy has restricted their production and use to specialized centers for treating relatively small numbers of patients. Cytokine release syndrome (CRS), also known as cytokine storms, is the most notable adverse effect after the infusion of engineered CAR-T cells (Bonifant et al., 201, Mol Ther Oncolytics. 3: 16011). In many cases, the onset and severity of CRS seems to be specialized personal events. Current options of mitigating CRS are mainly focused on rapid response and management care because the option of controlling CRS prior to T cell infusion is limited.

While the efficacy of CAR-T therapy specific for a CD19-positive B cell malignancy is now established, the efficacy of CAR-T therapy against solid tumors has not been unequivocally demonstrated to date. Currently, many clinical trials are in progress to explore a variety of solid tumor-associated antigens (TAA) for CAR-T therapy. Inefficient T cell trafficking into the tumors, an immunosuppressive tumor micro-environment, suboptimal antigen recognition specificity, and lack of control over treatment-related adverse events are currently considered as the main obstacles in solid tumor CAR-T therapy (Li et al., 2018, J Hematol Oncol. 11(1):22-40). The option of managing the therapeutic effect, as well as any adverse effect before and after the CAR-T cell infusion, is limited.

SUMMARY

The present application provides guidance and navigation control (GNC) proteins with multi-specific antigen binding activities to the surface molecules of a T cell and a tumour cell. In one embodiment, the guidance and navigation control (GNC) protein comprises a binding domain for a T cell activating receptor, a binding domain for a tumor associated antigen, a bind domain for an immune checkpoint receptor, and a binding domain for a T cell co-stimulating receptor.

In one embodiment, the binding domain for the tumor associated antigen is not adjacent to the binding domain for the T cell co-stimulating receptor. In one embodiment, the binding domain for the T cell activating receptor is adjacent to the binding domain for the tumor associated antigen (TAA). The T cell activating receptor may include without limitation CD3. The T cell co-stimulating receptor may include without limitation 4-1BB, CD28, OX40, GITR, CD40L, ICOS, Light, CD27, CD30, or a combination thereof. The immune checkpoint receptor may include without limitation PD-L1, PD-1, TIGIT, TIM-3, LAG-3, CTLA4, BTLA, VISTA, PDL2, CD160, LOX-1, siglec-15, CD47, or a combination thereof.

The tumor associated antigen (TAA) may include without limitation ROR1, CD19, EGFRVIII, BCMA, CD20, CD33, CD123, CD22, CD30, CEA, HER2, EGFR, LMP1, LMP2A, Mesothelin, PSMA, EpCAM, glypican-3, gpA33, GD2, TROP2, or a combination thereof. In one embodiment, the tumor associated antigen may be ROR1. In one embodiment, the tumor associated antigen may be CD19. In one embodiment, the tumor associated antigen may be EGFRVIII.

In on embodiment, the tumor associated antigen may be a receptor on a lung cancer cell, a liver cancer cell, a breast cancer cell, a colorectal cancer cell, an anal cancer cell, a pancreatic cancer cell, a gallbladder cancer cell, a bile duct cancer cell, a head and neck cancer cell, a nasopharyngeal cancer cell, a skin cancer cell, a melanoma cell, an ovarian cancer cell, a prostate cancer cell, a urethral cancer cell, a lung cancer cell, a non-small lung cell cancer cell, a small cell lung cancer cell, a brain tumour cell, a glioma cell, a neuroblastoma cell, an esophageal cancer cell, a gastric cancer cell, a liver cancer cell, a kidney cancer cell, a bladder cancer cell, a cervical cancer cell, an endometrial cancer cell, a thyroid cancer cell, an eye cancer cell, a sarcoma cell, a bone cancer cell, a leukemia cell, a myeloma cell, a lymphoma cell, or a combination thereof. In one embodiment, the tumor associated antigen may be a receptor on a B cell.

In one embodiment, the guidance and navigation control (GNC) protein may be an antibody or an antibody monomer or a fragment thereof. In one embodiment, the GNC protein may be a tri-specific antibody. In one embodiment, the GNC protein may be a tetra-specific antibody. In one embodiment, the GNC protein includes Fc domain or a fragment thereof. Any Fc domain from an antibody may be used. Example Fc domains may include Fc domains from IgG, IgA, IgD, IgM, IgE, or a fragment or a combination thereof. Fc domain may be natural or engineered. In one embodiment, the Fc domain may contain an antigen binding site.

In one embodiment, the guidance and navigation control (GNC) protein is an antibody. In one embodiment, the tumor associated antigen comprises ROR1, CD19, or EGRFVIII. In on embodiment, the T cell activating receptor comprises CD3 and the binding domain for CD3 may be linked to the binding domain for the tumor associated (TAA) antigen through a linker to form a CD3-TAA pair. In one embodiment, the IgG Fc domain may intermediate the CD3-TAA pair and the binding domain for the immune checkpoint receptor. In one embodiment, the immune checkpoint receptor may be PD-L1.

In one embodiment, the linker may be a covalent bond. In one embodiment, the linker may be a peptide linker. In one embodiment, the peptide linker has length not exceeding 100 amino acids. In one embodiment, the peptide linker has a length not exceeding 2, 5, 10, 20, 30, 40, 50, 60, 70, 80, 90 or 100 amino acids. In one embodiment, the peptide linker has a length not exceeding 10 amino acids. In one embodiment, the peptide linker has a length from about 2 amino acids to about 10 amino acids. In one embodiment, the peptide linker includes 2, 5, or 10 amino acids.

In on embodiment, the guidance and navigation control (GNC) protein has a N-terminal and a C-terminal, comprising in tandem from the N-terminal to the C-terminal, the binding domain for CD3, the binding domain for EGFRVIII, IgG Fc domain, the bind domain for PD-L1, and the binding domain for 41-BB. In one embodiment, the GNC protein may include an amino acid sequence having a percentage homology to SEQ ID NO. 80 and 82. The percentage homology is not less than 70%, 80%, 90%, 95%, 98% or 99%. In one embodiment, the GNC protein is a tetra-specific antibody.

In one embodiment, the guidance and navigation control (GNC) protein has a N-terminal and a C-terminal, comprising in tandem from the N-terminal to the C-terminal, the binding domain for 4-1BB, the binding domain for PD-L1, IgG Fc domain, the bind domain for ROR1, and the binding domain for CD3. In one embodiment, the GNC protein includes an amino acid sequence having a percentage homology to SEQ ID NO. 88 and 90. The percentage homology is not less than 70%, 80%, 90%, 95%, 98% or 99%. In one embodiment, the GNC protein is a tetra-specific antibody.

The guidance and navigation control (GNC) protein has a N-terminal and a C-terminal, comprising in tandem from the N-terminal to the C-terminal, the binding domain for CD3, the binding domain for CD19, IgG Fc domain, the bind domain for PD-L1, and the binding domain for 4-1BB. In one embodiment, the GNC protein includes an amino acid sequence having a percentage homology to SEQ ID NO. 104 and 106. The percentage homology is not less than 70%, 80%, 90%, 95%, 98% or 99%. In one embodiment, the GNC protein is a tetra-specific antibody.

In one embodiment, the GNC protein comprises an amino acid having a percentage homology to SEQ ID NO. 50, 52, 80, 82, 84, 86, 88, 90, 92, 94, 96, 98, 100, 102, 104, 106, 108 and 110, and the percentage homology is not less than 70%, 80%, 90%, 95%, 98% or 99%.

In another aspect, the application provides nucleic acid sequences encoding the GNC protein or its fragments disclosed thereof. In one embodiment, the nucleic acid has a percentage homology to SEQ ID NO. 49, 51, 79, 81, 83, 85, 87, 89, 91, 93, 95, 97, 99, 101, 103, 105, 107, and 109, and the percentage homology is not less than 70%, 80%, 90%, 95%, 98% or 99%.

In one embodiment, the guidance and navigation control (GNC) protein, comprising a cytotoxic cell binding moiety and a cancer-targeting moiety. Any cytotoxic cells may be a potential binding target by the disclosed GNC proteins. Examples of the cytotoxic cell include, without limitation, T-cell, NK cell, macrophage cell, and dendritic cell.

In one embodiment, the GNC protein includes a T-cell binding moiety. The T-cell binding moiety has a binding specificity to a T-cell receptor. Examples T-cell receptor include without limitation CD3, CD28, PDL1, PD1, OX40, 4-1BB, GITR, TIGIT, TIM-3, LAG-3, CTLA4, CD40L, VISTA, ICOS, BTLA, Light, CD30, NKp30, CD28H, CD27, CD226, CD96, CD112R, A2AR, CD160, CD244, CECAM1, CD200R, TNFRSF25 (DR3), or a combination thereof.

In one embodiment, the GNC protein includes a NK cell binding moiety. The NK cell binding moiety has a binding specificity to a NK cell receptor. Examples NK cell receptor include, without limitation, receptors for activation of NK cell such as CD16, NKG2D, KIR2DS1, KIR2DS2, KIR2DS4, KIR3DS1, NKG2C, NKG2E, NKG2H; agonist receptors such as NKp30a, NKp30b, NKp46, NKp80, DNAM-1, CD96, CD160, 4-1BB, GITR, CD27, OX-40, CRTAM; and antagonist receptors such as KIR2DL1, KIR2DL2, KIR2DL3, KIR3DL1, KIR3DL2, KIR3DL3, NKG2A, NKp30c, TIGIT, SIGLEC7, SIGLEC9, LILR, LAIR-1, KLRG1, PD-1, CTLA-4, CD161.

In one embodiment, the GNC protein includes a macrophage binding moiety. The macrophage binding moiety has a binding specificity to a macrophage receptor. Examples macrophage receptor include, without limitation, agonist receptor on macrophage such as TLR2, TLR4, CD16, CD64, CD40, CD80, CD86, TREM-1, TREM-2, ILT-1, ILT-6a, ILT-7, ILT-8, EMR2, Dectin-1, CD69; antagonist receptors such as CD32b, SIRPa, LAIR-1, VISTA, TIM-3, CD200R, CD300a, CD300f, SIGLEC1, SIGLEC3, SIGLEC5, SIGLEC7, SIGLEC9, ILT-2, ILT-3, ILT-4, ILT-5, LILRB3, LILRB4, DCIR; and other surface receptors such as CSF-1R, LOX-1, CCR2, FRB, CD163, CR3, DC-SIGN, CD206, SR-A, CD36, MARCO.

In one embodiment, the GNC protein includes a dendritic cell binding moiety. The dendritic cell binding moiety has a binding specificity to a dendritic cell receptor. Examples dendritic cell receptor include, without limitation, agonist receptors on dendritic cell such as TLR, CD16, CD64, CD40, CD80, CD86, HVEM, CD70; antagonist receptors such as VISTA, TIM-3, LAG-3, BTLA; and other surface receptors such as CSF-1R, LOX-1, CCR7, DC-SIGN, GM-CSF-R, IL-4R, IL-10R, CD36, CD206, DCIR, RIG-1, CLEC9A, CXCR4.

The cancer targeting moiety has a binding specificity to a cancer cell receptor. Example cancer cell receptor include without limitation BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2, or a combination thereof.

In one embodiment, GNC proteins comprise at least one T-cell binding moiety and at least one cancer cell binding moiety, wherein the T-cell binding moiety has a binding specificity to a T-cell receptor comprising CD3, CD28, PDL1, PD1, OX40, 4-1BB, GITR, TIGIT, TIM-3, LAG-3, CTLA4, CD40, VISTA, ICOS, BTLA, Light, CD30, CD27, or a combination thereof, and wherein the cancer cell binding moiety has a binding specificity to a cancer cell receptor.

In one embodiment, the GNC protein is capable of activating a T-cell by binding the T-cell binding moiety to a T-cell receptor on the T-cell. In one embodiment, the GNC protein comprises a bi-specific antibody or antibody monomer, a tri-specific antibody or antibody monomer, a tetra-specific antibody or antibody monomer, an antigen-binding fragment thereof, or a combination thereof.

In one embodiment, the GNC protein may have a first moiety and a second moiety. In one embodiment, the first moiety may include a T-cell binding moiety, a NK cell binding moiety, a macrophage binding moiety, or a dendritic cell binding moiety. The second moiety comprises the cancer-targeting moiety.

The application further provides a cytotoxic cell incorporating the GNC protein disclosed herein. In one embodiment, the cytotoxic includes the GNC protein and a cytotoxic cell. The cytotoxic cell may T cell, NK cell, macrophage, dendritic cell, or a combination thereof. In one embodiment, the T cell may be autologous T cells, allo T cells, or universal donor T cells. In one embodiment, the cytotoxic cell includes a T cell having a T cell activating receptor and a T cell co-stimulating receptor, and the GNC protein bound to the T cell through interaction with the T cell activating receptor, the T cell co-stimulating receptor, or a combination there.

The application further provides a cancer cell incorporating the GNC protein disclosed herein. In one embodiment, the cancer cell, comprising a cancer cell having a tumor associated antigen, and the GNC protein of claim 1 bound to cancer cell through the interaction with the tumor associated antigen.

The application further provides a biological complex incorporating the GNC protein disclosed herein. In one embodiment, the biological complex includes a T cell having a T cell activating receptor and a T cell co-stimulating receptor, a cancer cell having a tumor associated antigen, and the GNC protein of claim 1, wherein the GNC protein is bound to the T cell through the interaction with the T cell activating receptor, the T cell co-stimulating receptor, or a combination thereof and wherein the GNC protein is bound to the cancer cell through the interaction with the tumor associated antigen.

In a further aspect, the application provides a pharmaceutical composition useful for treating a cancer condition. In one embodiment, the pharmaceutical composition includes the GNC protein or cytotoxic cell disclosed herein, and a pharmaceutically acceptable carrier.

In a further aspect, the application provides methods for making and using the disclosed GNC proteins.

In a further aspect, the application provides methods for treating a subject having a cancer. In one embodiment, the method includes the step of administering to the subject an effective amount of the pharmaceutical composition disclosed herein.

The objectives and advantages of the present application will become apparent from the following detailed description of preferred embodiments thereof in connection with the accompanying drawings.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows a general scheme of GNC proteins characterized by their composition of multiple antigen binding domains (AgBd) and linkers;

FIG. 2 shows examples of GNC antibodies as an embodiment of the GNC protein disclosed herein: 2A, a tetra-specific GNC antibody with an EGFRvIII AgBD (SI-39E18); 2B, a tetra-specific GNC antibody with an ROR1 AgBD (SI-35E20); and 2C, a tetra-specific GNC antibody with an CD19 AgBD (SI-38E17);

FIG. 3 illustrates how a tetra-specific GNC antibody may bind to both a T cell and a tumor cell through multiple AgBDs;

FIG. 4 shows examples of tetra-specific GNC antibody binding to human ROR1 transfected CHO cells;

FIG. 5 shows examples of tetra-specific GNC antibody binding to human 4-1BB transfected CHO cells;

FIG. 6 shows examples of tetra-specific GNC antibody binding to human PD-L1 transfected CHO cells;

FIG. 7 shows the example tetra-specific GNC antibodies with the binding domain 323H7, which is specific for the Ig domain of ROR1 meditated RTCC of the B-ALL cell line Kasumi2 with PBMC as effectors;

FIG. 8 shows the example tetra-specific GNC antibodies with the binding domain 323H7, which is specific for the Ig domain of ROR1 meditated RTCC of the B-ALL cell line Kasumi2 with CD8+, CD45RO+ memory T cells as effectors;

FIG. 9 shows the example tetra-specific GNC antibodies with the binding domain 323H7, which is specific for the Ig domain of ROR1 meditated RTCC of the B-ALL cell line Kasumi2 with CD8+, CD45RA+ naive T cells as effectors;

FIG. 10 shows the example tetra-specific GNC antibodies with the binding domain 338H4, which is specific for the Frizzled domain of ROR1 meditated RTCC of the B-ALL cell line Kasumi2 with PBMC as effectors;

FIG. 11 shows the example tetra-specific GNC antibodies with the binding domain 338H4, which is specific for the Frizzled domain of ROR1 meditated RTCC of the B-ALL cell line Kasumi2 with CD8+, CD45RO+ memory T cells as effectors;

FIG. 12 shows the example tetra-specific GNC antibodies with the binding domain 338H4, which is specific for the Frizzled domain of ROR1 meditated RTCC of the B-ALL cell line Kasumi2 with CD8+, CD45RA+ naive T cells as effectors;

FIG. 13 displays redirected panT cell activity against bladder cancer cell line UM-UC-3-EGFRvIII in response to treatment with EGFRvIII targeting tetra-specific GNC antibodies;

FIG. 14 shows the results of measuring CD8 T cell proliferation in response to treatment with EGFRvIII targeting tetra-specific GNC antibodies;

FIG. 15 shows the results of tracking IFNγ secretion in response to treatment with EGFRvIII targeting tetra-specific GNC antibodies;

FIG. 16 shows the results of demonstrating redirected naïve T cell cytotoxicity against bladder cancer cell line UM-UC-3-EGFRvIII;

FIG. 17 shows the results of measuring the response of PBMC to treatment with EGFRvIII targeting tetra-specific GNC antibodies, proliferation of CD8 T cells;

FIG. 18 shows the results of redirected panT cell activity against bladder cancer cell line UM-UC-3-EGFRvIII in the presence of monocytes in response to treatment with EGFRvIII targeting tetra-specific GNC antibodies;

FIG. 19 shows the functional impact of PD-L1 and 4-1BB domains on activity of tetra-specific GNC antibodies and redirected PBMC cytotoxicity against bladder cancer cell line UM-UC-3-EGFRvIII;

FIG. 20 shows the results of redirected panT cell activity against Kasumi-2 target cell line in response to treatment with ROR1 targeting tetra-specific GNC antibodies;

FIG. 21 shows the results of redirected PBMC activity against Kasimu-2 tumor cell line in response to treatment with CD19 targeting tetra-specific GNC antibodies;

FIG. 22 shows CD8 T cells proliferation in response to treatment with CD19 targeting tetra-specific GNC antibodies; and FIG. 23 displays IFNγ production by PBMC in response to treatment with CD19 targeting tetra-specific GNC antibodies.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present application relates to methods of making and using GNC proteins. In one embodiment, the guidance navigation control (GNC) proteins may include multiple antigen-specific binding domains (AgBDs) and may have the ability of directing T cells (or other effector cells) to cancer cells (or other target cells) through the binding of multiple surface molecules on a T cell and a tumor cell (FIG. 1). In one embodiment, GNC proteins may be composed of Moiety 1 for binding at least one surface molecule on a T cell and Moiety 2 for binding at least one surface antigen on a cancer cell (TABLE 1A).

In a T cell therapy, the cytotoxic T cells are regulated by T cell proliferation signaling, as well as co-stimulation signaling via either agonist receptors or antagonist receptors on their surface. To regulate these signaling, as well as the interplay between a T cell and a cancer, multiple AgBDs may be included for Moiety 1 and Moiety 2, respectively and independently. GNC proteins may have at least one linker to link Moiety 1 and Moiety 2. The linker may vary in length. In one embodiment, the linker may be a covalent bond. In one embodiment, the linker may be a peptide having from about 1 to about 100 amino acid residues.

In some embodiments, any linker molecule can be used to link two or more AgBDs together either in vitro or in vivo by using complementary linkers of DNA/RNA or protein-protein interactions, including but not limited to, that of biotin-avidin, leucine-zipper, and any two-hybrid positive protein.

In some embodiments, the linkers may be an antibody backbone structure or antibody fragments, so that GNC protein and GNC antibody may have the same meaning, as show in FIG. 2, an example tetra-specific GNC antibody structure. In one embodiment, the GNC protein may be a bi-specific, tri-specific, tetra-specific, penta-specific, hexa-specific, hepta-specific, or octa-specific proteins. In one embodiment, the GNC protein may be a monoclonal antibody. In one embodiment, the GNC protein may be a bi-specific, tri-specific, tetra-specific, penta-specific, hexa-specific, hepta-specific, or octa-specific antibody monomers. In one embodiment, the GNC protein may be a bi-specific, tri-specific, tetra-specific, penta-specific, hexa-specific, hepta-specific, or octa-specific antibodies.

GNC proteins or antibodies may be capable of directing the binding of a T cell to a cancer cell in vivo or ex vivo, mediated by multiple AgBDs (FIG. 3). The T cells may be derived from the same patient or different individuals, and the cancer cell may exist in vivo, in vitro, or ex vivo. The examples provided in the present application enable GNC proteins as a prime agent in a T cell therapy, i.e. GNC-T therapy, for activating and controlling cytotoxic T cells ex vivo, prior to adoptive transfer.

In addition to T cells, other cytotoxic cells may be utilized by the GNC proteins for cancer killing or preventing purposes. TABLE 1B shows the example compositions of functional moieties (Moiety 1 and Moiety 2) and antigen binding domain in GNC proteins with NK cell binding domains. TABLE 1C shows the example compositions of functional moieties (Moiety land Moiety 2) and antigen binding domain in GNC proteins with macrophage binding domains. TABLE 1D shows the example compositions of functional moieties (Moiety 1 and Moiety 2) and antigen binding domain in GNC proteins with dendritic cell binding domains.

Multiple AgBDs can be divided into Moiety 1 and Moiety 2 due to their interface with a cytotoxic cell such as a T cell and a cancer cell, respectively (TABLE 1A). However, the rearrangement of multiple AgBDs may be random and in unequal numbers (TABLE 2). A GNC protein with two AgBDs may simultaneously bind to a surface molecule, such as CD3 on a T cell, and a tumor antigen, such as ROR1 on a tumor cell, for re-directing or guiding the T cell to the tumor cell. The addition of the third AgBD, e.g. specifically bind to 41BB, may help enhance anti-CD3-induced T cell activation because 41BB is a co-stimulation factor and the binding stimulates its agonist activity to activated T cells. The addition of the fourth AgBD to a GNC protein, e.g. specifically bind to PD-L1 on a tumor cell, may block the inhibitory pathway of PD-L1 on tumor cells that is mediated through its binding to PD-1 on the T cells. With these basic principles, GNC proteins may be designed and constructed to acquire multiple AgBDs specifically for binding unequal numbers of T cell antagonists and agonists, not only to re-direct activated T cells to tumor cells but also to control their activity in vivo (TABLE 2). Therefore, the design of GNC proteins may be any multi-specific proteins. TABLE 3 provides some example GNC proteins and antibodies with the specificity of antibody binding domains.

In one embodiment, the GNC proteins may include multi-specific antigen binding moieties characterized by two functional groups: Moiety 1 comprises multiple antigen binding domains (AgBD) whose specificities are implicated in T-cell activation, agonist co-stimulation, and/or inhibitory antagonist activity, and Moiety 2 comprises at least one cancer cell binding specificity. GNC proteins may simultaneously bind to a surface molecule, such as CD3 of a T cell, and a tumor antigen, such as ROR1 of a tumor cell, thereby re-directing or guiding the T cell to the tumor cell. An addition of the third binding domain in a GNC protein may help enhance the CD3-induced T cell activation through its direct binding of 41BB, which is a co-stimulation factor exerting agonist activity. Furthermore, an addition of the fourth binding domain in a GNC protein may bind to PD-L1 on the tumor cell to block the inhibitory pathway of PD-L1 on tumor cells that is mediated through its binding to PD-1 on the T cells. In some embodiments, GNC proteins acquire multiple binding capacities to re-direct activated T cells to tumor cells, and multiple binding may help modulate T cell activation through modulating either agonist or antagonist activity or both. Some binding capacities may be similar to that of either the chimeric antigen receptor on a CAR-T cell or a bi-specific antibody, such as the BiTe antibody. Not wanting to be bound by theory, through the interactions of various domains with cytotoxic cell receptors and tumor associated antigen, the GNC proteins may provide significant advantage as a therapeutic agent than traditional cell-based therapeutics (such as CAR-T and antibody therapy) including, without limitation, improved binding efficacy, optimized cellular signaling and cytotoxicity, as well as reduced side effects such as reduced severity of cytokine storm syndrome.

In one embodiment, the application provides an example GNC protein having 4 different binding domains. The GNC protein may a "tetra-specific antibody" with its linkers and backbone comprises antibody fragments. Of the 4 different antigen binding domains, one specifically binds to CD3 on T cells, the second binding domain is specific against a tumor associated antigen, including but not limited to other tumor antigens, such as ROR1, CEA, HER2, EGFR, EGFRvIII, LMP1, LMP2A, Mesothelin, PSMA, EpCAM, glypican-3, gpA33, GD2, TROP2, BCMA, CD19, CD20, CD33, CD123, CD22, CD30, and the third and fourth binding domains are specific against two distinct immune checkpoint modulators, namely, PD-L1, PD-1, OX40, 4-1BB, GITR, TIGIT, TIM-3, LAG-3, CTLA4, CD40, VISTA, ICOS, BTLA, Light, HVEM, CD73, CD39, etc. Because of their definition in function and variety in composition, GNC proteins is classified as a new class of immune-modulators for treating cancer. TABLE 4 shows the list of the example tetra-specific GNC antibodies.

In one embodiment, GNC-mediated immunotherapy may include types of antibody therapy and cell therapy. Herein, the advantages may include, but not limited to, the inclusion of an IgG Fc domain may confer the characteristic of a longer half-life in serum compared to a bi-specific BiTe molecule; second, the inclusion of two binding domains specific for immune checkpoint modulators may inhibit the suppressive pathways and engage the co-stimulatory pathways at the same time; third, that cross-linking CD3 on T cells with tumor associated antigens re-directs and guides T cells to kill the tumor cells without the need of removing T cells from the patient and genetically modifying them to be specific for the tumor cells before re-introducing them back into the patient, also known as chimeric antigen receptor T cells (CAR-T) therapy; and fourth, that GNC protein-mediated antibody therapy or T cell therapy does not involve genetic modification of T cells, the latter of which may carry the risk of transforming modified T cells to clonal expansion, i.e. T cell leukemia.

With one or more addition of the binding capacity, the advantage of GNC protein-mediated immunotherapy over conventional immunotherapies include, but not limited to, first, that inclusion of an IgG Fc domain may confer the characteristic of a longer half-life in serum compared to a bi-specific BiTe molecule; second, that inclusion of two binding domains specific for immune checkpoint modulators may inhibit the suppressive pathways and engage the co-stimulatory pathways at the same time; third, that cross-linking CD3 on T cells with tumor associated antigens re-directs and guides T cells to kill the tumor cells without the need of removing T cells from the patient and genetically modifying them to be specific for the tumor cells before re-introducing them back into the patient, also known as chimeric antigen receptor T cells (CAR-T) therapy; and fourth, that GNC protein-mediated antibody therapy or T cell therapy does not involve genetic modification of T cells, the latter of which may carry the risk of transforming modified T cells to clonal expansion, i.e. T cell leukemia.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

EXAMPLES

While the following examples are provided by way of illustration only and not by way of limitation. Those of skill in the art will readily recognize a variety of non-critical parameters that could be changed or modified to yield essentially the same or similar results.

Example 1: FACS Analysis of Binding of Tetra-Specific GNC Antibody to Human ROR1 Transfected CHO Cells The tetra-specific GNC antibodies listed in TABLEs 3 and 4 were tested for binding to Chinese hamster ovary cells (CHO) cells stably expressing a full-length human ROR1. Antibodies were prepared at 2× final concentration and titrated 1:5 across 3 wells of a 96 well plate in 50 μl of PBS/2% FBS and then 5,000 ROR1-CHO cells in 50 μl PBS/2% FBS were added. This mixture was incubated for 30 minutes on ice, washed once with 200 μl PBS/2% FBS, and then the secondary antibody PE Goat anti-Human IgG Fc at 1:1000 dilution of stock was added, and this mixture was incubated for 30 minutes on ice. Cells were washed 2×200 μl PBS/2% FBS, resuspended in 50 μl PBS/2% FBS and analyzed on a BD LSRFORTESSA and the binding profile is shown in FIG. 4. The tetra-specific antibodies SI-35E18, 19, and 20, with the 323H7 binding domain specific for the Ig domain of ROR1, showed higher binding than the tetra-specific GNC antibodies SI-3521, 22, and 23, with the 338H4 binding domain specific for the frizzled domain of ROR1, and the tetra-specific GNC antibodies SI-3524, 25, and 26, with the 330F11 binding domain specific for the kringle domain of ROR1, did not bind.

Example 2: FACS Analysis of Binding of Tetra-Specific GNC Antibody to Human 41BB Transfected CHO Cells The tetra-specific GNC antibodies listed in TABLEs 3 and 4 were tested for binding to Chinese hamster ovary cells (CHO) cells stably expressing a full-length human ROR1. Antibodies were prepared at 2× final concentration and titrated 1:5 across 3 wells of a 96 well plate in 50 μl of PBS/2% FBS and then 5,000 ROR1-CHO cells in 50 μl PBS/2% FBS were added. This mixture was incubated for 30 minutes on ice, washed once with 200 μl PBS/2% FBS, and then the secondary antibody PE Goat anti-Human IgG Fc at 1:1000 dilution of stock was added, and this mixture was incubated for 30 minutes on ice. Cells were washed 2×200 μl PBS/2% FBS, resuspended in 50 μl PBS/2% FBS and analyzed on a BD LSRFORTESSA and the binding profile is shown in FIG. 5. All of the tetra-specific GNC antibodies except for the control SI-27E12 contain a 41BB binding domain, 460C3, 420H5, or 466F6 and bound to 41BB expressing CHO cells with varying intensity.

Example 3: FACS Analysis of Binding of Tetra-Specific GNC Antibody to Human PDL1 Transfected CHO Cells The tetra-specific GNC antibodies listed in TABLEs 3 and 4 were tested for binding to Chinese hamster ovary cells (CHO) cells stably expressing full length human ROR1. Antibodies were prepared at 2× final concentration and titrated 1:5 across 3 wells of a 96 well plate in 50 μl of PBS/2% FBS and then 5,000 ROR1-CHO cells in 50 μl PBS/2% FBS were added. This mixture was incubated for 30 minutes on ice, washed once with 200 μl PBS/2% FBS, and then the secondary antibody PE Goat anti-Human IgG Fc at 1:1000 dilution of stock was added, and this mixture was incubated for 30 minutes on ice. Cells were washed 2×200 μl PBS/2% FBS, resuspended in 50 μl PBS/2% FBS and analyzed on a BD LSRFORTESSA and the binding profile is shown in FIG. 6. All of the tetra-specific GNC antibodies except for the control SI-27E15 contain the same PDL1 binding domain, PL23006, and showed very similar binding intensity to PDL1 expressing CHO cells.

Example 4: Re-Directed T Cell Cytotoxicity (RTCC) Assay with Peripheral Blood Mononuclear Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human peripheral blood mononuclear cells (PBMC) as effectors. The Kasumi 2 target cells, $5\times10^6$, were labeled with CFSE (Invitrogen, #C34554) at 0.5 μM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 μl of target cells (5,000), 50 μl of PBMC (25,000), and 100 μl of each antibody dilution to each well of the assay. The assay plate was incubated at 37° C. for approximately 72 hours and then the contents of each assay well were harvested and analyzed for the number of CFSE-labeled target cells remaining. As shown on FIG. 7, the tetra-specific GNC antibodies all contain the same PDL1 binding domain PL23006, the same ROR1 binding domain 323H7, and the same CD3 binding domain 284A10, but have one of the 41BB binding domains 460C3, 420H5, and 466F6 and showed greater RTCC activity compared to the controls except for the control SI-27E12 which does not have a 41BB binding domain but appeared to be similarly potent at the tetra-specific GNC antibodies SI-35E18, 19, and 20.

Example 5: Re-Directed T Cell Cytotoxicity (RTCC) Assay with CD8+, CD45RO+ Memory T Cells as Effectors and B-Acute Lymphoblastic Leukemia (B-ALL) Cell Line Kasumi-2 as Targets The tetra-specific GNC antibodies listed in TABLE 3 and 4 were tested for RTCC activity against the B-ALL cell line Kasumi 2 using human CD8+, CD45RO+ memory T cells as effectors. The Kasumi 2 target cells, $5\times10^6$, were labeled with CFSE (Invitrogen, #C34554) at 0.5 μM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human CD8+, CD45RO+ memory T cells were enriched from PBMC from a normal donor using the EasySep™ Human Memory CD8+ T Cell Enrichment Kit (Stemcell Technologies, #19159) as per the manufacturers protocol. The final cell population was determined to be 98% CD8+, CD45RO+ T cells by FACS analysis. In the final destination 96 well plate the target cells, T cells, and serially titrated antibodies were combined by adding 100 μl of target cells (5,000), 50 μl of CD8+, CD45RO+ memory T cells (25,000), and 100 μl of each antibody dilution to each well of the assay. The assay plate was incubated at 37 C for approximately 72 hours and then the contents of each assay well were harvested and analyzed for the number of CFSE-labeled target cells remaining. As shown on FIG. 8, the tetra-specific antibodies all contain the same PDL1 binding domain PL23006, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 6: Re-Directed T Cell Cytotoxicity (RTCC) Assay with CD8+, CD45RA+ Naive T Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human CD8+, CD45RA+ memory T cells as effectors. The Kasumi 2 target cells, 5×10e6, were labeled with CFSE (Invitrogen, #C34554) at 0.5 μM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human CD8+, CD45RA+ memory T cells were enriched from peripheral blood mononuclear cells from a normal donor using the EasySep™ Human Naïve CD8+ T Cell Isolation Kit (Stemcell Technologies, #19258) as per the manufacturers protocol. The final cell population was determined to be 98% CD8+, CD45RA+ T cells by FACS analysis (data not shown). In the final destination 96 well plate the target cells, T cells, and serially titrated antibodies were combined by adding 100 μl of target cells (5,000), 50 μl of CD8+, CD45RO+ T cells (25,000), and 100 μl of each antibody dilution to each well of the assay. The assay plate was incubated at 37 C for approximately 72 hours and then the contents of each assay well were harvested and analyzed for the number of CFSE-labeled target cells remaining. As shown on FIG. 9, all tetra-specific GNC antibodies contain the same PDL1 binding domain PL23006, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 7: Re-Directed T Cell Cytotoxicity (RTCC) Assay with Peripheral Blood Mononuclear Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human peripheral blood mononuclear cells (PBMC) as effectors. The Kasumi 2 target cells, $5\times10^6$, were labeled with CFSE (Invitrogen, #C34554) at 0.5 μM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 μl of target cells (5,000), 50 μl of PBMC (25,000), and 100 μl of each antibody dilution to each well of the assay. The assay plate was incubated at 37° C. for approximately 72 hours and then the contents of each assay well were harvested and analyzed for the number of CFSE-labeled target cells remaining. As shown on FIG. 10, the tetra-specific GNC antibodies all contain the same PDL1 binding domain PL23006, the same ROR1 binding domain 338H4, and the same CD3 binding domain 284A10, but have one of the 41BB binding domains 460C3, 420H5, and 466F6 and showed greater RTCC activity compared to the controls except for the control SI-35E36 which does not have a 41BB binding domain but appeared to be similarly potent at the tetra-specific GNC antibodies SI-35E18, 19, and 20.

Example 8: Re-Directed T Cell Cytotoxicity (RTCC) Assay with CD8+, CD45RO+ Memory T Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human CD8+, CD45RO+ memory T cells as effectors. The Kasumi 2 target cells, $5\times10^6$, were labeled with CFSE (Invitrogen, #C34554) at 0.5 μM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human CD8+, CD45RO+ memory T cells were enriched from PBMC from a normal donor using the EasySep™ Human Memory CD8+ T Cell Enrichment Kit (Stemcell Technologies, #19159) as per the manufacturers protocol. The final cell population was determined to be 98% CD8+, CD45RO+ T cells by FACS analysis (data not shown). In the final destination 96 well plate the target cells, T cells, and serially titrated antibodies were combined by adding 100 μl of target cells (5,000), 50 μl of CD8+, CD45RO+ memory T cells (25,000), and 100 μl of each antibody dilution to each well of the assay. The assay plate was incubated at 37° C. for approximately 72 hours and then the contents of each assay well were harvested and analyzed for the number of CFSE-labeled target cells remaining. As shown on FIG. 11, the tetra-specific GNC antibodies all contain the same PDL1 binding domain PL23006, the same ROR1 binding domain 338H4, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 9: Re-Directed T Cell Cytotoxicity (RTCC) Assay with CD8+, CD45RA+ Naive T Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human CD8+, CD45RA+ memory T cells as effectors. The Kasumi 2 target cells, $5\times10^6$, were labeled with CFSE (Invitrogen, #C34554) at 0.5 M in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 μl of RPMI+10% FBS. Human CD8+, CD45RA+ memory T cells were enriched from PBMC from a normal donor using the EasySep™ Human Naïve CD8+ T Cell Isolation Kit (Stemcell Technologies, #19258) as per the manufacturers protocol. The final cell population was determined to be 98% CD8+, CD45RA+ T cells by FACS analysis. In the final destination 96 well plate the target cells, T cells, and serially titrated antibodies were combined by adding 100 μl of target cells (5,000), 50 μl of CD8+, CD45RO+ T cells (25,000), and 100 l of each antibody dilution to each well of the assay. The assay plate was incubated at 37° C. for approximately 72 hours and then the contents of each assay well were harvested and analyzed for the number of CFSE-labeled target cells remaining. As shown on FIG. 12, the tetra-specific GNC antibodies all contain the same PDL1 binding domain PL23006, the same ROR1 binding domain 338H4, and the same CD3 binding domain 284A10, but have one of the 41BB binding domains 460C3, 420H5, and 466F6 but did not show greater RTCC activity compared to the controls that do not contain one of the 41BB, PDL1, ROR1, or CD3 binding domains. This is in contrast to the tetra-specific GNC antibodies described in Example 6 and shown in FIG. 6 that do show RTCC activity with CD8+, CD45RA+ naïve T cells.

Example 10: Redirected panT Cell Cytotoxicity Against Bladder Cancer Cell Line UM-UC-3-EGFRvIII A set of tetra-specific GNC antibodies listed in TABLE 5 was assessed for their ability to lyse targets cells UM-UC-3-EGFRvIII. PanT cells were isolated with EasySep™ Human Pan T Cell Isolation Kit (Stemcell Technologies). UM-UC-3-EGFRvIII cell line was stably expressing nucleus-localized Red Fluorescent Protein (RFP) delivered via lentiviral transduction (Sartorius). UM-UC-3-EGFRvIII-RFP tumor cells were co-cultured with panT cells. Target cell lysis was assessed with flow cytometry (BD LSR-Fortessa) via counting the number of live targets left in culture after 96 h co-culture with panT cells. The two tetra-specific antibodies, SI-39E18 and SI-39E29, were the most efficacious at target tumor cell lysis (FIG. 13). These two molecules are also composed of adjacent binding domains for CD3 and tumor antigen (TABLE 5).

Example 11: CD8 T Cell Proliferation in Response to Treatment with EGFRvIII Targeting Tetraspecific Antibodies A set of tetra-specific GNC antibodies listed in TABLE 5 was assessed for their ability to stimulate CD8 T cell proliferation in the presence of targets cells UM-UC-3-EGFRvIII. PanT cells were labeled with CellTrace Violet dye (Thermo Fisher Scientific). UM-UC-3-EGFRvIII-RFP tumor cells were co-cultured with panT cells. CD8 T cell proliferation was assessed with flow cytometry (BD LSR-Fortessa) via dilution of the CellTrace Violet dye after 96 h of co-culture. The two tetra-specific GNC antibodies, SI-39E18 and SI-39E29, were the most efficacious at stimulating CD8 T cell proliferation in the presence of target cells (FIG. 14). These two molecules are composed of adjacent binding domains for CD3 and tumor antigen (TABLE 5). Other molecules with the strong T cell stimulatory activity include structures containing adjacent CD3 and PD-L1 domains (TABLE 5).

Example 12: IFNγ Secretion in Response to Treatment with EGFRvIII Targeting Tetraspecific Antibodies A set of tetra-specific GNC antibodies listed in TABLE 5 was assessed for their ability to induce IFNγ secretion by PBMC. PBMC were isolated by Ficoll gradient. PBMC were incubated with the test molecules for 96 h. The supernatants were collected and analyzed for the presence of IFNγ using ELISA (R&D Systems) (FIG. 15). Tetra-specific GNC antibodies with the strongest activity in this study all contained adjacent CD3 and PD-L1 domains (TABLE 5). The least active group has molecules with adjacent CD3 and tumor antigen or 4-1BB domains. The only exception from this group of tetra-specific GNC antibodies is SI-39E18, which contains adjacent CD3 and tumor antigen domains. This molecule stimulates moderate production of IFNγ that is less than the most active group of the molecules with adjacent CD3 and PD-L1 domains, but more than other molecules with a similar structural arrangement. Moderate production of IFNγ might be beneficial for the anti-tumor activity of this agent.

Example 13: Redirected Naïve T Cell Cytotoxicity Against Bladder Cancer Cell Line UM-UC-3-EGFRvIII The tetra-specific GNC antibody, SI-39E18, was tested for its ability to redirect naïve T cells to lyse targets cells UM-UC-3-EGFRvIII. Naïve T cells were isolated with EasySep™ Human Naïve Pan T Cell Isolation Kit (Stemcell Technologies). UM-UC-3-EGFRvIII-RFP tumor cells were co-cultured with naïve or panT cells. Lysis of tumor cells was assessed by counting RFP labeled tumor cell nuclei. Images were acquired on live cell imager IncuCyte (Sartorius). Activity of the antibodies was assessed after 120 hours of incubation. The treatment was tested at lower effector-to-target ratio 2.5-to-1. SI-39E18 was efficacious at redirecting naïve T cells. EC50 was at 22.08 pM for naïve T cells and 0.07 pM for panT cells (FIG. 16).

Example 14: Response of PBMC to Treatment with EGFRvIII Targeting Tetra-Specific GNC Antibodies, Proliferation of CD8 T Cells A set of tetra-specific GNC antibodies listed in TABLE 1 was assessed for their ability to induce CD8 T cell proliferation in the absence of target cells. PBMC were labeled with CellTrace Violet dye (Thermo Fisher Scientific) and cultured for 96 h with the test molecules. CD8 T cell proliferation was assessed with flow cytometry (BD LSRFortessa) via dilution of the CellTrace Violet dye. The most efficacious in this study molecules shared structural similarities (FIG. 17). All these molecules contain adjacent CD3 and PD-L1 domains (TABLE 5).

Example 15. Redirected panT Cell Activity Against Bladder Cancer Cell Line UM-UC-3-EGFRvIII in the Presence of Monocytes A set of tetra-specific GNC antibodies listed in TABLE 5 was assessed for their ability to lyse target cells UM-UC-3-EGFRvIII in the presence of monocytes. Monocytes were isolated from PBMC with EasySep™ Human Monocyte Isolation Kit (Stemcell Technologies). UM-UC-3-EGFRvIII-RFP tumor cells were co-cultured with panT cells and monocytes. Target cell lysis was assessed by counting RFP labeled tumor cell nuclei. Images were acquired on live cell imager IncuCyte (Sartorius). Activity of the antibodies was assessed after 96 hours of incubation. The two tetra-specific GNC antibodies, SI-39E18 and SI-39E29, were the most efficacious at target tumor cell lysis (FIG. 18) together with molecules containing adjacent CD3 and PD-L1 binding domains (TABLE 5).

Example 16. Redirected PBMC Cytotoxicity Against Bladder Cancer Cell Line UM-UC-3-EGFRvIII, Functional Activity of Different 4-1BB Domains and Functional Impact of PD-L1 and 4-1BB Domains Tetra-specific GNC antibodies listed in TABLE 5 were assessed for their ability to redirect PBMC cancer cell line UM-UC-3-EGFRvIII (UM-UC-3-EGFRvIII). UM-UC-3-EGFRvIII-RFP tumor cells were co-cultured with PBMC. Lysis of tumor cells was assessed by counting RFP labeled tumor cell nuclei. Images were acquired on live cell imager IncuCyte (Sartorius). Activity of the antibodies was assessed after 96 hours of incubation. The tetra-specific GNC antibodies with different 4-1BB domains, SI-39E4, SI-39E2 and SI-39E3, showed similar activity (FIG. 19). The tetra-specific GNC antibodies with PD-L1 and 4-1BB domains replaced by silent (not functional) FITC domains, SI-39E1 and SI-39E5, showed reduction in lysis activity. This observation confirms functional contribution of 4-1BB and PD-L1 domains.

Example 17. Granzyme B Production by PBMC in Response to Treatment with EGFRvIII Targeting Tetra-Specific GNC Antibodies, the Effect of AgBD Positions on the Value of EC50

A set of tetra-specific and EGFRvIII-targeting GNC antibodies listed in TABLE 5 was assessed for their ability to induce Granzyme B secretion by PBMC. PBMC were incubated with the test molecules for 96 h. The supernatants were collected and analyzed for the presence of Granzyme B using ELISA (R&D Systems), and the level of Granzyme B was plotted to determine EC50 for each tetra-specific GNC antibody. TABLE 6 lists the structural position of AgBD in each tetra-specific GNC antibody. As shown in TABLE 6, the most active molecules in this study all contained adjacent CD3 and PD-L1 domains and 4-1BB×TAA (EGFRvIII in this study). Such a high level of Granzyme B secretion may not be desirable as the cytotoxicity in vivo may become too high. In this context, next group of molecules, SI-39E29 and SI-39E18, showing modest but at least 20-fold less activities contained adjacent CD3 and TAA (EGFRvIII in this study).

Example 18. Redirected panT Cell Activity Against Kasumi-2 Target Cell Line in Response to Treatment with ROR1 Targeting Tetra-Specific GNC Antibodies A set of tetra-specific GNC antibodies listed in TABLE 7 and SI-35E20 in TABLE 4 was assessed for their ability to lyse target cells Kasumi-2. Kasumi-2 cell line was stably expressing Green Fluorescent Protein (GFP) delivered via lentiviral transduction (Clontech). Kasumi-2 tumor cells were co-cultured with panT cells. Target cell lysis was assessed with flow cytometry (BD LSRFortessa) via counting the number of live targets left in culture after 96 h co-culture with panT cells (FIG. 20). SI-35E20 was characterized as shown in FIG. 4-9. This result shows that the efficacy of SI-35E20-mediated redirected panT cell activity against Kasumi-2 target cell line is comparable.

Example 19. Redirected PBMC T Cell Activity Against Kasumi-2 Target Cell Line in Response to Treatment with CD19 Targeting Tetra-Specific GNC Antibodies A set of tetra-specific GNC antibodies listed in TABLE 8 was assessed for their ability to lyse target cells Kasumi-2. Kasumi-2-GFP tumor cells were co-cultured with PBMC. Target cell lysis was assessed with flow cytometry (BD LSRFortessa) via counting the number of live targets left in culture after 8-days of co-culture with PBMC (FIG. 21). SI-38E17 was among more efficacious molecules in this study.

Example 20. CD8 T Cells Proliferation in Response to Treatment with CD19 Targeting Tetra-Specific GNC Antibodies A set of tetra-specific GNC antibodies listed in TABLE 8 was assessed for their ability to stimulate CD8 T cell proliferation in the presence of targets cells Kasumi-2. PBMC were labeled with CellTrace Violet dye (Thermo Fisher Scientific). Kasumi-2-GFP tumor cells were co-cultured with PBMC. CD8 T cell proliferation was assessed with flow cytometry (BD LSRFortessa) via dilution of the CellTrace Violet dye after 8-days of co-culture. The two tetra-specific GNC antibodies, SI-38E17 and SI-38E41, were the most efficacious at stimulating CD8 T cell proliferation in the presence of target cells (FIG. 22). These two molecules are composed of adjacent binding domains for CD3 and tumor antigen.

Example 21. IFNγ Production by PBMC in Response to Treatment with CD19 Targeting Tetraspecific Antibodies A set of tetra-specific GNC antibodies listed in TABLE 8 was assessed for their ability to induce IFNγ secretion by PBMC in the presence of target cells Kasumi-2. Target cells and PBMC were incubated with the test molecules for 8 days. The supernatants were collected and analyzed for the presence of IFNγ using ELISA (R&D Systems). Molecules containing adjacent CD3 and PD-L1 domains were the most efficacious at inducing IFNγ production by PBMC followed by antibody SI-38E5. SI-38E17 showed moderate activity in this study (FIG. 23).

The term "antibody" is used in the broadest sense and specifically covers single monoclonal antibodies (including agonist and antagonist antibodies), antibody compositions with polyepitopic specificity, as well as antibody fragments (e.g., Fab, F(ab')2, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen-or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (Λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called $\alpha$, delta, epsilon, $\gamma$, and $\mu$, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)). In one embodiment, the "humanized antibody" may be obtained by genetic engineering approach that enables production of affinity-matured humanlike polyclonal antiboies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about 10-4 M, at least about 10-5 M, at least about 10-6 M, at least about 10-7 M, at least about 10-8 M, at least about 10-9, alternatively at least about 10-10 M, at least about 10-11 M, at least about 10-12 M, or greater, where KD refers to a dissociation rate of a particular antibody-antigen interaction. In some embodiments, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000-or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

TABLES

TABLE 1A

Composition of functional moieties (Moiety 1 and Moiety 2) and antigen binding domains in GNC proteins with T cell binding domains.

| Moiety 1 | | | Moiety 2 |
|---|---|---|---|
| Activation of T cells | Agonist receptor | Antagonist receptor | Tumor Antigen |
| CD3 | CD28, 41BB, OX40, GITR, CD40L, ICOS, Light, CD27, CD30 | PDL1, PD1, TIGIT, TIM-3, LAG-3, CTLA4, BTLA, VISTA, PDL2 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 1B

Composition of functional moieties (Moiety 1 and Moiety 2) and antigen binding domains in GNC proteins with NK cell binding domains.

| Moiety 1 | | | Moiety 2 |
|---|---|---|---|
| Activation of NK cell | Agonist receptor | Antagonist receptor | Tumor Antigen |
| CD16, NKG2D, KIR2DS1, KIR2DS2, KIR2DS4, KIR3DS1, NKG2C, NKG2E, NKG2H | NKp30a, NKp30b, NKp46, NKp80, DNAM-1, CD96, CD160, 4-1BB, GITR, CD27, OX-40, CRTAM | KIR2DL1, KIR2DL2, KIR2DL3, KIR3DL1, KIR3DL2, KIR3DL3, NKG2A, NKp30c, TIGIT, SIGLEC7, SIGLEC9, LILR, LAIR-1, KLRG1, PD-1, CTLA-4, CD161 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 1C

Composition of functional moieties (Moiety 1 and Moiety 2) and antigen binding domains in GNC proteins with macrophage binding domains.

| Moiety 1 | | | |
|---|---|---|---|
| Agonist receptor on macrophage | Antagonist receptor onmacrophage | Other surface receptors | Moiety 2 Tumor Antigen |
| TLR2, TLR4, CD16, CD64, CD40, CD80, CD86, TREM-1, TREM-2, ILT-1, ILT-6a, ILT-7, ILT-8, EMR2, Dectin-1, CD69 | CD32b, SIRPα, LAIR-1, VISTA, TIM-3, CD200R, CD300a, CD300f, SIGLEC1, SIGLEC3, SIGLEC5, SIGLEC7, SIGLEC9, ILT-2, ILT-3, ILT-4, ILT-5, LILRB3, LILRB4, DCIR | CSF-1R, LOX-1, CCR2, EPβ, CD163, CR3, DC-SIGN, CD206, SR-A, CD36, MARCO | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 1D

Composition of functional moieties (Moiety 1 and Moiety 2) and antigen binding domains in GNC proteins with DC cell binding domains.

| Moiety 1 | | | Moiety 2 |
|---|---|---|---|
| Agonist receptor on DC | Antagonist receptor on DC | Other surface receptors | Tumor Antigen |
| TLR, CD16, CD64, CD40, CD80, CD86, HVEM,CD70 | VISTA, TIM-3, LAG-3, BTLA | CSF-1R, LOX-1, CCR7, DC-SIGN, GM-CSF-R, IL-4R, IL-10R, CD36, CD206, DCIR, RIG-1, CLEC9A, CXCR4 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 2

Examples of possible combinations of T cell activation, T cell agonist, T cell antagonist, and tumor antigen binding domains in a single GNC protein.

| GNC protein | T Cell activation | Tumor antigen | T Cell antagonist | T Cell agonist | T Cell antagonist | T Cell antagonist | T Cell antagonist | T Cell agonist |
|---|---|---|---|---|---|---|---|---|
| Bi-specific | CD3 | ROR1 | | | | | | |
| Tri-specific | CD3 | ROR1 | PD1 | | | | | |
| Tetra-specific | CD3 | ROR1 | PD1 | 41BB | | | | |
| Penta-specific | CD3 | ROR1 | PD1 | 41BB | LAG3 | | | |
| Hexa-specific | CD3 | ROR1 | PD1 | 41BB | LAG3 | TIM3 | | |
| Hepta-specific | CD3 | ROR1 | PD1 | 41BB | LAG3 | TIM3 | TIGIT | |
| Octa-specific | CD3 | ROR1 | PD1 | 41BB | LAG3 | TIM3 | TIGIT | CD28 |

TABLE 3

Specificity of antibody binding domains used in GNC proteins.

| AgBD Specificity | Antibody Name |
|---|---|
| CD3ε | 284A10 |
| | 480C8 |
| 4-1BB | 460C3 |
| | 420H5 |
| | 466F6 |
| FITC | 4420 |
| PD-L1 | PL230C6 |

TABLE 3-continued

Specificity of antibody binding domains used in GNC proteins.

| AgBD Specificity | Antibody Name |
|---|---|
| CD19 | 21D4 |
| ROR1 IgD Domain | 323H7 |
| Kringle Domain | 330F11 |
| Frizzled Domain | 338H4 |
| | 324C6 |
| EGFRvIII | 806 |

TABLE 4

List of tetra-specific GNC proteins.

| Antibody ID | Domain 1 LH-scFv | Humanized Variant | Domain 2 Fab | Humanized Variant | IgG Fc | Domain 3 LH-scFv | Humanized Variant | Domain 4 LH-scFv | Humanized Variant |
|---|---|---|---|---|---|---|---|---|---|
| SI-35E18 | 460C3 | H1L1 | PL230C6 | H3L3 | n2 | 323H7 | H4L1 | 284A10 | H1L1 |
| SI-35E19 | 420HS | H3L3 | PL230C6 | H3L3 | n2 | 323H7 | H4L1 | 284A10 | H1L1 |
| SI-35E20 | 466F6 | H2L5 | PL230C6 | H3L3 | n2 | 323H7 | H4L1 | 284A10 | H1L1 |
| SI-35E21 | 460C3 | H1L1 | PL230C6 | H3L3 | n2 | 338H4 | H3L4 | 284A10 | H1L1 |
| SI-35E22 | 420H5 | H3L3 | PL230C6 | H3L3 | n2 | 338H4 | H3L4 | 284A10 | H1L1 |
| SI-35E23 | 466F6 | H2L5 | PL230C6 | H3L3 | n2 | 338H4 | H3L4 | 284A10 | H1L1 |
| SI-35E24 | 460C3 | H1L1 | PL230C6 | H3L3 | n2 | 330F11 | H1L1 | 284A10 | H1L1 |
| SI-35E25 | 420H5 | H3L3 | PL230C6 | H3L3 | n2 | 330F11 | H1L1 | 284A10 | H1L1 |
| SI-35E26 | 466F6 | H2L5 | PL230C6 | H3L3 | n2 | 330F11 | H1L1 | 284A10 | H1L1 |
| SI-27E12 | 4420 | — | PL230C6 | H3L3 | n2 | 324C6 | H2L1 | 480C8 | H1L1 |
| SI-27E15 | 460C3 | H1L1 | 4420 | — | n2 | 324C6 | H2L1 | 480C8 | H1L1 |
| SI-27E13 | 460C3 | H1L1 | PL230C6 | H3L3 | n2 | 4420 | — | 480C8 | H1L1 |
| SI-35E2 | 460C3 | H1L1 | PL230C6 | H3L3 | n2 | 324C6 | H2L1 | 4420 | — |

TABLE 5

Tetra-specific GNC antibodies with EGFRvIII tumor antigen binding domain.

| GNC ID | AgBD 1 (LH-scFv) | Humanized Variant | AgBD 2 (Fab) | Humanized Variant | IgG1 Fc | AgBD 3 (HL-scFv) | Humanized Variant | AgBD 4 (HL-scFv) | Humanized Variant |
|---|---|---|---|---|---|---|---|---|---|
| SI-39E01 | PL230C6 | L2H3 | 806 | — | n2 | 284A10 | H1L1 | FITC | — |
| SI-39E02 | PL230C6 | L2H3 | 806 | — | n2 | 284A10 | H1L1 | 460C3 | H1L1 |

TABLE 5-continued

Tetra-specific GNC antibodies with EGFRvIII tumor antigen binding domain.

| GNC ID | AgBD 1 (LH-scFv) | Humanized Variant | AgBD 2 (Fab) | Humanized Variant | IgG1 Fc | AgBD 3 (HL-scFv) | Humanized Variant | AgBD 4 (HL-scFv) | Humanized Variant |
|---|---|---|---|---|---|---|---|---|---|
| SI-39E03 | PL230C6 | L2H3 | 806 | — | n2 | 284A10 | H1L1 | 466F6 | H2L5 |
| SI-39E04 | PL230C6 | L2H3 | 806 | — | n2 | 284A10 | H1L1 | 420H5 | H3L3 |
| SI-39E05 | FITC | — | 806 | — | n2 | 284A10 | H1L1 | 420H5 | H3L3 |
| SI-39E10 | 420H5 | L3H3 | PL230C6 | H3L2 | n2 | 806 | — | 284A10 | H1L1 |
| SI-39E13 | 420H5 | L3H3 | PL230C6 | H3L2 | n2 | 284A10 | H1L1 | 806 | — |
| SI-39E18 | 284A10 | L1H1 | 806 | — | n2 | PL221G5 | H1L1 | 420H5 | H3L3 |
| SI-39E23 | PL230C6 | L2H3 | 806 | — | n2 | 420H5 | H3L3 | 284A10 | H1L1 |
| SI-39E29 | 806 | — | 284A10 | H1L1 | n2 | PL221G5 | H1L1 | 420H5 | H3L3 |
| SI-39E40 | 420H5 | L3H3 | 806 | — | n2 | 284A10 | H1L1 | PL221G5 | H1L1 |
| SI-39E41 | 806 | — | 420H5 | H3L3 | n2 | 284A10 | H1L1 | PL221G5 | H1L1 |
| SI-39E42 | 284A10 | L1H1 | PL230C6 | H3L2 | n2 | 806 | — | 420H5 | H3L3 |
| SI-39E43 | 284A10 | L1H1 | PL230C6 | H3L2 | n2 | 420H5 | H3L3 | 806 | — |
| SI-39E44 | 420H5 | L3H3 | 806 | — | n2 | PL221G5 | H1L1 | 284A10 | H1L1 |
| SI-39E45 | 806 | — | 420H5 | H3L3 | n2 | PL221G5 | H1L1 | 284A10 | H1L1 |
| SI-39E48 | PL230C6 | L2H3 | 284A10 | H1L1 | n2 | 806 | — | 420H5 | H3L3 |
| SI-39E49 | PL230C6 | L2H3 | 284A10 | H1L1 | n2 | 420H5 | H3L3 | 806 | — |

TABLE 6

Granzyme B production by PBMC in response to treatment with EGFRvIII targeting tetra-specific GNC antibodies, the effect of AgBDs on EC50.

| GNC ID | AgBDs D1 × D2 (Fab) | IgG Fc | AgBDs D3 × D4 | Granzyme B secretion EC50 (pM) |
|---|---|---|---|---|
| SI-39E48 | PD-L1 × CD3 | n2 | 4-1BB × TAA (806) | 0.006 |
| SI-39E49 | PD-L1 × CD3 | n2 | TAA (806) × 4-1BB | 0.050 |
| SI-39E43 | CD3 × PD-L1 | n2 | 4-1BB × TAA (806) | 0.163 |
| SI-39E42 | CD3 × PD-L1 | n2 | TAA (806) × 4-1BB | 0.207 |
| SI-39E45 | TAA (806) × 4-1BB | n2 | PD-L1 × CD3 | 0.285 |
| SI-39E44 | 4-1BB × TAA (806) | n2 | PD-L1 × CD3 | 0.345 |
| SI-39E41 | TAA (806) × 4-1BB | n2 | CD3 × PD-L1 | 0.346 |
| SI-39E40 | 4-1BB × TAA (806) | n2 | CD3 × PD-L1 | 0.355 |

TABLE 6-continued

Granzyme B production by PBMC in response to treatment with EGFRvIII targeting tetra-specific GNC antibodies, the effect of AgBDs on EC50.

| GNC ID | AgBDs D1 × D2 (Fab) | IgG Fc | AgBDs D3 × D4 | Granzyme B secretion EC50 (pM) |
|---|---|---|---|---|
| SI-39E29 | TAA (806) × CD3 | n2 | PD-L1 × 4-1BB | 7.797 |
| SI-39E18 | CD3 × TAA (806) | n2 | PD-L1 × 4-1BB | 14.750 |
| SI-39E4 | PD-L1 × TAA (806) | n2 | CD3 × 4-1BB | 21.930 |
| SI-39E13 | 4-1BB × PD-L1 | n2 | CD3 × TAA (806) | 24.700 |
| SI-39E23 | PD-L1 × TAA (806) | n2 | 4-1BB × CD3 | 35.910 |
| SI-39E10 | 4-1BB × PD-L1 | n2 | TAA (806) × CD3 | 61.680 |

TABLE 7

Tetra-specific GNC antibodies with ROR1 tumor antigen binding domain.

| GNC ID | AgBD 1 (LH-scFv) | Humanized Variant | AgBD 2 (Fab) | Humanized Variant | IgG1 Fc | AgBD 3 (HL-scFv) | Humanized Variant | AgBD 4 (HL-scFv) | Humanized Variant |
|---|---|---|---|---|---|---|---|---|---|
| SI-35E50 | 466F6 | L5H2 | PL230C6 | H3L2 | n2 | 284A10 | H1L1 | 323H7 | H4L1 |
| SI-35E53 | PL230C6 | L2H3 | 466F6 | H2L5 | n2 | 284A10 | H1L1 | 323H7 | H4L1 |
| SI-35E56 | 284A10 | L1H1 | 323H7 | H4L1 | n2 | 466F6 | H2L5 | PL23006 | H3L2 |
| SI-35E58 | 284A10 | L1H1 | PL230C6 | H3L2 | n2 | 323H7 | H4L1 | 466F6 | H2L5 |
| SI-35E61 | PL230C6 | L2H3 | 284A10 | H1L1 | n2 | 323H7 | H4L1 | 466F6 | H2L5 |
| SI-35E82 | PL230C6 | L2H3 | 466F6 | H2L5 | n2 | 323H7 | H4L1 | 284A10 | H1L1 |
| SI-35E85 | 466F6 | L5H2 | 323H7 | H4L1 | n2 | PL230C6 | H3L2 | 284A10 | H1L1 |
| SI-35E88 | 284A10 | L1H1 | 323H7 | H4L1 | n2 | PL230C6 | H3L2 | 466F6 | H2L5 |
| SI-35E95 | 466F6 | L5H2 | 323H7 | H4L1 | n2 | 284A10 | H1L1 | PL23006 | H3L2 |
| SI-35E99 | 284A10 | L1H1 | 323H7 | H4L1 | n2 | PL221G5 | H1L1 | 466F6 | H2L5 |

TABLE 8

Tetra-specific GNC antibodies with CD19 tumor antigen binding domain.

| GNC ID | AgBD 1 (LH-scFv) | Humanized Variant | AgBD 2 (Fab) | Humanized Variant | IgG1 Fc | AgBD 3 (HL-scFv) | Humanized Variant | AgBD 4 (HL-scFv) | Humanized Variant |
|---|---|---|---|---|---|---|---|---|---|
| SI-38E05 | 466F6 | L5H2 | PL230C6 | H3L2 | n2 | 284A10 | H1L1 | 21D4 | — |
| SI-38E14 | PL230C6 | L2H3 | 466F6 | H2L5 | n2 | 21D4 | — | 284A10 | H1L1 |
| SI-38E17 | 284A10 | H1L1 | 21D4 | — | n2 | PL221G5 | H1L1 | 466F6 | H2L5 |
| SI-38E20 | 466F6 | L5H2 | 21D4 | — | n2 | 284A10 | H1L1 | PL221G5 | H1L1 |
| SI-38E28 | PL230C6 | L2H3 | 284A10 | H1L1 | n2 | 21D4 | — | 466F6 | H2L5 |

TABLE 8-continued

| Tetra-specific GNC antibodies with CD19 tumor antigen binding domain. | | | | | | | | | |
|---|---|---|---|---|---|---|---|---|---|
| GNC ID | AgBD 1 (LH-scFv) | Humanized Variant | AgBD 2 (Fab) | Humanized Variant | IgG1 Fc | AgBD 3 (HL-scFv) | Humanized Variant | AgBD 4 (HL-scFv) | Humanized Variant |
| SI-38E33 | 21D4 | — | 284A10 | H1L1 | n2 | PL221G5 | H1L1 | 466F6 | H2L5 |
| SI-38E41 | 284A10 | H1L1 | 21D4 | — | n2 | 460C3 | H1L1 | PL221G5 | H1L1 |

GUIDANCE AND NAVIGATION CONTROL PROTEINS AND METHOD OF MAKING AND USING THEREOF SEQUENCE LIST

| SEQ ID | Description |
|---|---|
| 1 | anti-CD3 284A10 VHv1 nt |
| 2 | anti-CD3 284A10 VHv1 aa |
| 3 | anti-CD3 284A10 VLv1 nt |
| 4 | anti-CD3 284A10 VLv1 aa |
| 5 | anti-CD3 480C8 VHv1 nt |
| 6 | anti-CD3 480C8 VHv1 aa |
| 7 | anti-CD3 480C8 VLv1 nt |
| 8 | anti-CD3 480C8 VLv1 aa |
| 9 | anti-PD-L1 PL230C6 VHv3 nt |
| 10 | anti-PD-L1 PL230C6 VHv3 aa |
| 11 | anti-PD-L1 PL230C6 VLv2 nt |
| 12 | anti-PD-L1 PL230C6 VLv2 aa |
| 13 | anti-4-1BB 420H5 VHv3 nt |
| 14 | anti-4-1BB 420H5 VHv3 aa |
| 15 | anti-4-1BB 420H5 VLv3 nt |
| 16 | anti-4-1BB 420H5 VHLv3 aa |
| 17 | anti-4-1BB 466F6 VHv2 nt |
| 18 | anti-4-1BB 466F6 VHv2 aa |
| 19 | anti-4-1BB 466F6 VLv5 nt |
| 20 | anti-4-1BB 466F6 VLv5 aa |
| 21 | anti-4-1BB 460C3 VHv1 nt |
| 22 | anti-4-1BB 460C3 VHv1 aa |
| 23 | anti-4-1BB 460C3 VLv1 nt |
| 24 | anti-4-1BB 460C3 VLv1 aa |
| 25 | anti-ROR1 324C6 VHv2 nt |
| 26 | anti-ROR1 324C6 VHv2 aa |
| 27 | anti-ROR1 324C6 VLv1 nt |
| 28 | anti-ROR1 324C6 VLv1 aa |
| 29 | anti-ROR1 323H7 VHv4 nt |
| 30 | anti-ROR1 323H7 VHv4 aa |
| 31 | anti-ROR1 323H7 VLv1 nt |
| 32 | anti-ROR1 323H7 VLv1 aa |
| 33 | anti-ROR1 338H4 VHv3 nt |
| 34 | anti-ROR1 338H4 VHv3 aa |
| 35 | anti-ROR1 338H4 VLv4 nt |
| 36 | anti-ROR1 338H4 VLv4 aa |
| 37 | anti-ROR1 330F11 VHv1 nt |
| 38 | anti-ROR1 330F11 VHv1 aa |
| 39 | anti-ROR1 330F11 VLv1 nt |
| 40 | anti-ROR1 330F11 VLv1 aa |
| 41 | anti-FITC 4-4-20 VH nt |
| 42 | anti-FITC 4-4-20 VH aa |
| 43 | anti-FITC 4-4-20 VL nt |
| 44 | anti-FITC 4-4-20 VL aa |
| 45 | human IgG1 null2 (G1m-fa with ADCC/CDC null mutations) nt |
| 46 | human IgG1 null2 (G1m-fa with ADCC/CDC null mutations) aa |
| 47 | human Ig Kappa nt |
| 48 | human Ig Kappa aa |
| 49 | SI-35E18 (460C3-L1H1-scFv × PL230C6-Fab × 323H7-H4L1-scFv × 284A10-H1L1-scFv) heavy chain nt |
| 50 | SI-35E18 (460C3-L1H1-scFv × PL230C6-Fab × 323H7-H4L1-scFv × 284A10-H1L1-scFv) heavy chain aa |
| 51 | SI-35E18 (460C3-L1H1-scFv × PL230C6-Fab × 323H7-H4L1-scFv × 284A10-H1L1-scFv) light chain nt |
| 52 | SI-35E18 (460C3-L1H1-scFv × PL230C6-Fab × 323H7-H4L1-scFv × 284A10-H1L1-scFv) light chain aa |
| 53 | anti-CD3 284A10 VHv1b nt |
| 54 | anti-CD3 284A10 VHv1b aa |
| 55 | anti-4-1BB 466F6b VHv2 nt |
| 56 | anti-4-1BB 466F6b VHv2 aa |
| 57 | anti-PD-L1 PL230C6 VHv3b nt |
| 58 | anti-PD-L1 PL230C6 VHv3b aa |
| 59 | anti-huPD-L1 PL221G5 VHv1 nt |
| 60 | anti-huPD-L1 PL221G5 VHv1 aa |
| 61 | anti-huPD-L1 PL221G5 VLv1 nt |
| 62 | anti-huPD-L1 PL221G5 VLv1 aa |
| 63 | anti-huCD19 21D4 VH nt |

-continued

GUIDANCE AND NAVIGATION CONTROL PROTEINS AND METHOD OF MAKING AND USING THEREOF SEQUENCE LIST

| SEQ ID | Description |
|---|---|
| 64 | anti-huCD19 21D4 VH aa |
| 65 | anti-huCD19 21D4 VL nt |
| 66 | anti-huCD19 21D4 VL aa |
| 67 | anti-huEGFRvIII 806 VH nt |
| 68 | anti-huEGFRvIII 806 VH aa |
| 69 | anti-huEGFRvIII 806 VL nt |
| 70 | anti-huEGFRvIII 806 VL aa |
| 71 | GGGGSGGGGSG linker nt |
| 72 | GGGGSGGGGSG linker aa |
| 73 | GGGGSGGGGS linker 01 nt |
| 74 | GGGGSGGGGS linker 01 aa |
| 75 | GGGGSGGGGS linker 02 nt |
| 76 | GGGGSGGGGS linker 02 aa |
| 77 | GGGGSGGGGSGGGGSGGGGS linker nt |
| 78 | GGGGSGGGGSGGGGSGGGGS linker aa |
| 79 | SI-39E18 (284A10-L1H1-scFv × 806-Fab × PL221G5-H1L1-scFv × 420H5-H3L3-scFv) heavy chain nt |
| 80 | SI-39E18 (284A10-L1H1-scFv × 806-Fab × PL221G5-H1L1-scFv × 420H5-H3L3-scFv) heavy chain aa |
| 81 | SI-39E18 (284A10-L1H1-scFv × 806-Fab × PL221G5-H1L1-scFv × 420H5-H3L3-scFv) light chain nt |
| 82 | SI-39E18 (284A10-L1H1-scFv × 806-Fab × PL221G5-H1L1-scFv × 420H5-H3L3-scFv) light chain aa |
| 83 | SI-39E29 (806-LH-scFv × 284A10-Fab × PL221G5-H1L1-scFv × 420H5-H3L3-scFv) heavy chain nt |
| 84 | SI-39E29 (806-LH-scFv × 284A10-Fab × PL221G5-H1L1-scFv × 420H5-H3L3-scFv) heavy chain aa |
| 85 | SI-39E29 (806-LH-scFv × 284A10-Fab × PL221G5-H1L1-scFv × 420H5-H3L3-scFv) light chain nt |
| 86 | SI-39E29 (806-LH-scFv × 284A10-Fab × PL221G5-H1L1-scFv × 420H5-H3L3-scFv) light chain aa |
| 87 | SI-35E20 (466F6-L5H2-scFv × PL230C6-Fab × 323H7-H4L1-scFv × 284A10-H1L1-scFv) heavy chain nt |
| 88 | SI-35E20 (466F6-L5H2-scFv × PL230C6-Fab × 323H7-H4L1-scFv × 284A10-H1L1-scFv) heavy chain aa |
| 89 | SI-35E20 (466F6-L5H2-scFv × PL230C6-Fab × 323H7-H4L1-scFv × 284A10-H1L1-scFv) light chain nt |
| 90 | SI-35E20 (466F6-L5H2-scFv × PL230C6-Fab × 323H7-H4L1-scFv × 284A10-H1L1-scFv) light chain aa |
| 91 | SI-35E58 (284A10-L1H1-scFv × PL230C6-Fab × 323H7-H4L1-scFv × 466F6-H2L5-scFv) heavy chain nt |
| 92 | SI-35E58 (284A10-L1H1-scFv × PL230C6-Fab × 323H7-H4L1-scFv × 466F6-H2L5-scFv) heavy chain aa |
| 93 | SI-35E58 (284A10-L1H1-scFv × PL230C6-Fab × 323H7-H4L1-scFv × 466F6-H2L5-scFv) light chain nt |
| 94 | SI-35E58 (284A10-L1H1-scFv × PL230C6-Fab × 323H7-H4L1-scFv × 466F6-H2L5-scFv) light chain aa |
| 95 | SI-35E88 (284A10-L1H1-scFv × 323H7-Fab × PL230C6-H3L2-scFv × 466F6-H2L5-scFv) heavy chain nt |
| 96 | SI-35E88 (284A10-L1H1-scFv × 323H7-Fab × PL230C6-H3L2-scFv × 466F6-H2L5-scFv) heavy chain aa |
| 97 | SI-35E88 (284A10-L1H1-scFv × 323H7-Fab × PL230C6-H3L2-scFv × 466F6-H2L5-scFv) light chain nt |
| 98 | SI-35E88 (284A10-L1H1-scFv × 323H7-Fab × PL230C6-H3L2-scFv × 466F6-H2L5-scFv) light chain aa |
| 99 | SI-35E99 (284A10-L1H1-scFv × 323H7-Fab × PL221G5-H1L1-scFv × 466F6-H2L5-scFv) heavy chain nt |
| 100 | SI-35E99 (284A10-L1H1-scFv × 323H7-Fab × PL221G5-H1L1-scFv × 466F6-H2L5-scFv) heavy chain aa |
| 101 | SI-35E99 (284A10-L1H1-scFv × 323H7-Fab × PL221G5-H1L1-scFv × 466F6-H2L5-scFv) light chain nt |
| 102 | SI-35E99 (284A10-L1H1-scFv × 323H7-Fab × PL221G5-H1L1-scFv × 466F6-H2L5-scFv) light chain aa |
| 103 | SI-38E17 (284A10-L1H1-scFv × 21D4-Fab × PL221G5-H1L1-scFv × 466F6-H2L5-scFv) heavy chain nt |
| 104 | SI-38E17 (284A10-L1H1-scFv × 21D4-Fab × PL221G5-H1L1-scFv × 466F6-H2L5-scFv) heavy chain aa |
| 105 | SI-38E17 (284A10-L1H1-scFv × 21D4-Fab × PL221G5-H1L1-scFv × 466F6-H2L5-scFv) light chain nt |
| 106 | SI-38E17 (284A10-L1H1-scFv × 21D4-Fab × PL221G5-H1L1-scFv × 466F6-H2L5-scFv) light chain aa |
| 107 | SI-38E33 (21D4-LH-scFv × 284A10-Fab × PL221G5-H1L1-scFv × 466F6-H2L5-scFv) heavy chain nt |
| 108 | SI-38E33 (21D4-LH-scFv × 284A10-Fab × PL221G5-H1L1-scFv × 466F6-H2L5-scFv) heavy chain aa |
| 109 | SI-38E33 (21D4-LH-scFv × 284A10-Fab × PL221G5-H1L1-scFv × 466F6-H2L5-scFv) light chain nt |
| 110 | SI-38E33 (21D4-LH-scFv × 284A10-Fab × PL221G5-H1L1-scFv × 466F6-H2L5-scFv) light chain aa |

What we claim is:

1. A guidance and navigation control (GNC) protein, comprising, a binding domain for a T cell activating receptor, wherein the T cell activating receptor comprises CD3, a binding domain for a tumor associated antigen, wherein the tumor associated antigen comprises EGFRvIII, CD19, or ROR1, a binding domain for an immune checkpoint receptor, wherein the immune checkpoint receptor comprises PD-L1, and a binding domain for a T cell co-stimulating receptor, wherein the T cell co-stimulating receptor comprises 4-1 BB, wherein the binding domain for the tumor associated antigen is not adjacent to the binding domain for the T cell co-stimulating receptor.

2. The guidance and navigation control (GNC) protein of claim 1, wherein the binding domain for the T cell activating receptor is adjacent to the binding domain for the tumor associated antigen (TAA).

3. The guidance and navigation control (GNC) protein of claim 1, wherein the binding domain for a tumor associated antigen has a binding affinity to ROR1 IgD domain, ROR1 Frizzled domain, or ROR1 Kringle domain.

4. The guidance and navigation control (GNC) protein of claim 1, wherein the tumor associated antigen is a receptor on a lung cancer cell, a liver cancer cell, a breast cancer cell, a colorectal cancer cell, an anal cancer cell, a pancreatic cancer cell, a gallbladder cancer cell, a bile duct cancer cell, a head and neck cancer cell, a nasopharyngeal cancer cell, a skin cancer cell, a melanoma cell, an ovarian cancer cell, a prostate cancer cell, a urethral cancer cell, a lung cancer cell, a non-small lung cell cancer cell, a small cell lung cancer cell, a brain tumour cell, a glioma cell, a neuroblastoma cell, an esophageal cancer cell, a gastric cancer cell, a liver cancer cell, a kidney cancer cell, a bladder cancer cell, a cervical cancer cell, an endometrial cancer cell, a thyroid cancer cell, an eye cancer cell, a sarcoma cell, a bone cancer cell, a leukemia cell, a myeloma cell, a lymphoma cell, or a combination thereof.

5. The guidance and navigation control (GNC) protein of claim 1, wherein the protein is a tetra-specific antibody comprising a Fc domain.

6. The guidance and navigation control (GNC) protein of claim 5, wherein the T cell activating receptor comprises CD3, and wherein the binding domain for CD3 is linked to the binding domain for the tumor associated (TAA) antigen through a peptide linker to form a CD3-TAA pair, wherein the peptide linker has length not exceeding 100 amino acids.

7. The guidance and navigation control (GNC) protein of claim 6, wherein the peptide linker has a length not exceeding 20 amino acids.

8. The guidance and navigation control (GNC) protein of claim 6, wherein the peptide linker has a length from about 2 amino acids to about 10 amino acids.

9. The guidance and navigation control (GNC) protein of claim 6, wherein the Fc domain is an IgG Fc domain, and wherein the IgG Fc domain intermediates the CD3-TAA pair and the binding domain for the immune checkpoint receptor.

10. The guidance and navigation control (GNC) protein of claim 1, comprising, 3 complementarity determining regions (CDRs) of SEQ ID NO:18, 3 CDRs of SEQ ID NO:20, 3 CDRs of SEQ ID NO:10, 3 CDRs of SEQ ID NO:12, 3 CDRs of SEQ ID NO: 30, 3 CDRs of SEQ ID NO:32, 3 CDRs of SEQ ID NO:2 and 3 CDRs of SEQ ID NO:4, 3 complementarity determining regions (CDRs) of SEQ ID NO:2, 3 CDRs of SEQ ID NO:4, 3 CDRs of SEQ ID NO:64, 3 CDRs of SEQ ID NO:66, 3 CDRs of SEQ ID NO: 60, 3 CDRs of SEQ ID NO:62, 3 CDRs of SEQ ID NO:18 and 3 CDRs of SEQ ID NO:20, or 3 complementarity determining regions (CDRs) of SEQ ID NO:2, 3 CDRs of SEQ ID NO:4, 3 CDRs of SEQ ID NO:68, 3 CDRs of SEQ ID NO:70, 3 CDRs of SEQ ID NO: 60, 3 CDRs of SEQ ID NO:62, 3 CDRs of SEQ ID NO:14 and 3 CDRs of SEQ ID NO:16.

11. The guidance and navigation control (GNC) protein of claim 6 having a N-terminal and a C-terminal, comprising in tandem from the N-terminal to the C-terminal, the binding domain for CD3, the binding domain for EGFRvIII, IgG Fc domain, the binding domain for PD-L1, and the binding domain for 41-BB.

12. The guidance and navigation control (GNC) protein of claim 11, comprising an amino acid sequence having SEQ ID NO: 80 and 82.

13. The guidance and navigation control (GNC) protein of claim 6 having a N-terminal and a C-terminal, comprising in tandem from the N-terminal to the C-terminal, the binding domain for 4-1BB, the binding domain for PD-L1, IgG Fc domain, the binding domain for ROR1, and the binding domain for CD3.

14. The guidance and navigation control (GNC) protein of claim 13, comprising an amino acid sequence having SEQ ID NO: 88 and 90.

15. The guidance and navigation control (GNC) protein of claim 6 having a N-terminal and a C-terminal, comprising in tandem from the N-terminal to the C-terminal, the binding domain for CD3, the binding domain for CD19, IgG Fc domain, the binding domain for PD-L1, and the binding domain for 4-1BB.

16. The guidance and navigation control (GNC) protein of claim 15, comprising an amino acid sequence having SEQ ID NO: 104 and 106.

17. The GNC protein of claim 1, comprising an amino acid sequence having SEQ ID NO: 50 and 52, SEQ ID NO: 80 and 82, SEQ ID NO: 84 and 86, SEQ ID NO: 88 and 90, SEQ ID NO: 92 and 94, SEQ ID NO: 96 and 98, SEQ ID NO: 100 and 102, SEQ ID NO: 104 and 106, or SEQ ID NO: 108 and 110.

18. A biological complex comprising, a T cell having a T cell activating receptor and a T cell co-stimulating receptor, and the GNC protein of claim 1 bound to the T cell through interaction with the T cell activating receptor, the T cell co-stimulating receptor, or a combination thereof.

19. A biological complex comprising a cancer cell having a tumor associated antigen, and the GNC protein of claim 1 bound to the cancer cell through the interaction with the tumor associated antigen.

20. A biological complex, comprising, a T cell having a T cell activating receptor and a T cell co-stimulating receptor, a cancer cell having a tumor associated antigen, and the GNC protein of claim 1, wherein the GNC protein is bound to the T cell through the interaction with the T cell activating receptor, the T cell co-stimulating receptor, or a combination thereof and wherein the GNC protein is bound to the cancer cell through the interaction with the tumor associated antigen.

21. A pharmaceutical composition, comprising the GNC protein of claim 1, and a pharmaceutically acceptable carrier.

* * * * *

SEQUENCE LISTING

```
<160> NUMBER OF SEQ ID NOS: 110

<210> SEQ ID NO 1
<211> LENGTH: 360
<212> TYPE: DNA
<213> ORGANISM: Artificial Sequence
<220> FEATURE:
<223> OTHER INFORMATION: Synthesized

<400> SEQUENCE: 1

gaggtgcagc tggtggagtc tgggggaggc ttggtccagc ctgggggggtc cctgagactc      60

tcctgtgcag cctctggatt caccatcagt accaatgcaa tgagctgggt ccgccaggct     120

ccagggaagg ggctggagtg gatcggagtc attactggtc gtgatatcac atactacgcg     180

agctgggcga aaggcagatt caccatctcc agagacaatt ccaagaacac gctgtatctt     240

caaatgaaca gcctgagagc cgaggacacg gctgtgtatt actgtgcgcg cgacggtgga     300
```

tcatctgcta ttactagtaa caacatttgg ggccaaggaa ctctggtcac cgtttcttca 360

<210> SEQ ID NO 2
<211> LENGTH: 120
<212> TYPE: PRT
<213> ORGANISM: Artificial Sequence
<220> FEATURE:
<223> OTHER INFORMATION: Synthesized

<400> SEQUENCE: 2

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Ile Ser Thr Asn
20 25 30

Ala Met Ser Trp Val Arg Gln Ala Pro Gly Lys Gly Leu Glu Trp Ile
35 40 45

Gly Val Ile Thr Gly Arg Asp Ile Thr Tyr Tyr Ala Ser Trp Ala Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Gly Gly Ser Ser Ala Ile Thr Ser Asn Asn Ile Trp Gly Gln
100 105 110

Gly Thr Leu Val Thr Val Ser Ser
115 120

<210> SEQ ID NO 3
<211> LENGTH: 336
<212> TYPE: DNA
<213> ORGANISM: Artificial Sequence
<220> FEATURE:
<223> OTHER INFORMATION: Synthesized

<400> SEQUENCE: 3
gacgtcgtga tgacccagtc tccttccacc ctgtctgcat ctgtaggaga cagagtcacc 60
atcaattgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagag ttcactctca ccatcagcag cctgcagcct 240
gatgattttg caacttatta ctgccaaggc tatttttatt ttattagtcg tacttatgta 300
aattctttcg gcggagggac caaggtggag atcaaa 336

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Asp Val Val Met Thr Gln Ser Pro Ser Thr Leu Ser Ala Ser Val Gly
1 5 10 15

Asp Arg Val Thr Ile Asn Cys Gln Ala Ser Glu Ser Ile Ser Ser Trp
20 25 30

Leu Ala Trp Tyr Gln Gln Lys Pro Gly Lys Ala Pro Lys Leu Leu Ile
35 40 45

Tyr Glu Ala Ser Lys Leu Ala Ser Gly Val Pro Ser Arg Phe Ser Gly

-continued 50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gly Tyr Phe Tyr Phe Ile Ser
85 90 95

Arg Thr Tyr Val Asn Ser Phe Gly Gly Gly Thr Lys Val Glu Ile Lys
100 105 110

<210> SEQ ID NO 5
<211> LENGTH: 360
<212> TYPE: DNA
<213> ORGANISM: Artificial Sequence
<220> FEATURE:
<223> OTHER INFORMATION: Synthesized

<400> SEQUENCE: 5
gaggtgcagc tggtggagtc tgggggaggc ttggtccagc ctggggggtc cctgagactc 60
tcctgtgcag cctctggaat cgacctcagt agcaatgcaa tgagctgggt ccgccaggct 120
ccagggaagg ggctggagtg gatcggagtc attactggtc gtgatatcac atactacgcg 180
agctgggcga aaggcagatt caccatctcc agagacaatt ccaagaacac gctgtatctt 240
caaatgaaca gcctgagagc cgaggacacg gctgtgtatt actgtgcgcg cgacggtgga 300
tcatctgcta ttaatagtaa gaacatttgg ggccaaggaa ctctggtcac cgtttcttca 360

<210> SEQ ID NO 6
<211> LENGTH: 120
<212> TYPE: PRT
<213> ORGANISM: Artificial Sequence
<220> FEATURE:
<223> OTHER INFORMATION: Synthesized

<400> SEQUENCE: 6

Glu Val Gln Leu Val Glu Ser Gly Gly Gly Leu Val Gln Pro Gly Gly
1 5 10 15

Ser Leu Arg Leu Ser Cys Ala Ala Ser Gly Ile Asp Leu Ser Ser Asn
20 25 30

Ala Met Ser Trp Val Arg Gln Ala Pro Gly Lys Gly Leu Glu Trp Ile
35 40 45

Gly Val Ile Thr Gly Arg Asp Ile Thr Tyr Tyr Ala Ser Trp Ala Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Gly Gly Ser Ser Ala Ile Asn Ser Lys Asn Ile Trp Gly Gln
100 105 110

Gly Thr Leu Val Thr Val Ser Ser
115 120

<210> SEQ ID NO 7
<211> LENGTH: 336
<212> TYPE: DNA
<213> ORGANISM: Artificial Sequence
<220> FEATURE:
<223> OTHER INFORMATION: Synthesized

<400> SEQUENCE: 7
gacatccaga tgacccagtc tccttccacc ctgtctgcat ctgtaggaga cagagtcacc 60
atcacttgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagag ttcactctca ccatcagcag cctgcagcct 240
gatgattttg caacttatta ctgccaaggc tatttttatt ttattagtcg tacttatgta 300
aatgctttcg gcggagggac caaggtggag atcaaa 336

<210> SEQ ID NO 8
<211> LENGTH: 112
<212> TYPE: PRT
<213> ORGANISM: Artificial Sequence
<220> FEATURE:
<223> OTHER INFORMATION: Synthesized

<400> SEQUENCE: 8

Asp Ile Gln Met Thr Gln Ser Pro Ser Thr Leu Ser Ala Ser Val Gly
1 5 10 15

Asp Arg Val Thr Ile Thr Cys Gln Ala Ser Glu Ser Ile Ser Ser Trp
20 25 30

Leu Ala Trp Tyr Gln Gln Lys Pro Gly Lys Ala Pro Lys Leu Leu Ile
35 40 45

Tyr Glu Ala Ser Lys Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gly Tyr Phe Tyr Phe Ile Ser
85 90 95

Arg Thr Tyr Val Asn Ala Phe Gly Gly Gly Thr Lys Val Glu Ile Lys
100 105 110

<210> SEQ ID NO 9
<211> LENGTH: 345
<212> TYPE: DNA
<213> ORGANISM: Artificial Sequence
<220> FEATURE:
<223> OTHER INFORMATION: Synthesized

<400> SEQUENCE: 9
cagtcggtgg aggagtctgg gggaggcttg gtccagcctg gggggtccct gagactctcc 60
tgtacagcct ctggaatcga ccttaatacc tacgacatga tctgggtccg ccaggctcca 120
ggcaaggggc tagagtgggt tggaatcatt acttatagtg gtagtagata ctacgcgaac 180
tgggcgaaag gccgattcac catctccaaa gacaatacca agaacacggt gtatctgcaa 240
atgaacagcc tgagagctga ggacacggct gtgtattact gtgccagaga ttatatgagt 300
ggttcccact tgtggggcca gggaaccctg gtcaccgtct ctagt 345

<210> SEQ ID NO 10
<211> LENGTH: 115
<212> TYPE: PRT
<213> ORGANISM: Artificial Sequence
<220> FEATURE:
<223> OTHER INFORMATION: Synthesized

<400> SEQUENCE: 10

Gln Ser Val Glu Glu Ser Gly Gly Gly Leu Val Gln Pro Gly Gly Ser
1 5 10 15

Leu Arg Leu Ser Cys Thr Ala Ser Gly Ile Asp Leu Asn Thr Tyr Asp
20 25 30

-continued

```
Met Ile Trp Val Arg Gln Ala Pro Gly Lys Gly Leu Glu Trp Val Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Asp Asn Thr Lys Asn Thr Val Tyr Leu Gln
65                  70                  75                  80

Met Asn Ser Leu Arg Ala Glu Asp Thr Ala Val Tyr Tyr Cys Ala Arg
                85                  90                  95

Asp Tyr Met Ser Gly Ser His Leu Trp Gly Gln Gly Thr Leu Val Thr
            100                 105                 110

Val Ser Ser
        115


<210> SEQ ID NO 11
<211> LENGTH: 330
<212> TYPE: DNA
<213> ORGANISM: Artificial Sequence
<220> FEATURE:
<223> OTHER INFORMATION: Synthesized

<400> SEQUENCE: 11

gcctatgata tgacccagtc tccatcttcc gtgtctgcat ctgtaggaga cagagtcacc      60

atcaagtgtc aggccagtga ggacatttat agcttcttgg cctggtatca gcagaaacca     120

gggaaagccc ctaagctcct gatccattct gcatcctctc tggcatctgg ggtcccatca     180

aggttcagcg gcagtggatc tgggacagat ttcactctca ccatcagcag cctgcagcct     240

gaagattttg caacttacta ttgtcaacag ggttatggta aaaataatgt tgataatgct     300

ttcggcggag ggaccaaggt ggagatcaaa                                      330


<210> SEQ ID NO 12
<211> LENGTH: 110
<212> TYPE: PRT
<213> ORGANISM: Artificial Sequence
<220> FEATURE:
<223> OTHER INFORMATION: Synthesized

<400> SEQUENCE: 12

Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys
            100                 105                 110


<210> SEQ ID NO 13
<211> LENGTH: 360
<212> TYPE: DNA
<213> ORGANISM: Artificial Sequence
<220> FEATURE:
<223> OTHER INFORMATION: Synthesized
```

<400> SEQUENCE: 13

```
cagtcgctgg tggagtctgg gggaggcttg gtacagcctg gggggtccct gagactctcc     60

tgtgcagcct ctggattctc cttcagtagc aactactgga tatgctgggt ccgccaggct    120

ccagggaagg ggctggagtg gatcgcatgc atttatgttg gtagtagtgg tgacacttac    180

tacgcgagct ccgcgaaagg ccggttcacc atctccagag acaattccaa gaacacgctg    240

tatctgcaaa tgaacagcct gagagccgag gacacggccg tatattactg tgcgagagat    300

agtagtagtt attatatgtt taacttgtgg ggccagggaa ccctggtcac cgtctcgagc    360
```

<210> SEQ ID NO 14
<211> LENGTH: 120
<212> TYPE: PRT
<213> ORGANISM: Artificial Sequence
<220> FEATURE:
<223> OTHER INFORMATION: Synthesized

<400> SEQUENCE: 14

```
Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100                 105                 110

Gly Thr Leu Val Thr Val Ser Ser
        115                 120
```

<210> SEQ ID NO 15
<211> LENGTH: 336
<212> TYPE: DNA
<213> ORGANISM: Artificial Sequence
<220> FEATURE:
<223> OTHER INFORMATION: Synthesized

<400> SEQUENCE: 15

```
gcccttgtga tgacccagtc tccttccacc ctgtctgcat ctgtaggaga cagagtcacc     60

atcaattgcc aggccagtga ggacattgat acctatttag cctggtatca gcagaaacca    120

gggaaagccc ctaagctcct gatcttttat gcatccgatc tggcatctgg ggtcccatca    180

aggttcagcg gcagtggatc tgggacagaa ttcactctca ccatcagcag cctgcagcct    240

gatgattttg caacttatta ctgccaaggc ggttactata ctagtagtgc tgatacgagg    300

ggtgctttcg gcggagggac caaggtggag atcaaa                              336
```

<210> SEQ ID NO 16
<211> LENGTH: 112
<212> TYPE: PRT
<213> ORGANISM: Artificial Sequence
<220> FEATURE:
<223> OTHER INFORMATION: Synthesized

<400> SEQUENCE: 16

-continued

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110

<210> SEQ ID NO 17
<211> LENGTH: 345
<212> TYPE: DNA
<213> ORGANISM: Artificial Sequence
<220> FEATURE:
<223> OTHER INFORMATION: Synthesized

<400> SEQUENCE: 17
cggtcgctgg tggagtctgg gggaggcttg gtccagcctg gggggtccct gagactctcc 60
tgtacagcct ctggattcac catcagtagc taccacatgc agtgggtccg ccaggctcca 120
gggaaggggc tggagtacat cggaaccatt agtagtggtg gtaatgtata ctacgcgagc 180
tccgcgagag gcagattcac catctccaga ccctcgtcca agaacacggt ggatcttcaa 240
atgaacagcc tgagagccga ggacacggct gtgtattact gtgcgagaga ctctggttat 300
agtgatccta tgtggggcca gggaaccctg gtcaccgtct cgagc 345

<210> SEQ ID NO 18
<211> LENGTH: 115
<212> TYPE: PRT
<213> ORGANISM: Artificial Sequence
<220> FEATURE:
<223> OTHER INFORMATION: Synthesized

<400> SEQUENCE: 18

Arg Ser Leu Val Glu Ser Gly Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Ser
        115

<210> SEQ ID NO 19
<211> LENGTH: 333
<212> TYPE: DNA
<213> ORGANISM: Artificial Sequence
<220> FEATURE:
<223> OTHER INFORMATION: Synthesized

<400> SEQUENCE: 19
gacgttgtga tgacccagtc tccatcttcc gtgtctgcat ctgtaggaga cagagtcacc 60
atcacctgtc aggccagtca gaacattagg acttacttat cctggtatca gcagaaacca 120
gggaaagccc ctaagctcct gatctatgct gcagccaatc tggcatctgg ggtcccatca 180
aggttcagcg gcagtggatc tgggacagat ttcactctca ccatcagcga cctggagcct 240
ggcgatgctg caacttacta ttgtcagtct acctatcttg gtactgatta tgttggcggt 300
gctttcggcg gagggaccaa ggtggagatc aaa 333

<210> SEQ ID NO 20
<211> LENGTH: 111
<212> TYPE: PRT
<213> ORGANISM: Artificial Sequence
<220> FEATURE:
<223> OTHER INFORMATION: Synthesized

<400> SEQUENCE: 20

Asp Val Val Met Thr Gln Ser Pro Ser Ser Val Ser Ala Ser Val Gly
1 5 10 15

Asp Arg Val Thr Ile Thr Cys Gln Ala Ser Gln Asn Ile Arg Thr Tyr
20 25 30

Leu Ser Trp Tyr Gln Gln Lys Pro Gly Lys Ala Pro Lys Leu Leu Ile
35 40 45

Tyr Ala Ala Ala Asn Leu Ala Ser Gly Val Pro Ser Arg Phe Ser Gly
50 55 60

Ser Gly Ser Gly Thr Asp Phe Thr Leu Thr Ile Ser Asp Leu Glu Pro
65 70 75 80

Gly Asp Ala Ala Thr Tyr Tyr Cys Gln Ser Thr Tyr Leu Gly Thr Asp
85 90 95

Tyr Val Gly Gly Ala Phe Gly Gly Gly Thr Lys Val Glu Ile Lys
100 105 110

<210> SEQ ID NO 21
<211> LENGTH: 345
<212> TYPE: DNA
<213> ORGANISM: Artificial Sequence
<220> FEATURE:
<223> OTHER INFORMATION: Synthesized

<400> SEQUENCE: 21
gaggtgcagc tgttggagtc tgggggaggc ttggtacagc ctggggggtc cctgagactc 60
tcctgtgcag cctctggaat cgacttcagt aggagatact acatgtgctg ggtccgccag 120
gctccaggga aggggctgga gtggatcgca tgcatatata ctggtagccg cgatactcct 180
cactacgcga gctccgcgaa aggccggttc accatctcca gagacaattc caagaacacg 240
ctgtatctgc aaatgaacag cctgagagcc gaggacacgg ccgtatatta ctgtgcgaga 300
gaaggtagcc tgtggggcca gggaaccctg gtcaccgtct cgagc 345

<210> SEQ ID NO 22
<211> LENGTH: 115
<212> TYPE: PRT
<213> ORGANISM: Artificial Sequence
<220> FEATURE:
<223> OTHER INFORMATION: Synthesized

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser
        115

<210> SEQ ID NO 23
<211> LENGTH: 333
<212> TYPE: DNA
<213> ORGANISM: Artificial Sequence
<220> FEATURE:
<223> OTHER INFORMATION: Synthesized

<400> SEQUENCE: 23
gacatccaga tgacccagtc tccttccacc ctgtctgcat ctgtaggaga cagagtcacc     60
atcacttgcc agtccagtca gagtgtttat agtaactggt tctcctggta tcagcagaaa    120
ccagggaaag cccctaagct cctgatctat tctgcatcca ctctggcatc tggggtccca    180
tcaaggttca gcggcagtgg atctgggaca gaattcactc tcaccatcag cagcctgcag    240
cctgatgatt ttgcaactta ttactgcgca ggcggttaca atactgttat tgatactttt    300
gctttcggcg gagggaccaa ggtggagatc aaa                                 333

<210> SEQ ID NO 24
<211> LENGTH: 111
<212> TYPE: PRT
<213> ORGANISM: Artificial Sequence
<220> FEATURE:
<223> OTHER INFORMATION: Synthesized

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys
            100                 105                 110

<210> SEQ ID NO 25
<211> LENGTH: 357
<212> TYPE: DNA
<213> ORGANISM: Artificial Sequence
<220> FEATURE:
<223> OTHER INFORMATION: Synthesized

<400> SEQUENCE: 25
cagtcgctgg tggagtctgg gggaggcttg gtccagcctg gggggtccct gagactctcc     60
tgtactgcct ctggattctc cctcagtagg tactacatga cctgggtccg ccaggctcca    120
gggaaggggc tggagtggat cggaaccatt tatactagtg gtagtacatg gtacgcgagc    180
tggacaaaag gcagattcac catctccaaa gacaatacca agaacacggt ggatcttcaa    240
atgaacagcc tgagagccga ggacacggct gtgtattact gtgcgagatc ctattatggc    300
ggtgataaga ctggtttagg catctggggc cagggaactc tggttaccgt ctcttca       357

<210> SEQ ID NO 26
<211> LENGTH: 119
<212> TYPE: PRT
<213> ORGANISM: Artificial Sequence
<220> FEATURE:
<223> OTHER INFORMATION: Synthesized

<400> SEQUENCE: 26

Gln Ser Leu Val Glu Ser Gly Gly Gly Leu Val Gln Pro Gly Gly Ser
1               5                   10                  15

Leu Arg Leu Ser Cys Thr Ala Ser Gly Phe Ser Leu Ser Arg Tyr Tyr
            20                  25                  30

Met Thr Trp Val Arg Gln Ala Pro Gly Lys Gly Leu Glu Trp Ile Gly
        35                  40                  45

Thr Ile Tyr Thr Ser Gly Ser Thr Trp Tyr Ala Ser Trp Thr Lys Gly
    50                  55                  60

Arg Phe Thr Ile Ser Lys Asp Asn Thr Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Ser Tyr Tyr Gly Gly Asp Lys Thr Gly Leu Gly Ile Trp Gly Gln Gly
            100                 105                 110

Thr Leu Val Thr Val Ser Ser
        115

<210> SEQ ID NO 27
<211> LENGTH: 339
<212> TYPE: DNA
<213> ORGANISM: Artificial Sequence
<220> FEATURE:
<223> OTHER INFORMATION: Synthesized

<400> SEQUENCE: 27
gacatccaga tgacccagtc tccttccacc ctgtctgcat ctgtaggaga cagagtcacc     60
atcacttgcc aggccagtca gagcattgat agttggttat cctggtatca gcagaaacca    120
gggaaagccc ctaagctcct gatctatcag gcatccactc tggcatctgg ggtcccatca    180
aggttcagcg gcagtggatc tgggacagag ttcactctca ccatcagcag cctgcagcct    240
gatgattttg caacttatta ctgccaatct gcttatggtg ttagtggtac tagtagttat    300
ttatatactt tcggcggagg gaccaaggtg gagatcaaa 339

<210> SEQ ID NO 28
<211> LENGTH: 113
<212> TYPE: PRT
<213> ORGANISM: Artificial Sequence
<220> FEATURE:
<223> OTHER INFORMATION: Synthesized

<400> SEQUENCE: 28

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Ala Tyr Gly Val Ser Gly
                85                  90                  95

Thr Ser Ser Tyr Leu Tyr Thr Phe Gly Gly Gly Thr Lys Val Glu Ile
            100                 105                 110

Lys
```

<210> SEQ ID NO 29
<211> LENGTH: 366
<212> TYPE: DNA
<213> ORGANISM: Artificial Sequence
<220> FEATURE:
<223> OTHER INFORMATION: Synthesized

<400> SEQUENCE: 29

```
gaggtgcagc tgttggagtc tgggggaggc ttggtacagc ctggggggtc cctgagactc     60

tcctgtgcag cctctggatt caccatcagt cgctaccaca tgacttgggt ccgccaggct    120

ccagggaagg ggctggagtg gatcggacat atttatgtta ataatgatga cacagactac    180

gcgagctccg cgaaaggccg gttcaccatc tccagagaca attccaagaa cacgctgtat    240

ctgcaaatga acagcctgag agccgaggac acggccacct atttctgtgc gagattggat    300

gttggtggtg gtggtgctta tattggggac atctggggcc agggaactct ggttaccgtc    360

tcttca                                                               366
```

<210> SEQ ID NO 30
<211> LENGTH: 122
<212> TYPE: PRT
<213> ORGANISM: Artificial Sequence
<220> FEATURE:
<223> OTHER INFORMATION: Synthesized

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Ser Ala
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Phe Cys
                85                  90                  95

Ala Arg Leu Asp Val Gly Gly Gly Gly Ala Tyr Ile Gly Asp Ile Trp
            100                 105                 110

Gly Gln Gly Thr Leu Val Thr Val Ser Ser
        115                 120


<210> SEQ ID NO 31
<211> LENGTH: 339
<212> TYPE: DNA
<213> ORGANISM: Artificial Sequence
<220> FEATURE:
<223> OTHER INFORMATION: Synthesized

<400> SEQUENCE: 31

gacatccaga tgacccagtc tccatcctcc ctgtctgcat ctgtaggaga cagagtcacc     60

atcacttgcc agtccagtca gagtgtttat aacaacaacg acttagcctg gtatcagcag    120

aaaccaggga aagttcctaa gctcctgatc tattatgctt ccactctggc atctggggtc    180

ccatctcggt tcagtggcag tggatctggg acagatttca ctctcaccat cagcagcctg    240

cagcctgaag atgttgcaac ttattactgt gcaggcggtt atgatacgga tggtcttgat    300

acgtttgctt tcggcggagg gaccaaggtg gagatcaaa                           339


<210> SEQ ID NO 32
<211> LENGTH: 113
<212> TYPE: PRT
<213> ORGANISM: Artificial Sequence
<220> FEATURE:
<223> OTHER INFORMATION: Synthesized

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Asp Thr
                85                  90                  95

Asp Gly Leu Asp Thr Phe Ala Phe Gly Gly Gly Thr Lys Val Glu Ile
            100                 105                 110

Lys


<210> SEQ ID NO 33
<211> LENGTH: 345
<212> TYPE: DNA
<213> ORGANISM: Artificial Sequence
<220> FEATURE:
<223> OTHER INFORMATION: Synthesized

<400> SEQUENCE: 33
```

-continued

```
gaggtgcagc tggtggagtc tgggggaggc ttggtccagc ctggggggtc cctgagactc      60

tcctgtactg cctctggatt ctccctcagt agctatgcaa tgagctgggt ccgccaggct     120

ccagggaggg ggctggagtg gatcggaatc atttatgcta gtggtagcac atactacgcg     180

agctcggcga aaggcagatt caccatctcc aaagacaata ccaagaacac ggtggatctt     240

caaatgaaca gcctgagagc cgaggacacg gctgtgtatt actgtgcgag aatttatgac     300

ggcatggacc tctggggcca gggaactctg gttaccgtct cttca                     345
```

<210> SEQ ID NO 34
<211> LENGTH: 115
<212> TYPE: PRT
<213> ORGANISM: Artificial Sequence
<220> FEATURE:
<223> OTHER INFORMATION: Synthesized

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser
        115
```

<210> SEQ ID NO 35
<211> LENGTH: 321
<212> TYPE: DNA
<213> ORGANISM: Artificial Sequence
<220> FEATURE:
<223> OTHER INFORMATION: Synthesized

<400> SEQUENCE: 35

```
gacatccaga tgacccagtc tccatcctcc ctgtctgcat ctgtaggaga cagagtcacc      60

atcaattgcc aggccagtca gaacatttac agctacttat cctggtatca gcagaaacca     120

gggaaagttc ctaagcgcct gatctatctg gcatctactc tggcatctgg ggtcccatct     180

cggttcagtg gcagtggatc tgggacagat tacactctca ccatcagcag cctgcagcct     240

gaagatgttg caacttatta ctgtcaaagc aattataacg gtaattatgg tttcggcgga     300

gggaccaagg tggagatcaa a                                               321
```

<210> SEQ ID NO 36
<211> LENGTH: 107
<212> TYPE: PRT
<213> ORGANISM: Artificial Sequence
<220> FEATURE:
<223> OTHER INFORMATION: Synthesized

<400> SEQUENCE: 36

```
Asp Ile Gln Met Thr Gln Ser Pro Ser Ser Leu Ser Ala Ser Val Gly
```

-continued

```
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Ser Asn Tyr Asn Gly Asn Tyr
                85                  90                  95

Gly Phe Gly Gly Gly Thr Lys Val Glu Ile Lys
            100                 105
```

<210> SEQ ID NO 37
<211> LENGTH: 360
<212> TYPE: DNA
<213> ORGANISM: Artificial Sequence
<220> FEATURE:
<223> OTHER INFORMATION: Synthesized

<400> SEQUENCE: 37

```
gaggtgcagc tggtggagtc tgggggaggc ttggtccagc ctggggggtc cctgagactc     60

tcctgtgcag cctctggatt ctccctcaat aactactgga tgagctgggt ccgccaggct    120

ccagggaagg ggctggagtg gatcggaacc attagtagtg gtgcgtatac atggttcgcc    180

acctgggcga caggcagatt caccatctcc agagacaatt ccaagaacac gctgtatctt    240

caaatgaaca gcctgagagc cgaggacacg gctgtgtatt actgtgcgag atattcttct    300

actactgatt ggacctactt taacatctgg ggccagggaa ctctggttac cgtctcttca    360
```

<210> SEQ ID NO 38
<211> LENGTH: 120
<212> TYPE: PRT
<213> ORGANISM: Artificial Sequence
<220> FEATURE:
<223> OTHER INFORMATION: Synthesized

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Trp Met Ser Trp Val Arg Gln Ala Pro Gly Lys Gly Leu Glu Trp Ile
        35                  40                  45

Gly Thr Ile Ser Ser Gly Ala Tyr Thr Trp Phe Ala Thr Trp Ala Thr
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Ser Ser Thr Thr Asp Trp Thr Tyr Phe Asn Ile Trp Gly Gln
            100                 105                 110

Gly Thr Leu Val Thr Val Ser Ser
        115                 120
```

<210> SEQ ID NO 39
<211> LENGTH: 324

<212> TYPE: DNA
<213> ORGANISM: Artificial Sequence
<220> FEATURE:
<223> OTHER INFORMATION: Synthesized

<400> SEQUENCE: 39
gacatccaga tgacccagtc tccttccacc ctgtctgcat ctgtaggaga cagagtcacc 60
atcacttgcc aggccagtca gagcattaat aactacttag cctggtatca gcagaaacca 120
gggaaagccc ctaagctcct gatctatagg gcatccactc tggaatctgg ggtcccatca 180
aggttcagcg gcagtggatc tgggacagaa ttcactctca ccatcagcag cctgcagcct 240
gatgattttg caacttatta ctgccaaagc tataatggtg ttggtaggac tgctttcggc 300
ggagggacca aggtggagat caaa 324

<210> SEQ ID NO 40
<211> LENGTH: 108
<212> TYPE: PRT
<213> ORGANISM: Artificial Sequence
<220> FEATURE:
<223> OTHER INFORMATION: Synthesized

<400> SEQUENCE: 40

Asp Ile Gln Met Thr Gln Ser Pro Ser Thr Leu Ser Ala Ser Val Gly
1 5 10 15

Asp Arg Val Thr Ile Thr Cys Gln Ala Ser Gln Ser Ile Asn Asn Tyr
20 25 30

Leu Ala Trp Tyr Gln Gln Lys Pro Gly Lys Ala Pro Lys Leu Leu Ile
35 40 45

Tyr Arg Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Ser Tyr Asn Gly Val Gly Arg
85 90 95

Thr Ala Phe Gly Gly Gly Thr Lys Val Glu Ile Lys
100 105

<210> SEQ ID NO 41
<211> LENGTH: 354
<212> TYPE: DNA
<213> ORGANISM: Artificial Sequence
<220> FEATURE:
<223> OTHER INFORMATION: Synthesized

<400> SEQUENCE: 41
gaggtgaagc tggatgagac tggaggaggc ttggtgcaac ctgggaggcc catgaaactc 60
tcctgtgttg cctctggatt cacttttagt gactactgga tgaactgggt ccgccagtct 120
ccagagaaag gactggagtg ggtagcacaa attagaaaca aaccttataa ttatgaaaca 180
tattattcag attctgtgaa aggcagattc accatctcaa gagatgattc caaaagtagt 240
gtctacctgc aaatgaacaa cttaagagtt gaagacatgg gtatctatta ctgtacgggt 300
tcttactatg gtatggacta ctggggtcaa ggaacctcag tcaccgtctc ctca 354

<210> SEQ ID NO 42
<211> LENGTH: 118
<212> TYPE: PRT
<213> ORGANISM: Artificial Sequence
<220> FEATURE:
<223> OTHER INFORMATION: Synthesized

<400> SEQUENCE: 42

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

<210> SEQ ID NO 43
<211> LENGTH: 336
<212> TYPE: DNA
<213> ORGANISM: Artificial Sequence
<220> FEATURE:
<223> OTHER INFORMATION: Synthesized

<400> SEQUENCE: 43
gatgtcgtga tgacccaaac tccactctcc ctgcctgtca gtcttggaga tcaagcctcc      60
atctcttgca gatctagtca gagccttgta cacagtaatg gaaacaccta tttacgttgg     120
tacctgcaga agccaggcca gtctccaaag gtcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaa                               336

<210> SEQ ID NO 44
<211> LENGTH: 112
<212> TYPE: PRT
<213> ORGANISM: Artificial Sequence
<220> FEATURE:
<223> OTHER INFORMATION: Synthesized

<400> SEQUENCE: 44

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 45
<211> LENGTH: 987
<212> TYPE: DNA
<213> ORGANISM: Artificial Sequence
<220> FEATURE:
<223> OTHER INFORMATION: Synthesized

<400> SEQUENCE: 45

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaagc cgcgggggca    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcgcggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctat agcaagctca ccgtggacaa gagcaggtgg    900

cagcagggga acgtcttctc atgctccgtg atgcatgagg ctctgcacaa ccactacacg    960

cagaagagcc tctccctgtc tccgggt                                         987
```

<210> SEQ ID NO 46
<211> LENGTH: 329
<212> TYPE: PRT
<213> ORGANISM: Artificial Sequence
<220> FEATURE:
<223> OTHER INFORMATION: Synthesized

<400> SEQUENCE: 46

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 47
<211> LENGTH: 321
<212> TYPE: DNA
<213> ORGANISM: Artificial Sequence
<220> FEATURE:
<223> OTHER INFORMATION: Synthesized

<400> SEQUENCE: 47

cgtacggtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagctcgcc cgtcacaaag     300

agcttcaaca ggggagagtg t                                               321


<210> SEQ ID NO 48
<211> LENGTH: 107
<212> TYPE: PRT
<213> ORGANISM: Artificial Sequence
<220> FEATURE:
<223> OTHER INFORMATION: Synthesized

<400> SEQUENCE: 48

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 49
<211> LENGTH: 3681
<212> TYPE: DNA
<213> ORGANISM: Artificial Sequence
<220> FEATURE:
<223> OTHER INFORMATION: Synthesized

<400> SEQUENCE: 49
gacatccaga tgacccagtc tccttccacc ctgtctgcat ctgtaggaga cagagtcacc 60
atcacttgcc agtccagtca gagtgtttat agtaactggt tctcctggta tcagcagaaa 120
ccagggaaag cccctaagct cctgatctat tctgcatcca ctctggcatc tggggtccca 180
tcaaggttca gcggcagtgg atctgggaca gaattcactc tcaccatcag cagcctgcag 240
cctgatgatt ttgcaactta ttactgcgca ggcggttaca atactgttat tgatactttt 300
gctttcggcg gagggaccaa ggtggagatc aaaggcggtg gcggtagtgg gggaggcggt 360
tctggcggcg gagggtccgg cggtggagga tcagaggtgc agctgttgga gtctggggga 420
ggcttggtac agcctggggg gtccctgaga ctctcctgtg cagcctctgg aatcgacttc 480
agtaggagat actacatgtg ctgggtccgc caggctccag ggaaggggct ggagtggatc 540
gcatgcatat atactggtag ccgcgatact cctcactacg cgagctccgc gaaaggccgg 600
ttcaccatct ccagagacaa ttccaagaac acgctgtatc tgcaaatgaa cagcctgaga 660
gccgaggaca cggccgtata ttactgtgcg agagaaggta gcctgtgggg ccagggaacc 720
ctggtcaccg tctcgagcgg cggtggaggg tccggcggtg gtggatccca gtcggtggag 780
gagtctgggg gaggcttggt ccagcctggg gggtccctga gactctcctg tacagcctct 840
ggaatcgacc ttaataccta cgacatgatc tgggtccgcc aggctccagg caaggggcta 900
gagtgggttg gaatcattac ttatagtggt agtagatact acgcgaactg ggcgaaaggc 960
cgattcacca tctccaaaga caataccaag aacacggtgt atctgcaaat gaacagcctg 1020
agagctgagg acacggctgt gtattactgt gccagagatt atatgagtgg ttcccacttg 1080
tggggccagg gaaccctggt caccgtctct agtgctagca ccaagggccc atcggtcttc 1140
cccctggcac cctcctccaa gagcacctct gggggcacag cggccctggg ctgcctggtc 1200
aaggactact tccccgaacc ggtgacggtg tcgtggaact caggcgccct gaccagcggc 1260
gtgcacacct tcccggctgt cctacagtcc tcaggactct actccctcag cagcgtggtg 1320
accgtgccct ccagcagctt gggcacccag acctacatct gcaacgtgaa tcacaagccc 1380
agcaacacca aggtggacaa gagagttgag cccaaatctt gtgacaaaac tcacacatgc 1440
ccaccgtgcc cagcacctga agccgcgggg gcaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680

```
accgtcctgc accaggactg gctgaatggc aaggagtaca agtgcgcggt ctccaacaaa   1740
gccctcccag cccccatcga gaaaaccatc tccaaagcca aagggcagcc ccgagaacca   1800
caggtgtata ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgctggact ccgacggctc cttcttcctc   1980
tatagcaagc tcaccgtgga caagagcagg tggcagcagg ggaacgtctt ctcatgctcc   2040
gtgatgcatg aggctctgca caaccactac acgcagaaga gcctctccct gtctccgggt   2100
ggcggtggag ggtccggcgg tggtggatcc gaggtgcagc tgttggagtc tgggggaggc   2160
ttggtacagc ctggggggtc cctgagactc tcctgtgcag cctctggatt caccatcagt   2220
cgctaccaca tgacttgggt ccgccaggct ccagggaagg ggctggagtg gatcggacat   2280
atttatgtta ataatgatga cacagactac gcgagctccg cgaaaggccg gttcaccatc   2340
tccagagaca attccaagaa cacgctgtat ctgcaaatga acagcctgag agccgaggac   2400
acggccacct atttctgtgc gagattggat gttggtggtg gtggtgctta tattggggac   2460
atctggggcc agggaactct ggttaccgtc tcttcaggcg gtggcggtag tgggggaggc   2520
ggttctggcg gcggagggtc cggcggtgga ggatcagaca tccagatgac ccagtctcca   2580
tcctccctgt ctgcatctgt aggagacaga gtcaccatca cttgccagtc cagtcagagt   2640
gtttataaca acaacgactt agcctggtat cagcagaaac cagggaaagt tcctaagctc   2700
ctgatctatt atgcttccac tctggcatct ggggtcccat ctcggttcag tggcagtgga   2760
tctgggacag atttcactct caccatcagc agcctgcagc ctgaagatgt tgcaacttat   2820
tactgtgcag gcggttatga tacggatggt cttgatacgt ttgctttcgg cggagggacc   2880
aaggtggaga tcaaaggcgg tggagggtcc ggcggtggtg gatccgaggt gcagctggtg   2940
gagtctgggg gaggcttggt ccagcctggg gggtccctga gactctcctg tgcagcctct   3000
ggattcacca tcagtaccaa tgcaatgagc tgggtccgcc aggctccagg gaaggggctg   3060
gagtggatcg gagtcattac tggtcgtgat atcacatact acgcgagctg ggcgaaaggc   3120
agattcacca tctccagaga caattccaag aacacgctgt atcttcaaat gaacagcctg   3180
agagccgagg acacggctgt gtattactgt gcgcgcgacg gtggatcatc tgctattact   3240
agtaacaaca tttggggcca aggaactctg gtcaccgttt cttcaggcgg tggcggtagt   3300
gggggaggcg gttctggcgg cggagggtcc ggcggtggag gatcagacgt cgtgatgacc   3360
cagtctcctt ccaccctgtc tgcatctgta ggagacagag tcaccatcaa ttgccaagcc   3420
agtgagagca ttagcagttg gttagcctgg tatcagcaga aaccagggaa agcccctaag   3480
ctcctgatct atgaagcatc caaactggca tctggggtcc catcaaggtt cagcggcagt   3540
ggatctggga cagagttcac tctcaccatc agcagcctgc agcctgatga ttttgcaact   3600
tattactgcc aaggctattt ttattttatt agtcgtactt atgtaaattc tttcggcgga   3660
gggaccaagg tggagatcaa a                                              3681
```

<210> SEQ ID NO 50
<211> LENGTH: 1227
<212> TYPE: PRT
<213> ORGANISM: Artificial Sequence
<220> FEATURE:
<223> OTHER INFORMATION: Synthesized

<400> SEQUENCE: 50

Asp Ile Gln Met Thr Gln Ser Pro Ser Thr Leu Ser Ala Ser Val Gly

-continued

```
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Ile Asp Phe
145                 150                 155                 160

Ser Arg Arg Tyr Tyr Met Cys Trp Val Arg Gln Ala Pro Gly Lys Gly
                165                 170                 175

Leu Glu Trp Ile Ala Cys Ile Tyr Thr Gly Ser Arg Asp Thr Pro His
            180                 185                 190

Tyr Ala Ser Ser Ala Lys Gly Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Arg Glu Gly Ser Leu Trp Gly Gln Gly Thr
225                 230                 235                 240

Leu Val Thr Val Ser Ser Gly Gly Gly Gly Ser Gly Gly Gly Gly Ser
                245                 250                 255

Gln Ser Val Glu Glu Ser Gly Gly Gly Leu Val Gln Pro Gly Gly Ser
            260                 265                 270

Leu Arg Leu Ser Cys Thr Ala Ser Gly Ile Asp Leu Asn Thr Tyr Asp
        275                 280                 285

Met Ile Trp Val Arg Gln Ala Pro Gly Lys Gly Leu Glu Trp Val Gly
    290                 295                 300

Ile Ile Thr Tyr Ser Gly Ser Arg Tyr Tyr Ala Asn Trp Ala Lys Gly
305                 310                 315                 320

Arg Phe Thr Ile Ser Lys Asp Asn Thr Lys Asn Thr Val Tyr Leu Gln
                325                 330                 335

Met Asn Ser Leu Arg Ala Glu Asp Thr Ala Val Tyr Tyr Cys Ala Arg
            340                 345                 350

Asp Tyr Met Ser Gly Ser His Leu Trp Gly Gln Gly Thr Leu Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430
```

```
Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Ala Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Ala
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Gly Gly Gly Gly
    690                 695                 700

Ser Gly Gly Gly Gly Ser Glu Val Gln Leu Leu Glu Ser Gly Gly Gly
705                 710                 715                 720

Leu Val Gln Pro Gly Gly Ser Leu Arg Leu Ser Cys Ala Ala Ser Gly
                725                 730                 735

Phe Thr Ile Ser Arg Tyr His Met Thr Trp Val Arg Gln Ala Pro Gly
            740                 745                 750

Lys Gly Leu Glu Trp Ile Gly His Ile Tyr Val Asn Asn Asp Asp Thr
        755                 760                 765

Asp Tyr Ala Ser Ser Ala Lys Gly Arg Phe Thr Ile Ser Arg Asp Asn
    770                 775                 780

Ser Lys Asn Thr Leu Tyr Leu Gln Met Asn Ser Leu Arg Ala Glu Asp
785                 790                 795                 800

Thr Ala Thr Tyr Phe Cys Ala Arg Leu Asp Val Gly Gly Gly Gly Ala
                805                 810                 815

Tyr Ile Gly Asp Ile Trp Gly Gln Gly Thr Leu Val Thr Val Ser Ser
            820                 825                 830

Gly Gly Gly Gly Ser Gly Gly Gly Gly Ser Gly Gly Gly Gly Ser Gly
        835                 840                 845
```

```
Gly Gly Gly Ser Asp Ile Gln Met Thr Gln Ser Pro Ser Ser Leu Ser
    850                 855                 860

Ala Ser Val Gly Asp Arg Val Thr Ile Thr Cys Gln Ser Ser Gln Ser
865                 870                 875                 880

Val Tyr Asn Asn Asn Asp Leu Ala Trp Tyr Gln Gln Lys Pro Gly Lys
                885                 890                 895

Val Pro Lys Leu Leu Ile Tyr Tyr Ala Ser Thr Leu Ala Ser Gly Val
            900                 905                 910

Pro Ser Arg Phe Ser Gly Ser Gly Ser Gly Thr Asp Phe Thr Leu Thr
        915                 920                 925

Ile Ser Ser Leu Gln Pro Glu Asp Val Ala Thr Tyr Tyr Cys Ala Gly
    930                 935                 940

Gly Tyr Asp Thr Asp Gly Leu Asp Thr Phe Ala Phe Gly Gly Gly Thr
945                 950                 955                 960

Lys Val Glu Ile Lys Gly Gly Gly Gly Ser Gly Gly Gly Gly Ser Glu
                965                 970                 975

Val Gln Leu Val Glu Ser Gly Gly Gly Leu Val Gln Pro Gly Gly Ser
            980                 985                 990

Leu Arg Leu Ser Cys Ala Ala Ser  Gly Phe Thr Ile Ser  Thr Asn Ala
        995                 1000                1005

Met Ser  Trp Val Arg Gln Ala  Pro Gly Lys Gly Leu  Glu Trp Ile
    1010                 1015                 1020

Gly Val  Ile Thr Gly Arg Asp  Ile Thr Tyr Tyr Ala  Ser Trp Ala
    1025                 1030                 1035

Lys Gly  Arg Phe Thr Ile Ser  Arg Asp Asn Ser Lys  Asn Thr Leu
    1040                 1045                 1050

Tyr Leu  Gln Met Asn Ser Leu  Arg Ala Glu Asp Thr  Ala Val Tyr
    1055                 1060                 1065

Tyr Cys  Ala Arg Asp Gly Gly  Ser Ser Ala Ile Thr  Ser Asn Asn
    1070                 1075                 1080

Ile Trp  Gly Gln Gly Thr Leu  Val Thr Val Ser Ser  Gly Gly Gly
    1085                 1090                 1095

Gly Ser  Gly Gly Gly Gly Ser  Gly Gly Gly Gly Ser  Gly Gly Gly
    1100                 1105                 1110

Gly Ser  Asp Val Val Met Thr  Gln Ser Pro Ser Thr  Leu Ser Ala
    1115                 1120                 1125

Ser Val  Gly Asp Arg Val Thr  Ile Asn Cys Gln Ala  Ser Glu Ser
    1130                 1135                 1140

Ile Ser  Ser Trp Leu Ala Trp  Tyr Gln Gln Lys Pro  Gly Lys Ala
    1145                 1150                 1155

Pro Lys  Leu Leu Ile Tyr Glu  Ala Ser Lys Leu Ala  Ser Gly Val
    1160                 1165                 1170

Pro Ser  Arg Phe Ser Gly Ser  Gly Ser Gly Thr Glu  Phe Thr Leu
    1175                 1180                 1185

Thr Ile  Ser Ser Leu Gln Pro  Asp Asp Phe Ala Thr  Tyr Tyr Cys
    1190                 1195                 1200

Gln Gly  Tyr Phe Tyr Phe Ile  Ser Arg Thr Tyr Val  Asn Ser Phe
    1205                 1210                 1215

Gly Gly  Gly Thr Lys Val Glu  Ile Lys
    1220                 1225
```

<210> SEQ ID NO 51
<211> LENGTH: 651
<212> TYPE: DNA

-continued

<213> ORGANISM: Artificial Sequence
<220> FEATURE:
<223> OTHER INFORMATION: Synthesized

<400> SEQUENCE: 51
gcctatgata tgacccagtc tccatcttcc gtgtctgcat ctgtaggaga cagagtcacc 60
atcaagtgtc aggccagtga ggacatttat agcttcttgg cctggtatca gcagaaacca 120
gggaaagccc ctaagctcct gatccattct gcatcctctc tggcatctgg ggtcccatca 180
aggttcagcg gcagtggatc tgggacagat ttcactctca ccatcagcag cctgcagcct 240
gaagattttg caacttacta ttgtcaacag ggttatggta aaaataatgt tgataatgct 300
ttcggcggag ggaccaaggt ggagatcaaa cgtacggtgg ctgcaccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 52
<211> LENGTH: 217
<212> TYPE: PRT
<213> ORGANISM: Artificial Sequence
<220> FEATURE:
<223> OTHER INFORMATION: Synthesized

<400> SEQUENCE: 52

Ala Tyr Asp Met Thr Gln Ser Pro Ser Ser Val Ser Ala Ser Val Gly
1 5 10 15

Asp Arg Val Thr Ile Lys Cys Gln Ala Ser Glu Asp Ile Tyr Ser Phe
20 25 30

Leu Ala Trp Tyr Gln Gln Lys Pro Gly Lys Ala Pro Lys Leu Leu Ile
35 40 45

His Ser Ala Ser Ser Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Gly Lys Asn Asn
85 90 95

Val Asp Asn Ala Phe Gly Gly Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

-continued

<210> SEQ ID NO 53
<211> LENGTH: 360
<212> TYPE: DNA
<213> ORGANISM: Artificial Sequence
<220> FEATURE:
<223> OTHER INFORMATION: Syntheized

<400> SEQUENCE: 53
gaggtgcagc tggtggagtc tgggggaggc ttggtccagc ctggggggtc cctgagactc 60
tcctgtgcag cctctggatt caccatcagt accaatgcaa tgagctgggt ccgccaggct 120
ccagggaagg ggctggagtg gatcggagtc attactggtc gtgatatcac atactacgcg 180
agctgggcga aaggcagatt caccatctcc agagacaatt ccaagaacac gctgtatctt 240
caaatgaaca gcctgagagc cgaggacacg gctgtgtatt actgtgcgag agacggtggt 300
tcttctgcta ttactagtaa caacatttgg ggccagggaa ccctggtcac cgtgtcgaca 360

<210> SEQ ID NO 54
<211> LENGTH: 120
<212> TYPE: PRT
<213> ORGANISM: Artificial Sequence
<220> FEATURE:
<223> OTHER INFORMATION: Syntheized

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Thr
        115                 120

<210> SEQ ID NO 55
<211> LENGTH: 345
<212> TYPE: DNA
<213> ORGANISM: Artificial Sequence
<220> FEATURE:
<223> OTHER INFORMATION: Synthesized

<400> SEQUENCE: 55
cggtcgctgg tggagtctgg gggaggcttg gtccagcctg gggggtccct gagactctcc 60
tgtacagcct ctggattcac catcagtagc taccacatgc agtgggtccg ccaggctcca 120
gggaaggggc tggagtacat cggaaccatt agtagtggtg gtaatgtata ctacgcaagc 180
tccgctagag gcagattcac catctccaga ccctcgtcca agaacacggt ggatcttcaa 240
atgaacagcc tgagagccga ggacacggct gtgtattact gtgcgagaga ctctggttat 300
agtgatccta tgtggggcca gggaaccctg gtcaccgtgt cgaca 345

<210> SEQ ID NO 56
<211> LENGTH: 115
<212> TYPE: PRT
<213> ORGANISM: Artificial Sequence
<220> FEATURE:
<223> OTHER INFORMATION: Synthesized

<400> SEQUENCE: 56

```
Arg Ser Leu Val Glu Ser Gly Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Thr
        115
```

<210> SEQ ID NO 57
<211> LENGTH: 345
<212> TYPE: DNA
<213> ORGANISM: Artificial Sequence
<220> FEATURE:
<223> OTHER INFORMATION: Synthesized

<400> SEQUENCE: 57

```
cagtcggtgg aggagtctgg gggaggcttg gtccagcctg gggggtccct gagactctcc      60

tgtaccgcct ctggaatcga ccttaatacc tacgacatga tctgggtccg ccaggctcca     120

ggcaaggggc tagagtgggt tggaatcatt acttatagtg gtagtagata ctacgcgaac     180

tgggcgaaag gccgattcac catctccaaa gacaatacca agaacacggt gtatctgcaa     240

atgaacagcc tgagagctga ggacacggct gtgtattact gtgcgagaga ttatatgagt     300

ggttcccact tgtggggcca gggaaccctg gtcaccgtgt cgaca                     345
```

<210> SEQ ID NO 58
<211> LENGTH: 115
<212> TYPE: PRT
<213> ORGANISM: Artificial Sequence
<220> FEATURE:
<223> OTHER INFORMATION: Synthesized

<400> SEQUENCE: 58

```
Gln Ser Val Glu Glu Ser Gly Gly Gly Leu Val Gln Pro Gly Gly Ser
1               5                   10                  15

Leu Arg Leu Ser Cys Thr Ala Ser Gly Ile Asp Leu Asn Thr Tyr Asp
            20                  25                  30

Met Ile Trp Val Arg Gln Ala Pro Gly Lys Gly Leu Glu Trp Val Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Asp Asn Thr Lys Asn Thr Val Tyr Leu Gln
```

```
65                  70                  75                  80

Met Asn Ser Leu Arg Ala Glu Asp Thr Ala Val Tyr Tyr Cys Ala Arg
                85                  90                  95

Asp Tyr Met Ser Gly Ser His Leu Trp Gly Gln Gly Thr Leu Val Thr
            100                 105                 110

Val Ser Thr
        115
```

<210> SEQ ID NO 59
<211> LENGTH: 366
<212> TYPE: DNA
<213> ORGANISM: Artificial Sequence
<220> FEATURE:
<223> OTHER INFORMATION: Synthesized

<400> SEQUENCE: 59

```
gaggtgcagc tgttggagtc tgggggaggc ttggtacagc ctggggggtc cctgagactc     60

tcctgtgcag cctctggatt ctccttcagt agcgggtacg acatgtgctg ggtccgccag    120

gctccaggga aggggctgga gtggatcgca tgcattgctg ctggtagtgc tggtatcact    180

tacgacgcga actgggcgaa aggccggttc accatctcca gagacaattc caagaacacg    240

ctgtatctgc aaatgaacag cctgagagcc gaggacacgg ccgtatatta ctgtgcgaga    300

tcggcgtttt cgttcgacta cgccatggac ctctggggcc agggaaccct ggtcaccgtc    360

tcgagc                                                               366
```

<210> SEQ ID NO 60
<211> LENGTH: 122
<212> TYPE: PRT
<213> ORGANISM: Artificial Sequence
<220> FEATURE:
<223> OTHER INFORMATION: Synthesized

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Ile Ala Cys Ile Ala Ala Gly Ser Ala Gly Ile Thr Tyr Asp Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ser Ala Phe Ser Phe Asp Tyr Ala Met Asp Leu Trp
            100                 105                 110

Gly Gln Gly Thr Leu Val Thr Val Ser Ser
        115                 120
```

<210> SEQ ID NO 61
<211> LENGTH: 330
<212> TYPE: DNA
<213> ORGANISM: Artificial Sequence
<220> FEATURE:
<223> OTHER INFORMATION: Synthesized

<400> SEQUENCE: 61

```
gacatccaga tgacccagtc tccttccacc ctgtctgcat ctgtaggaga cagagtcacc     60

atcacttgcc aggccagtca gagcattagt tcccacttaa actggtatca gcagaaacca    120

gggaaagccc ctaagctcct gatctataag gcatccactc tggcatctgg ggtcccatca    180

aggttcagcg gcagtggatc tgggacagaa tttactctca ccatcagcag cctgcagcct    240

gatgattttg caacttatta ctgccaacag ggttatagtt ggggtaatgt tgataatgtt    300

ttcggcggag ggaccaaggt ggagatcaaa                                     330


<210> SEQ ID NO 62
<211> LENGTH: 110
<212> TYPE: PRT
<213> ORGANISM: Artificial Sequence
<220> FEATURE:
<223> OTHER INFORMATION: Synthesized

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Trp Gly Asn
                85                  90                  95

Val Asp Asn Val Phe Gly Gly Gly Thr Lys Val Glu Ile Lys
            100                 105                 110


<210> SEQ ID NO 63
<211> LENGTH: 363
<212> TYPE: DNA
<213> ORGANISM: Artificial Sequence
<220> FEATURE:
<223> OTHER INFORMATION: Synthesized

<400> SEQUENCE: 63

gaggtgcagc tggtgcagtc tggagcagag gtgaagaaac caggagagtc tctgaagatc     60

tcctgtaagg gttctggata cagctttagc agttcatgga tcggctgggt gcgccaggca    120

cctgggaaag gcctggaatg gatggggatc atctatcctg atgactctga taccagatac    180

agtccatcct tccaaggcca ggtcaccatc tcagccgaca agtccatcag gactgcctac    240

ctgcagtgga gtagcctgaa ggcctcggac accgctatgt attactgtgc gagacatgtt    300

actatgattt ggggagttat tattgacttc tggggccagg gaaccctggt caccgtctcc    360

tca                                                                  363


<210> SEQ ID NO 64
<211> LENGTH: 121
<212> TYPE: PRT
<213> ORGANISM: Artificial Sequence
<220> FEATURE:
<223> OTHER INFORMATION: Synthesized

<400> SEQUENCE: 64

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ser Phe Ser Ser Ser
20 25 30

Trp Ile Gly Trp Val Arg Gln Ala Pro Gly Lys Gly Leu Glu Trp Met
35 40 45

Gly Ile Ile Tyr Pro Asp Asp Ser Asp Thr Arg Tyr Ser Pro Ser Phe
50 55 60

Gln Gly Gln Val Thr Ile Ser Ala Asp Lys Ser Ile Arg Thr Ala Tyr
65 70 75 80

Leu Gln Trp Ser Ser Leu Lys Ala Ser Asp Thr Ala Met Tyr Tyr Cys
85 90 95

Ala Arg His Val Thr Met Ile Trp Gly Val Ile Ile Asp Phe Trp Gly
100 105 110

Gln Gly Thr Leu Val Thr Val Ser Ser
115 120

<210> SEQ ID NO 65
<211> LENGTH: 321
<212> TYPE: DNA
<213> ORGANISM: Artificial Sequence
<220> FEATURE:
<223> OTHER INFORMATION: Synthesized

<400> SEQUENCE: 65
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccattcac tttcggccct 300
gggaccaaag tggatatcaa a 321

<210> SEQ ID NO 66
<211> LENGTH: 107
<212> TYPE: PRT
<213> ORGANISM: Artificial Sequence
<220> FEATURE:
<223> OTHER INFORMATION: Synthesized

<400> SEQUENCE: 66

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Phe
85 90 95

Thr Phe Gly Pro Gly Thr Lys Val Asp Ile Lys
100 105

<210> SEQ ID NO 67
<211> LENGTH: 348
<212> TYPE: DNA

<213> ORGANISM: Artificial Sequence
<220> FEATURE:
<223> OTHER INFORMATION: Synthesized

<400> SEQUENCE: 67
gatgtgcagc ttcaggagtc gggacctagc ctggtgaaac cttctcagtc tctgtccctc 60
acctgcactg tcactggcta ctcaatcacc agtgattttg cctggaactg gattcggcag 120
tttccaggaa acaagctgga gtggatgggc tacataagtt atagtggtaa cactaggtac 180
aacccatctc tcaaaagtcg aatctctatc actcgcgaca catccaagaa ccaattcttc 240
ctgcagttga actctgtgac tattgaggac acagccacat attactgtgt aacggcggga 300
cgcgggtttc cttattgggg ccaagggact ctggtcactg tctctgca 348

<210> SEQ ID NO 68
<211> LENGTH: 116
<212> TYPE: PRT
<213> ORGANISM: Artificial Sequence
<220> FEATURE:
<223> OTHER INFORMATION: Synthesized

<400> SEQUENCE: 68

Asp Val Gln Leu Gln Glu Ser Gly Pro Ser Leu Val Lys Pro Ser Gln
1 5 10 15

Ser Leu Ser Leu Thr Cys Thr Val Thr Gly Tyr Ser Ile Thr Ser Asp
20 25 30

Phe Ala Trp Asn Trp Ile Arg Gln Phe Pro Gly Asn Lys Leu Glu Trp
35 40 45

Met Gly Tyr Ile Ser Tyr Ser Gly Asn Thr Arg Tyr Asn Pro Ser Leu
50 55 60

Lys Ser Arg Ile Ser Ile Thr Arg Asp Thr Ser Lys Asn Gln Phe Phe
65 70 75 80

Leu Gln Leu Asn Ser Val Thr Ile Glu Asp Thr Ala Thr Tyr Tyr Cys
85 90 95

Val Thr Ala Gly Arg Gly Phe Pro Tyr Trp Gly Gln Gly Thr Leu Val
100 105 110

Thr Val Ser Ala
115

<210> SEQ ID NO 69
<211> LENGTH: 321
<212> TYPE: DNA
<213> ORGANISM: Artificial Sequence
<220> FEATURE:
<223> OTHER INFORMATION: Synthesized

<400> SEQUENCE: 69
gacatcctga tgacccaatc tccatcctcc atgtctgtat ctctgggaga cacagtcagc 60
atcacttgcc attcaagtca ggacattaac agtaatatag ggtggttgca gcagagacca 120
gggaaatcat ttaagggcct gatctatcat ggaaccaact tggacgatga agttccatca 180
aggttcagtg gcagtggatc tggagccgat tattctctca ccatcagcag cctggaatct 240
gaagattttg cagactatta ctgtgtacag tatgctcagt ttccgtggac gttcggtgga 300
ggcaccaagc tggaaatcaa a 321

<210> SEQ ID NO 70
<211> LENGTH: 107
<212> TYPE: PRT
<213> ORGANISM: Artificial Sequence

```
<220> FEATURE:
<223> OTHER INFORMATION: Synthesized

<400> SEQUENCE: 70

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys
            100                 105


<210> SEQ ID NO 71
<211> LENGTH: 33
<212> TYPE: DNA
<213> ORGANISM: Artificial Sequence
<220> FEATURE:
<223> OTHER INFORMATION: Synthesized

<400> SEQUENCE: 71

ggcggtggag ggtccggcgg tggtggctcc gga                                 33


<210> SEQ ID NO 72
<211> LENGTH: 11
<212> TYPE: PRT
<213> ORGANISM: Artificial Sequence
<220> FEATURE:
<223> OTHER INFORMATION: Synthesized

<400> SEQUENCE: 72

Gly Gly Gly Gly Ser Gly Gly Gly Gly Ser Gly
1               5                   10


<210> SEQ ID NO 73
<211> LENGTH: 30
<212> TYPE: DNA
<213> ORGANISM: Artificial Sequence
<220> FEATURE:
<223> OTHER INFORMATION: Synthesized

<400> SEQUENCE: 73

ggcggtggag ggtccggcgg tggtggatca                                     30


<210> SEQ ID NO 74
<211> LENGTH: 10
<212> TYPE: PRT
<213> ORGANISM: Artificial Sequence
<220> FEATURE:
<223> OTHER INFORMATION: Synthesized

<400> SEQUENCE: 74

Gly Gly Gly Gly Ser Gly Gly Gly Gly Ser
1               5                   10


<210> SEQ ID NO 75
<211> LENGTH: 30
```

<212> TYPE: DNA
<213> ORGANISM: Artificial Sequence
<220> FEATURE:
<223> OTHER INFORMATION: Synthesized

<400> SEQUENCE: 75
ggcggtggag ggtccggcgg tggtggatcc 30

<210> SEQ ID NO 76
<211> LENGTH: 10
<212> TYPE: PRT
<213> ORGANISM: Artificial Sequence
<220> FEATURE:
<223> OTHER INFORMATION: Synthesized

<400> SEQUENCE: 76

Gly Gly Gly Gly Ser Gly Gly Gly Gly Ser
1 5 10

<210> SEQ ID NO 77
<211> LENGTH: 60
<212> TYPE: DNA
<213> ORGANISM: Artificial Sequence
<220> FEATURE:
<223> OTHER INFORMATION: Synthesized

<400> SEQUENCE: 77
ggcggtggcg gtagtggggg aggcggttct ggcggcggag ggtccggcgg tggaggatca 60

<210> SEQ ID NO 78
<211> LENGTH: 20
<212> TYPE: PRT
<213> ORGANISM: Artificial Sequence
<220> FEATURE:
<223> OTHER INFORMATION: Synthesized

<400> SEQUENCE: 78

Gly Gly Gly Gly Ser Gly Gly Gly Gly Ser Gly Gly Gly Gly Ser Gly
1 5 10 15

Gly Gly Gly Ser
20

<210> SEQ ID NO 79
<211> LENGTH: 3693
<212> TYPE: DNA
<213> ORGANISM: Artificial Sequence
<220> FEATURE:
<223> OTHER INFORMATION: synthesized

<400> SEQUENCE: 79
gacgtcgtga tgacccagtc tccttccacc ctgtctgcat ctgtaggaga cagagtcacc 60
atcaattgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagag ttcactctca ccatcagcag cctgcagcct 240
gatgattttg caacttatta ctgccaaggc tatttttatt ttattagtcg tacttatgta 300
aattctttcg gcggagggac caaggtggag atcaaaggcg gtggcggtag tgggggaggc 360
ggttctggcg gcggagggtc cggcggtgga ggatcagagg tgcagctggt ggagtctggg 420
ggaggcttgg tccagcctgg ggggtccctg agactctcct gtgcagcctc tggattcacc 480
atcagtacca atgcaatgag ctgggtccgc caggctccag ggaaggggct ggagtggatc 540
ggagtcatta ctggtcgtga tatcacatac tacgcgagct gggcgaaagg cagattcacc 600

```
atctccagag acaattccaa gaacacgctg tatcttcaaa tgaacagcct gagagccgag    660
gacacggctg tgtattactg tgcgcgcgac ggtggatcat ctgctattac tagtaacaac    720
atttggggcc aaggaactct ggtcaccgtt tcttcaggcg gtggagggtc cggcggtggt    780
ggatccgatg tgcagcttca ggagtcggga cctagcctgg tgaaaccttc tcagtctctg    840
tccctcacct gcactgtcac tggctactca atcaccagtg attttgcctg gaactggatt    900
cggcagtttc caggaaacaa gctggagtgg atgggctaca taagttatag tggtaacact    960
aggtacaacc catctctcaa aagtcgaatc tctatcactc gcgacacatc caagaaccaa   1020
ttcttcctgc agttgaactc tgtgactatt gaggacacag ccacatatta ctgtgtaacg   1080
gcgggacgcg ggtttcctta ttggggccaa gggactctgg tcactgtctc tgcagctagc   1140
accaagggcc catcggtctt ccccctggca ccctcctcca agagcacctc tgggggcaca   1200
gcggccctgg gctgcctggt caaggactac ttccccgaac cggtgacggt gtcgtggaac   1260
tcaggcgccc tgaccagcgg cgtgcacacc ttcccggctg tcctacagtc ctcaggactc   1320
tactccctca gcagcgtggt gaccgtgccc tccagcagct tgggcaccca gacctacatc   1380
tgcaacgtga atcacaagcc cagcaacacc aaggtggaca agagagttga gcccaaatct   1440
tgtgacaaaa ctcacacatg cccaccgtgc ccagcacctg aagccgcggg ggcaccgtca   1500
gtcttcctct tcccccaaa acccaaggac accctcatga tctcccggac ccctgaggtc   1560
acatgcgtgg tggtggacgt gagccacgaa gaccctgagg tcaagttcaa ctggtacgtg   1620
gacggcgtgg aggtgcataa tgccaagaca aagccgcggg aggagcagta caacagcacg   1680
taccgtgtgg tcagcgtcct caccgtcctg caccaggact ggctgaatgg caaggagtac   1740
aagtgcgcgg tctccaacaa agccctccca gcccccatcg agaaaaccat ctccaaagcc   1800
aaagggcagc cccgagaacc acaggtgtac accctgcccc catcccggga tgagctgacc   1860
aagaaccagg tcagcctgac ctgcctggtc aaaggcttct atcccagcga catcgccgtg   1920
gagtgggaga gcaatgggca gccggagaac aactacaaga ccacgcctcc cgtgctggac   1980
tccgacggct ccttcttcct ctatagcaag ctcaccgtgg acaagagcag gtggcagcag   2040
gggaacgtct tctcatgctc cgtgatgcat gaggctctgc acaaccacta cacgcagaag   2100
agcctctccc tgtctccggg tggcggtgga gggtccggcg gtggtggatc cgaggtgcag   2160
ctgttggagt ctgggggagg cttggtacag cctggggggt ccctgagact ctcctgtgca   2220
gcctctggat tctccttcag tagcgggtac gacatgtgct gggtccgcca ggctccaggg   2280
aaggggctgg agtggatcgc atgcattgct gctggtagtg ctggtatcac ttacgacgcg   2340
aactgggcga aaggccggtt caccatctcc agagacaatt ccaagaacac gctgtatctg   2400
caaatgaaca gcctgagagc cgaggacacg gccgtatatt actgtgcgag atcggcgttt   2460
tcgttcgact acgccatgga cctctggggc cagggaaccc tggtcaccgt ctcgagcggc   2520
ggtggcggta gtgggggagg cggttctggc ggcggagggt ccggcggtgg aggatcagac   2580
atccagatga cccagtctcc ttccaccctg tctgcatctg taggagacag agtcaccatc   2640
acttgccagg ccagtcagag cattagttcc cacttaaact ggtatcagca gaaaccaggg   2700
aaagccccta agctcctgat ctataaggca tccactctgg catctggggt cccatcaagg   2760
ttcagcggca gtggatctgg gacagaattt actctcacca tcagcagcct gcagcctgat   2820
gattttgcaa cttattactg ccaacagggt tatagttggg gtaatgttga taatgttttc   2880
ggcggaggga ccaaggtgga gatcaaaggc ggtggagggt ccggcggtgg tggatcccag   2940
```

-continued

```
tcgctggtgg agtctggggg aggcttggta cagcctgggg ggtccctgag actctcctgt   3000

gcagcctctg gattctcctt cagtagcaac tactggatat gctgggtccg ccaggctcca   3060

gggaaggggc tggagtggat cgcatgtatt tatgttggta gtagtggtga cacttactac   3120

gcgagctccg cgaaaggccg gttcaccatc tccagagaca attccaagaa cacgctgtat   3180

ctgcaaatga acagcctgag agccgaggac acggccgtat attactgtgc gagagatagt   3240

agtagttatt atatgtttaa cttgtggggc cagggaaccc tggtcaccgt ctcttcaggc   3300

ggtggcggta gtgggggagg cggttctggc ggcggagggt ccggcggtgg aggatcagcc   3360

cttgtgatga cccagtctcc ttccaccctg tctgcatctg taggagacag agtcaccatc   3420

aattgccagg ccagtgagga cattgatacc tatttagcct ggtatcagca gaaaccaggg   3480

aaagccccta agctcctgat cttttacgca tccgatctgg catctggggt cccatcaagg   3540

ttcagcggca gtggatctgg gacagaattt actctcacca tcagcagcct gcagcctgat   3600

gattttgcaa cttattactg ccaaggcggt tactatacta gtagtgctga tacgaggggt   3660

gctttcggcg gagggaccaa ggtggagatc aaa                                3693


<210> SEQ ID NO 80
<211> LENGTH: 1231
<212> TYPE: PRT
<213> ORGANISM: Artificial Sequence
<220> FEATURE:
<223> OTHER INFORMATION: Synthesized

<400> SEQUENCE: 80

Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Ile Ser Thr Asn Ala Met Ser Trp Val Arg Gln Ala Pro Gly Lys Gly
                165                 170                 175

Leu Glu Trp Ile Gly Val Ile Thr Gly Arg Asp Ile Thr Tyr Tyr Ala
            180                 185                 190

Ser Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Gly Gly Ser Ser Ala Ile Thr Ser Asn Asn
```

-continued

```
225                 230                 235                 240

Ile Trp Gly Gln Gly Thr Leu Val Thr Val Ser Ser Gly Gly Gly Gly
                245                 250                 255

Ser Gly Gly Gly Gly Ser Asp Val Gln Leu Gln Glu Ser Gly Pro Ser
            260                 265                 270

Leu Val Lys Pro Ser Gln Ser Leu Ser Leu Thr Cys Thr Val Thr Gly
        275                 280                 285

Tyr Ser Ile Thr Ser Asp Phe Ala Trp Asn Trp Ile Arg Gln Phe Pro
    290                 295                 300

Gly Asn Lys Leu Glu Trp Met Gly Tyr Ile Ser Tyr Ser Gly Asn Thr
305                 310                 315                 320

Arg Tyr Asn Pro Ser Leu Lys Ser Arg Ile Ser Ile Thr Arg Asp Thr
                325                 330                 335

Ser Lys Asn Gln Phe Phe Leu Gln Leu Asn Ser Val Thr Ile Glu Asp
            340                 345                 350

Thr Ala Thr Tyr Tyr Cys Val Thr Ala Gly Arg Gly Phe Pro Tyr Trp
        355                 360                 365

Gly Gln Gly Thr Leu Val Thr Val Ser Ala Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Gln Thr Tyr Ile Cys Asn Val Asn
    450                 455                 460

His Lys Pro Ser Asn Thr Lys Val Asp Lys Arg Val Glu Pro Lys Ser
465                 470                 475                 480

Cys Asp Lys Thr His Thr Cys Pro Pro Cys Pro Ala Pro Glu Ala Ala
                485                 490                 495

Gly Ala Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Ala Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655
```

```
Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Gly Gly Gly Gly Ser Gly Gly Gly Gly Ser Glu Val Gln
705                 710                 715                 720

Leu Leu Glu Ser Gly Gly Gly Leu Val Gln Pro Gly Gly Ser Leu Arg
                725                 730                 735

Leu Ser Cys Ala Ala Ser Gly Phe Ser Phe Ser Ser Gly Tyr Asp Met
            740                 745                 750

Cys Trp Val Arg Gln Ala Pro Gly Lys Gly Leu Glu Trp Ile Ala Cys
        755                 760                 765

Ile Ala Ala Gly Ser Ala Gly Ile Thr Tyr Asp Ala Asn Trp Ala Lys
    770                 775                 780

Gly Arg Phe Thr Ile Ser Arg Asp Asn Ser Lys Asn Thr Leu Tyr Leu
785                 790                 795                 800

Gln Met Asn Ser Leu Arg Ala Glu Asp Thr Ala Val Tyr Tyr Cys Ala
                805                 810                 815

Arg Ser Ala Phe Ser Phe Asp Tyr Ala Met Asp Leu Trp Gly Gln Gly
            820                 825                 830

Thr Leu Val Thr Val Ser Ser Gly Gly Gly Gly Ser Gly Gly Gly Gly
        835                 840                 845

Ser Gly Gly Gly Gly Ser Gly Gly Gly Gly Ser Asp Ile Gln Met Thr
    850                 855                 860

Gln Ser Pro Ser Thr Leu Ser Ala Ser Val Gly Asp Arg Val Thr Ile
865                 870                 875                 880

Thr Cys Gln Ala Ser Gln Ser Ile Ser Ser His Leu Asn Trp Tyr Gln
                885                 890                 895

Gln Lys Pro Gly Lys Ala Pro Lys Leu Leu Ile Tyr Lys Ala Ser Thr
            900                 905                 910

Leu Ala Ser Gly Val Pro Ser Arg Phe Ser Gly Ser Gly Ser Gly Thr
        915                 920                 925

Glu Phe Thr Leu Thr Ile Ser Ser Leu Gln Pro Asp Asp Phe Ala Thr
    930                 935                 940

Tyr Tyr Cys Gln Gln Gly Tyr Ser Trp Gly Asn Val Asp Asn Val Phe
945                 950                 955                 960

Gly Gly Gly Thr Lys Val Glu Ile Lys Gly Gly Gly Gly Ser Gly Gly
                965                 970                 975

Gly Gly Ser Gln Ser Leu Val Glu Ser Gly Gly Gly Leu Val Gln Pro
            980                 985                 990

Gly Gly Ser Leu Arg Leu Ser Cys  Ala Ala Ser Gly Phe  Ser Phe Ser
        995                 1000                1005

Ser Asn  Tyr Trp Ile Cys Trp  Val Arg Gln Ala Pro  Gly Lys Gly
    1010                 1015                 1020

Leu Glu  Trp Ile Ala Cys Ile  Tyr Val Gly Ser Ser  Gly Asp Thr
    1025                 1030                 1035

Tyr Tyr  Ala Ser Ser Ala Lys  Gly Arg Phe Thr Ile  Ser Arg Asp
    1040                 1045                 1050

Asn Ser  Lys Asn Thr Leu Tyr  Leu Gln Met Asn Ser  Leu Arg Ala
    1055                 1060                 1065
```

Glu Asp Thr Ala Val Tyr Tyr Cys Ala Arg Asp Ser Ser Ser Tyr
1070 1075 1080

Tyr Met Phe Asn Leu Trp Gly Gln Gly Thr Leu Val Thr Val Ser
1085 1090 1095

Ser Gly Gly Gly Gly Ser Gly Gly Gly Gly Ser Gly Gly Gly Gly
1100 1105 1110

Ser Gly Gly Gly Gly Ser Ala Leu Val Met Thr Gln Ser Pro Ser
1115 1120 1125

Thr Leu Ser Ala Ser Val Gly Asp Arg Val Thr Ile Asn Cys Gln
1130 1135 1140

Ala Ser Glu Asp Ile Asp Thr Tyr Leu Ala Trp Tyr Gln Gln Lys
1145 1150 1155

Pro Gly Lys Ala Pro Lys Leu Leu Ile Phe Tyr Ala Ser Asp Leu
1160 1165 1170

Ala Ser Gly Val Pro Ser Arg Phe Ser Gly Ser Gly Ser Gly Thr
1175 1180 1185

Glu Phe Thr Leu Thr Ile Ser Ser Leu Gln Pro Asp Asp Phe Ala
1190 1195 1200

Thr Tyr Tyr Cys Gln Gly Gly Tyr Tyr Thr Ser Ser Ala Asp Thr
1205 1210 1215

Arg Gly Ala Phe Gly Gly Gly Thr Lys Val Glu Ile Lys
1220 1225 1230

<210> SEQ ID NO 81
<211> LENGTH: 642
<212> TYPE: DNA
<213> ORGANISM: Artificial Sequence
<220> FEATURE:
<223> OTHER INFORMATION: Synthesized

<400> SEQUENCE: 81
gacatcctga tgacccaatc tccatcctcc atgtctgtat ctctgggaga cacagtcagc 60
atcacttgcc attcaagtca ggacattaac agtaatatag ggtggttgca gcagagacca 120
gggaaatcat ttaagggcct gatctatcat ggaaccaact tggacgatga agttccatca 180
aggttcagtg gcagtggatc tggagccgat tattctctca ccatcagcag cctggaatct 240
gaagattttg cagactatta ctgtgtacag tatgctcagt ttccgtggac gttcggtgga 300
ggcaccaagc tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 82
<211> LENGTH: 214
<212> TYPE: PRT
<213> ORGANISM: Artificial Sequence
<220> FEATURE:
<223> OTHER INFORMATION: Synthesized

<400> SEQUENCE: 82

Asp Ile Leu Met Thr Gln Ser Pro Ser Ser Met Ser Val Ser Leu Gly
1 5 10 15

Asp Thr Val Ser Ile Thr Cys His Ser Ser Gln Asp Ile Asn Ser Asn

```
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 83
<211> LENGTH: 3678
<212> TYPE: DNA
<213> ORGANISM: Artificial Sequence
<220> FEATURE:
<223> OTHER INFORMATION: Synthesized

<400> SEQUENCE: 83

gacatcctga tgacccaatc tccatcctcc atgtctgtat ctctgggaga cacagtcagc     60

atcacttgcc attcaagtca ggacattaac agtaatatag ggtggttgca gcagagacca    120

gggaaatcat ttaagggcct gatctatcat ggaaccaact tggacgatga agttccatca    180

aggttcagtg gcagtggatc tggagccgat tattctctca ccatcagcag cctggaatct    240

gaagattttg cagactatta ctgtgtacag tatgctcagt ttccgtggac gttcggtgga    300

ggcaccaagc tggaaatcaa aggcggtggc ggtagtgggg gaggcggttc tggcggcgga    360

gggtccggcg gtggaggatc agatgtgcag cttcaggagt cgggacctag cctggtgaaa    420

ccttctcagt ctctgtccct cacctgcact gtcactggct actcaatcac cagtgatttt    480

gcctggaact ggattcggca gtttccagga aacaagctgg agtggatggg ctacataagt    540

tatagtggta acactaggta caacccatct ctcaaaagtc gaatctctat cactcgcgac    600

acatccaaga accaattctt cctgcagttg aactctgtga ctattgagga cacagccaca    660

tattactgtg taacggcggg acgcgggttt ccttattggg gccaagggac tctggtcact    720

gtctctgcag gcggtggagg gtccggcggt ggtggatccg aggtgcagct ggtggagtct    780

gggggaggct tggtccagcc tgggggggtcc ctgagactct cctgtgcagc ctctggattc    840

accatcagta ccaatgcaat gagctgggtc cgccaggctc cagggaaggg gctggagtgg    900

atcggagtca ttactggtcg tgatatcaca tactacgcga gctgggcgaa aggcagattc    960
```

```
accatctcca gagacaattc caagaacacg ctgtatcttc aaatgaacag cctgagagcc   1020
gaggacacgg ctgtgtatta ctgtgcgcgc gacggtggat catctgctat tactagtaac   1080
aacatttggg gccaaggaac tctggtcacc gtttcttcag ctagcaccaa gggcccatcg   1140
gtcttccccc tggcaccctc ctccaagagc acctctgggg gcacagcggc cctgggctgc   1200
ctggtcaagg actacttccc cgaaccggtg acggtgtcgt ggaactcagg cgccctgacc   1260
agcggcgtgc acaccttccc ggctgtccta cagtcctcag gactctactc cctcagcagc   1320
gtggtgaccg tgccctccag cagcttgggc acccagacct acatctgcaa cgtgaatcac   1380
aagcccagca acaccaaggt ggacaagaga gttgagccca aatcttgtga caaaactcac   1440
acatgcccac cgtgcccagc acctgaagcc gcgggggcac cgtcagtctt cctcttcccc   1500
ccaaaaccca aggacaccct catgatctcc cggacccctg aggtcacatg cgtggtggtg   1560
gacgtgagcc acgaagaccc tgaggtcaag ttcaactggt acgtggacgg cgtggaggtg   1620
cataatgcca agacaaagcc gcgggaggag cagtacaaca gcacgtaccg tgtggtcagc   1680
gtcctcaccg tcctgcacca ggactggctg aatggcaagg agtacaagtg cgcggtctcc   1740
aacaaagccc tcccagcccc catcgagaaa accatctcca aagccaaagg gcagccccga   1800
gaaccacagg tgtacaccct gcccccatcc cgggatgagc tgaccaagaa ccaggtcagc   1860
ctgacctgcc tggtcaaagg cttctatccc agcgacatcg ccgtggagtg ggagagcaat   1920
gggcagccgg agaacaacta caagaccacg cctcccgtgc tggactccga cggctccttc   1980
ttcctctata gcaagctcac cgtggacaag agcaggtggc agcaggggaa cgtcttctca   2040
tgctccgtga tgcatgaggc tctgcacaac cactacacgc agaagagcct ctccctgtct   2100
ccgggtggcg gtggagggtc cggcggtggt ggatccgagg tgcagctgtt ggagtctggg   2160
ggaggcttgg tacagcctgg ggggtccctg agactctcct gtgcagcctc tggattctcc   2220
ttcagtagcg ggtacgacat gtgctgggtc cgccaggctc cagggaaggg gctggagtgg   2280
atcgcatgca ttgctgctgg tagtgctggt atcacttacg acgcgaactg ggcgaaaggc   2340
cggttcacca tctccagaga caattccaag aacacgctgt atctgcaaat gaacagcctg   2400
agagccgagg acacggccgt atattactgt gcgagatcgg cgttttcgtt cgactacgcc   2460
atggacctct ggggccaggg aaccctggtc accgtctcga gcggcggtgg cggtagtggg   2520
ggaggcggtt ctggcggcgg agggtccggc ggtggaggat cagacatcca gatgacccag   2580
tctccttcca ccctgtctgc atctgtagga gacagagtca ccatcacttg ccaggccagt   2640
cagagcatta gttcccactt aaactggtat cagcagaaac cagggaaagc ccctaagctc   2700
ctgatctata aggcatccac tctggcatct ggggtcccat caaggttcag cggcagtgga   2760
tctgggacag aatttactct caccatcagc agcctgcagc ctgatgattt tgcaacttat   2820
tactgccaac agggttatag ttggggtaat gttgataatg ttttcggcgg agggaccaag   2880
gtggagatca aaggcggtgg agggtccggc ggtggtggat cccagtcgct ggtggagtct   2940
gggggaggct tggtacagcc tggggggtcc ctgagactct cctgtgcagc ctctggattc   3000
tccttcagta gcaactactg gatatgctgg gtccgccagg ctccagggaa ggggctggag   3060
tggatcgcat gtatttatgt tggtagtagt ggtgacactt actacgcgag ctccgcgaaa   3120
ggccggttca ccatctccag agacaattcc aagaacacgc tgtatctgca aatgaacagc   3180
ctgagagccg aggacacggc cgtatattac tgtgcgagag atagtagtag ttattatatg   3240
tttaacttgt ggggccaggg aaccctggtc accgtctctt caggcggtgg cggtagtggg   3300
```

-continued

```
ggaggcggtt ctggcggcgg agggtccggc ggtggaggat cagcccttgt gatgacccag   3360

tctccttcca ccctgtctgc atctgtagga gacagagtca ccatcaattg ccaggccagt   3420

gaggacattg atacctattt agcctggtat cagcagaaac cagggaaagc ccctaagctc   3480

ctgatctttt acgcatccga tctggcatct ggggtcccat caaggttcag cggcagtgga   3540

tctgggacag aatttactct caccatcagc agcctgcagc ctgatgattt tgcaacttat   3600

tactgccaag gcggttacta tactagtagt gctgatacga ggggtgcttt cggcggaggg   3660

accaaggtgg agatcaaa                                                 3678


<210> SEQ ID NO 84
<211> LENGTH: 1226
<212> TYPE: PRT
<213> ORGANISM: Artificial Sequence
<220> FEATURE:
<223> OTHER INFORMATION: Synthesized

<400> SEQUENCE: 84

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Asp
        115                 120                 125

Val Gln Leu Gln Glu Ser Gly Pro Ser Leu Val Lys Pro Ser Gln Ser
    130                 135                 140

Leu Ser Leu Thr Cys Thr Val Thr Gly Tyr Ser Ile Thr Ser Asp Phe
145                 150                 155                 160

Ala Trp Asn Trp Ile Arg Gln Phe Pro Gly Asn Lys Leu Glu Trp Met
                165                 170                 175

Gly Tyr Ile Ser Tyr Ser Gly Asn Thr Arg Tyr Asn Pro Ser Leu Lys
            180                 185                 190

Ser Arg Ile Ser Ile Thr Arg Asp Thr Ser Lys Asn Gln Phe Phe Leu
        195                 200                 205

Gln Leu Asn Ser Val Thr Ile Glu Asp Thr Ala Thr Tyr Tyr Cys Val
    210                 215                 220

Thr Ala Gly Arg Gly Phe Pro Tyr Trp Gly Gln Gly Thr Leu Val Thr
225                 230                 235                 240

Val Ser Ala Gly Gly Gly Gly Ser Gly Gly Gly Gly Ser Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Phe Thr Ile Ser Thr Asn Ala Met Ser
        275                 280                 285

Trp Val Arg Gln Ala Pro Gly Lys Gly Leu Glu Trp Ile Gly Val Ile
```

```
    290                 295                 300

Thr Gly Arg Asp Ile Thr Tyr Tyr Ala Ser Trp Ala Lys Gly Arg Phe
305                 310                 315                 320

Thr Ile Ser Arg Asp Asn Ser Lys Asn Thr Leu Tyr Leu Gln Met Asn
                325                 330                 335

Ser Leu Arg Ala Glu Asp Thr Ala Val Tyr Tyr Cys Ala Arg Asp Gly
            340                 345                 350

Gly Ser Ser Ala Ile Thr Ser Asn Asn Ile Trp Gly Gln Gly Thr Leu
        355                 360                 365

Val Thr Val Ser Ser Ala Ser Thr Lys Gly Pro Ser Val Phe Pro Leu
    370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
    450                 455                 460

Thr Lys Val Asp Lys Arg Val Glu Pro Lys Ser Cys Asp Lys Thr His
465                 470                 475                 480

Thr Cys Pro Pro Cys Pro Ala Pro Glu Ala Ala Gly Ala Pro Ser Val
                485                 490                 495

Phe Leu Phe Pro Pro Lys Pro Lys Asp Thr Leu Met Ile Ser Arg Thr
            500                 505                 510

Pro Glu Val Thr Cys Val Val Val Asp Val Ser His Glu Asp Pro Glu
        515                 520                 525

Val Lys Phe Asn Trp Tyr Val Asp Gly Val Glu Val His Asn Ala Lys
    530                 535                 540

Thr Lys Pro Arg Glu Glu Gln Tyr Asn Ser Thr Tyr Arg Val Val Ser
545                 550                 555                 560

Val Leu Thr Val Leu His Gln Asp Trp Leu Asn Gly Lys Glu Tyr Lys
                565                 570                 575

Cys Ala Val Ser Asn Lys Ala Leu Pro Ala Pro Ile Glu Lys Thr Ile
            580                 585                 590

Ser Lys Ala Lys Gly Gln Pro Arg Glu Pro Gln Val Tyr Thr Leu Pro
        595                 600                 605

Pro Ser Arg Asp Glu Leu Thr Lys Asn Gln Val Ser Leu Thr Cys Leu
    610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
            660                 665                 670

Trp Gln Gln Gly Asn Val Phe Ser Cys Ser Val Met His Glu Ala Leu
        675                 680                 685

His Asn His Tyr Thr Gln Lys Ser Leu Ser Leu Ser Pro Gly Gly Gly
    690                 695                 700

Gly Gly Ser Gly Gly Gly Gly Ser Glu Val Gln Leu Leu Glu Ser Gly
705                 710                 715                 720
```

-continued

```
Gly Gly Leu Val Gln Pro Gly Gly Ser Leu Arg Leu Ser Cys Ala Ala
                725                 730                 735

Ser Gly Phe Ser Phe Ser Ser Gly Tyr Asp Met Cys Trp Val Arg Gln
            740                 745                 750

Ala Pro Gly Lys Gly Leu Glu Trp Ile Ala Cys Ile Ala Ala Gly Ser
        755                 760                 765

Ala Gly Ile Thr Tyr Asp Ala Asn Trp Ala Lys Gly Arg Phe Thr Ile
    770                 775                 780

Ser Arg Asp Asn Ser Lys Asn Thr Leu Tyr Leu Gln Met Asn Ser Leu
785                 790                 795                 800

Arg Ala Glu Asp Thr Ala Val Tyr Tyr Cys Ala Arg Ser Ala Phe Ser
                805                 810                 815

Phe Asp Tyr Ala Met Asp Leu Trp Gly Gln Gly Thr Leu Val Thr Val
            820                 825                 830

Ser Ser Gly Gly Gly Gly Ser Gly Gly Gly Gly Ser Gly Gly Gly Gly
        835                 840                 845

Ser Gly Gly Gly Gly Ser Asp Ile Gln Met Thr Gln Ser Pro Ser Thr
    850                 855                 860

Leu Ser Ala Ser Val Gly Asp Arg Val Thr Ile Thr Cys Gln Ala Ser
865                 870                 875                 880

Gln Ser Ile Ser Ser His Leu Asn Trp Tyr Gln Gln Lys Pro Gly Lys
                885                 890                 895

Ala Pro Lys Leu Leu Ile Tyr Lys Ala Ser Thr Leu Ala Ser Gly Val
            900                 905                 910

Pro Ser Arg Phe Ser Gly Ser Gly Ser Gly Thr Glu Phe Thr Leu Thr
        915                 920                 925

Ile Ser Ser Leu Gln Pro Asp Asp Phe Ala Thr Tyr Tyr Cys Gln Gln
    930                 935                 940

Gly Tyr Ser Trp Gly Asn Val Asp Asn Val Phe Gly Gly Gly Thr Lys
945                 950                 955                 960

Val Glu Ile Lys Gly Gly Gly Gly Ser Gly Gly Gly Gly Ser Gln Ser
                965                 970                 975

Leu Val Glu Ser Gly Gly Gly Leu Val Gln Pro Gly Gly Ser Leu Arg
            980                 985                 990

Leu Ser Cys Ala Ala Ser Gly Phe  Ser Phe Ser Ser Asn  Tyr Trp Ile
        995                 1000                1005

Cys Trp  Val Arg Gln Ala Pro  Gly Lys Gly Leu Glu  Trp Ile Ala
    1010                1015                1020

Cys Ile  Tyr Val Gly Ser Ser  Gly Asp Thr Tyr Tyr  Ala Ser Ser
    1025                1030                1035

Ala Lys  Gly Arg Phe Thr Ile  Ser Arg Asp Asn Ser  Lys Asn Thr
    1040                1045                1050

Leu Tyr  Leu Gln Met Asn Ser  Leu Arg Ala Glu Asp  Thr Ala Val
    1055                1060                1065

Tyr Tyr  Cys Ala Arg Asp Ser  Ser Ser Tyr Tyr Met  Phe Asn Leu
    1070                1075                1080

Trp Gly  Gln Gly Thr Leu Val  Thr Val Ser Ser Gly  Gly Gly Gly
    1085                1090                1095

Ser Gly  Gly Gly Gly Ser Gly  Gly Gly Gly Ser Gly  Gly Gly Gly
    1100                1105                1110

Ser Ala  Leu Val Met Thr Gln  Ser Pro Ser Thr Leu  Ser Ala Ser
    1115                1120                1125
```

```
Val Gly  Asp Arg Val Thr Ile  Asn Cys Gln Ala Ser  Glu Asp Ile
    1130                 1135                 1140

Asp Thr  Tyr Leu Ala Trp Tyr  Gln Gln Lys Pro Gly  Lys Ala Pro
    1145                 1150                 1155

Lys Leu  Leu Ile Phe Tyr Ala  Ser Asp Leu Ala Ser  Gly Val Pro
    1160                 1165                 1170

Ser Arg  Phe Ser Gly Ser Gly  Ser Gly Thr Glu Phe  Thr Leu Thr
    1175                 1180                 1185

Ile Ser  Ser Leu Gln Pro Asp  Asp Phe Ala Thr Tyr  Tyr Cys Gln
    1190                 1195                 1200

Gly Gly  Tyr Tyr Thr Ser Ser  Ala Asp Thr Arg Gly  Ala Phe Gly
    1205                 1210                 1215

Gly Gly  Thr Lys Val Glu Ile  Lys
    1220                 1225


<210> SEQ ID NO 85
<211> LENGTH: 657
<212> TYPE: DNA
<213> ORGANISM: Artificial Sequence
<220> FEATURE:
<223> OTHER INFORMATION: Synthesized

<400> SEQUENCE: 85

gacgtcgtga tgacccagtc tccttccacc ctgtctgcat ctgtaggaga cagagtcacc      60

atcaattgcc aagccagtga gagcattagc agttggttag cctggtatca gcagaaacca     120

gggaaagccc ctaagctcct gatctatgaa gcatccaaac tggcatctgg ggtcccatca     180

aggttcagcg gcagtggatc tgggacagaa ttcactctca ccatcagcag cctgcagcct     240

gatgattttg caacttatta ctgccaaggc tatttttatt ttattagtcg tacttatgta     300

aattctttcg gcggagggac caaggtggag atcaaacgta cggtggctgc accatctgtc     360

ttcatcttcc cgccatctga tgagcagttg aaatctggaa ctgcctctgt tgtgtgcctg     420

ctgaataact tctatcccag agaggccaaa gtacagtgga aggtggataa cgccctccaa     480

tcgggtaact cccaggagag tgtcacagag caggacagca aggacagcac ctacagcctc     540

agcagcaccc tgacgctgag caaagcagac tacgagaaac acaaagtcta cgcctgcgaa     600

gtcacccatc agggcctgag ctcgcccgtc acaaagagct tcaacagggg agagtgt        657


<210> SEQ ID NO 86
<211> LENGTH: 219
<212> TYPE: PRT
<213> ORGANISM: Artificial Sequence
<220> FEATURE:
<223> OTHER INFORMATION: Synthesized

<400> SEQUENCE: 86

Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
```

-continued

```
                85                  90                  95

Arg Thr Tyr Val Asn Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 87
<211> LENGTH: 3681
<212> TYPE: DNA
<213> ORGANISM: Artificial Sequence
<220> FEATURE:
<223> OTHER INFORMATION: Synthesized

<400> SEQUENCE: 87

```
gacgttgtga tgacccagtc tccatcttcc gtgtctgcat ctgtaggaga cagagtcacc     60

atcacctgtc aggccagtca gaacattagg acttacttat cctggtatca gcagaaacca    120

gggaaagccc ctaagctcct gatctatgct gcagccaatc tggcatctgg ggtcccatca    180

aggttcagcg gcagtggatc tgggacagat ttcactctca ccatcagcga cctggagcct    240

ggcgatgctg caacttacta ttgtcagtct acctatcttg gtactgatta tgttggcggt    300

gctttcggcg gagggaccaa ggtggagatc aaaggcggtg gcggtagtgg gggaggcggt    360

tctggcggcg gagggtccgg cggtggagga tcacggtcgc tggtggagtc tgggggaggc    420

ttggtccagc ctggggggtc cctgagactc tcctgtacag cctctggatt caccatcagt    480

agctaccaca tgcagtgggt ccgccaggct ccagggaagg ggctggagta catcggaacc    540

attagtagtg gtggtaatgt atactacgcg agctccgcga gaggcagatt caccatctcc    600

agaccctcgt ccaagaacac ggtggatctt caaatgaaca gcctgagagc cgaggacacg    660

gctgtgtatt actgtgcgag agactctggt tatagtgatc ctatgtgggg ccagggaacc    720

ctggtcaccg tctcgagcgg cggtggaggg tccggcggtg gtggatccca gtcggtggag    780

gagtctgggg gaggcttggt ccagcctggg gggtccctga gactctcctg tacagcctct    840

ggaatcgacc ttaataccta cgacatgatc tgggtccgcc aggctccagg caaggggcta    900

gagtgggttg gaatcattac ttatagtggt agtagatact acgcgaactg ggcgaaaggc    960

cgattcacca tctccaaaga caataccaag aacacggtgt atctgcaaat gaacagcctg   1020

agagctgagg acacggctgt gtattactgt gccagagatt atatgagtgg ttcccacttg   1080

tggggccagg gaaccctggt caccgtctct agtgctagca ccaagggccc atcggtcttc   1140

cccctggcac cctcctccaa gagcacctct gggggcacag cggccctggg ctgcctggtc   1200

aaggactact tccccgaacc ggtgacggtg tcgtggaact caggcgccct gaccagcggc   1260

gtgcacacct tcccggctgt cctacagtcc tcaggactct actccctcag cagcgtggtg   1320
```

accgtgccct ccagcagctt gggcacccag acctacatct gcaacgtgaa tcacaagccc 1380
agcaacacca aggtggacaa gagagttgag cccaaatctt gtgacaaaac tcacacatgc 1440
ccaccgtgcc cagcacctga agccgcgggg gcaccgtcag tcttcctctt ccccccaaaa 1500
cccaaggaca ccctcatgat ctcccggacc cctgaggtca catgcgtggt ggtggacgtg 1560
agccacgaag accctgaggt caagttcaac tggtacgtgg acggcgtgga ggtgcataat 1620
gccaagacaa agccgcggga ggagcagtac aacagcacgt accgtgtggt cagcgtcctc 1680
accgtcctgc accaggactg gctgaatggc aaggagtaca agtgcgcggt ctccaacaaa 1740
gccctcccag cccccatcga gaaaaccatc tccaaagcca aagggcagcc ccgagaacca 1800
caggtgtata ccctgccccc atcccgggat gagctgacca agaaccaggt cagcctgacc 1860
tgcctggtca aaggcttcta tcccagcgac atcgccgtgg agtgggagag caatgggcag 1920
ccggagaaca actacaagac cacgcctccc gtgctggact ccgacggctc cttcttcctc 1980
tatagcaagc tcaccgtgga caagagcagg tggcagcagg ggaacgtctt ctcatgctcc 2040
gtgatgcatg aggctctgca caaccactac acgcagaaga gcctctccct gtctccgggt 2100
ggcggtggag ggtccggcgg tggtggatcc gaggtgcagc tgttggagtc tgggggaggc 2160
ttggtacagc ctggggggtc cctgagactc tcctgtgcag cctctggatt caccatcagt 2220
cgctaccaca tgacttgggt ccgccaggct ccagggaagg ggctggagtg gatcggacat 2280
atttatgtta ataatgatga cacagactac gcgagctccg cgaaaggccg gttcaccatc 2340
tccagagaca attccaagaa cacgctgtat ctgcaaatga acagcctgag agccgaggac 2400
acggccacct atttctgtgc gagattggat gttggtggtg gtggtgctta tattggggac 2460
atctggggcc agggaactct ggttaccgtc tcttcaggcg gtggcggtag tgggggaggc 2520
ggttctggcg gcggagggtc cggcggtgga ggatcagaca tccagatgac ccagtctcca 2580
tcctccctgt ctgcatctgt aggagacaga gtcaccatca cttgccagtc cagtcagagt 2640
gtttataaca acaacgactt agcctggtat cagcagaaac cagggaaagt tcctaagctc 2700
ctgatctatt atgcttccac tctggcatct ggggtcccat ctcggttcag tggcagtgga 2760
tctgggacag atttcactct caccatcagc agcctgcagc ctgaagatgt tgcaacttat 2820
tactgtgcag gcggttatga tacggatggt cttgatacgt ttgctttcgg cggagggacc 2880
aaggtggaga tcaaaggcgg tggagggtcc ggcggtggtg gatccgaggt gcagctggtg 2940
gagtctgggg gaggcttggt ccagcctggg gggtccctga gactctcctg tgcagcctct 3000
ggattcacca tcagtaccaa tgcaatgagc tgggtccgcc aggctccagg gaaggggctg 3060
gagtggatcg gagtcattac tggtcgtgat atcacatact acgcgagctg ggcgaaaggc 3120
agattcacca tctccagaga caattccaag aacacgctgt atcttcaaat gaacagcctg 3180
agagccgagg acacggctgt gtattactgt gcgcgcgacg gtggatcatc tgctattact 3240
agtaacaaca tttggggcca aggaactctg gtcaccgttt cttcaggcgg tggcggtagt 3300
gggggaggcg gttctggcgg cggagggtcc ggcggtggag gatcagacgt cgtgatgacc 3360
cagtctcctt ccaccctgtc tgcatctgta ggagacagag tcaccatcaa ttgccaagcc 3420
agtgagagca ttagcagttg gttagcctgg tatcagcaga aaccagggaa agcccctaag 3480
ctcctgatct atgaagcatc caaactggca tctggggtcc catcaaggtt cagcggcagt 3540
ggatctggga cagagttcac tctcaccatc agcagcctgc agcctgatga ttttgcaact 3600
tattactgcc aaggctattt ttattttatt agtcgtactt atgtaaattc tttcggcgga 3660

```
gggaccaagg tggagatcaa a                                            3681


<210> SEQ ID NO 88
<211> LENGTH: 1227
<212> TYPE: PRT
<213> ORGANISM: Artificial Sequence
<220> FEATURE:
<223> OTHER INFORMATION: Synthesized

<400> SEQUENCE: 88

Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
    50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
                85                  90                  95

Tyr Val Gly Gly Ala Phe Gly Gly Gly Thr Lys Val Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Arg Ser Leu Val Glu Ser Gly Gly Gly Leu Val Gln Pro
    130                 135                 140

Gly Gly Ser Leu Arg Leu Ser Cys Thr Ala Ser Gly Phe Thr Ile Ser
145                 150                 155                 160

Ser Tyr His Met Gln Trp Val Arg Gln Ala Pro Gly Lys Gly Leu Glu
                165                 170                 175

Tyr Ile Gly Thr Ile Ser Ser Gly Gly Asn Val Tyr Tyr Ala Ser Ser
            180                 185                 190

Ala Arg Gly Arg Phe Thr Ile Ser Arg Pro Ser Ser Lys Asn Thr Val
        195                 200                 205

Asp Leu Gln Met Asn Ser Leu Arg Ala Glu Asp Thr Ala Val Tyr Tyr
    210                 215                 220

Cys Ala Arg Asp Ser Gly Tyr Ser Asp Pro Met Trp Gly Gln Gly Thr
225                 230                 235                 240

Leu Val Thr Val Ser Ser Gly Gly Gly Gly Ser Gly Gly Gly Gly Ser
                245                 250                 255

Gln Ser Val Glu Glu Ser Gly Gly Gly Leu Val Gln Pro Gly Gly Ser
            260                 265                 270

Leu Arg Leu Ser Cys Thr Ala Ser Gly Ile Asp Leu Asn Thr Tyr Asp
        275                 280                 285

Met Ile Trp Val Arg Gln Ala Pro Gly Lys Gly Leu Glu Trp Val Gly
    290                 295                 300

Ile Ile Thr Tyr Ser Gly Ser Arg Tyr Tyr Ala Asn Trp Ala Lys Gly
305                 310                 315                 320

Arg Phe Thr Ile Ser Lys Asp Asn Thr Lys Asn Thr Val Tyr Leu Gln
                325                 330                 335

Met Asn Ser Leu Arg Ala Glu Asp Thr Ala Val Tyr Tyr Cys Ala Arg
            340                 345                 350

Asp Tyr Met Ser Gly Ser His Leu Trp Gly Gln Gly Thr Leu Val Thr
```

```
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Ala Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Ala
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Gly Gly Gly Gly
    690                 695                 700

Ser Gly Gly Gly Gly Ser Glu Val Gln Leu Leu Glu Ser Gly Gly Gly
705                 710                 715                 720

Leu Val Gln Pro Gly Gly Ser Leu Arg Leu Ser Cys Ala Ala Ser Gly
                725                 730                 735

Phe Thr Ile Ser Arg Tyr His Met Thr Trp Val Arg Gln Ala Pro Gly
            740                 745                 750

Lys Gly Leu Glu Trp Ile Gly His Ile Tyr Val Asn Asn Asp Asp Thr
        755                 760                 765

Asp Tyr Ala Ser Ser Ala Lys Gly Arg Phe Thr Ile Ser Arg Asp Asn
    770                 775                 780
```

```
Ser Lys Asn Thr Leu Tyr Leu Gln Met Asn Ser Leu Arg Ala Glu Asp
785                 790                 795                 800

Thr Ala Thr Tyr Phe Cys Ala Arg Leu Asp Val Gly Gly Gly Gly Ala
                805                 810                 815

Tyr Ile Gly Asp Ile Trp Gly Gln Gly Thr Leu Val Thr Val Ser Ser
            820                 825                 830

Gly Gly Gly Gly Ser Gly Gly Gly Gly Ser Gly Gly Gly Gly Ser Gly
        835                 840                 845

Gly Gly Gly Ser Asp Ile Gln Met Thr Gln Ser Pro Ser Ser Leu Ser
    850                 855                 860

Ala Ser Val Gly Asp Arg Val Thr Ile Thr Cys Gln Ser Ser Gln Ser
865                 870                 875                 880

Val Tyr Asn Asn Asn Asp Leu Ala Trp Tyr Gln Gln Lys Pro Gly Lys
                885                 890                 895

Val Pro Lys Leu Leu Ile Tyr Tyr Ala Ser Thr Leu Ala Ser Gly Val
            900                 905                 910

Pro Ser Arg Phe Ser Gly Ser Gly Ser Gly Thr Asp Phe Thr Leu Thr
        915                 920                 925

Ile Ser Ser Leu Gln Pro Glu Asp Val Ala Thr Tyr Tyr Cys Ala Gly
    930                 935                 940

Gly Tyr Asp Thr Asp Gly Leu Asp Thr Phe Ala Phe Gly Gly Gly Thr
945                 950                 955                 960

Lys Val Glu Ile Lys Gly Gly Gly Gly Ser Gly Gly Gly Gly Ser Glu
                965                 970                 975

Val Gln Leu Val Glu Ser Gly Gly Gly Leu Val Gln Pro Gly Gly Ser
            980                 985                 990

Leu Arg Leu Ser Cys Ala Ala Ser  Gly Phe Thr Ile Ser  Thr Asn Ala
        995                 1000                1005

Met Ser  Trp Val Arg Gln Ala  Pro Gly Lys Gly Leu  Glu Trp Ile
    1010                1015                1020

Gly Val  Ile Thr Gly Arg Asp  Ile Thr Tyr Tyr Ala  Ser Trp Ala
    1025                1030                1035

Lys Gly  Arg Phe Thr Ile Ser  Arg Asp Asn Ser Lys  Asn Thr Leu
    1040                1045                1050

Tyr Leu  Gln Met Asn Ser Leu  Arg Ala Glu Asp Thr  Ala Val Tyr
    1055                1060                1065

Tyr Cys  Ala Arg Asp Gly Gly  Ser Ser Ala Ile Thr  Ser Asn Asn
    1070                1075                1080

Ile Trp  Gly Gln Gly Thr Leu  Val Thr Val Ser Ser  Gly Gly Gly
    1085                1090                1095

Gly Ser  Gly Gly Gly Gly Ser  Gly Gly Gly Gly Ser  Gly Gly Gly
    1100                1105                1110

Gly Ser  Asp Val Val Met Thr  Gln Ser Pro Ser Thr  Leu Ser Ala
    1115                1120                1125

Ser Val  Gly Asp Arg Val Thr  Ile Asn Cys Gln Ala  Ser Glu Ser
    1130                1135                1140

Ile Ser  Ser Trp Leu Ala Trp  Tyr Gln Gln Lys Pro  Gly Lys Ala
    1145                1150                1155

Pro Lys  Leu Leu Ile Tyr Glu  Ala Ser Lys Leu Ala  Ser Gly Val
    1160                1165                1170

Pro Ser  Arg Phe Ser Gly Ser  Gly Ser Gly Thr Glu  Phe Thr Leu
    1175                1180                1185
```

-continued

```
Thr Ile  Ser Ser Leu Gln Pro  Asp Asp Phe Ala Thr  Tyr Tyr Cys
    1190                 1195                 1200

Gln Gly  Tyr Phe Tyr Phe Ile  Ser Arg Thr Tyr Val  Asn Ser Phe
    1205                 1210                 1215

Gly Gly  Gly Thr Lys Val Glu  Ile Lys
    1220                 1225


<210> SEQ ID NO 89
<211> LENGTH: 651
<212> TYPE: DNA
<213> ORGANISM: Artificial Sequence
<220> FEATURE:
<223> OTHER INFORMATION: Synthesized

<400> SEQUENCE: 89

gcctatgata tgacccagtc tccatcttcc gtgtctgcat ctgtaggaga cagagtcacc     60

atcaagtgtc aggccagtga ggacatttat agcttcttgg cctggtatca gcagaaacca    120

gggaaagccc ctaagctcct gatccattct gcatcctctc tggcatctgg ggtcccatca    180

aggttcagcg gcagtggatc tgggacagat ttcactctca ccatcagcag cctgcagcct    240

gaagattttg caacttacta ttgtcaacag ggttatggta aaaataatgt tgataatgct    300

ttcggcggag ggaccaaggt ggagatcaaa cgtacggtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg t             651


<210> SEQ ID NO 90
<211> LENGTH: 217
<212> TYPE: PRT
<213> ORGANISM: Artificial Sequence
<220> FEATURE:
<223> OTHER INFORMATION: Synthesized

<400> SEQUENCE: 90

Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
```

-continued

```
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 91
<211> LENGTH: 3687
<212> TYPE: DNA
<213> ORGANISM: Artificial Sequence
<220> FEATURE:
<223> OTHER INFORMATION: Synthesized

<400> SEQUENCE: 91

gacgtcgtga tgacccagtc tccttccacc ctgtctgcat ctgtaggaga cagagtcacc     60

atcaattgcc aagccagtga gagcattagc agttggttag cctggtatca gcagaaacca    120

gggaaagccc ctaagctcct gatctatgaa gcatccaaac tggcatctgg ggtcccatca    180

aggttcagcg gcagtggatc tgggacagaa tttactctca ccatcagcag cctgcagcct    240

gatgattttg caacttatta ctgccaaggc tatttttatt ttattagtcg tacttatgta    300

aattctttcg gcggagggac caaggtggag atcaaaggcg gtggcggtag tgggggaggc    360

ggttctggcg gcggagggtc cggcggtgga ggatcagagg tgcagctggt ggagtctggg    420

ggaggcttgg tccagcctgg ggggtccctg agactctcct gtgcagcctc tggattcacc    480

atcagtacca atgcaatgag ctgggtccgc caggctccag ggaaggggct ggagtggatc    540

ggagtcatta ctggtcgtga tatcacatac tacgcgagct gggcgaaagg cagattcacc    600

atctccagag acaattccaa gaacacgctg tatcttcaaa tgaacagcct gagagccgag    660

gacacggctg tgtattactg tgcgagagac ggtggttctt ctgctattac tagtaacaac    720

atttggggcc agggaaccct ggtcaccgtg tcgacaggcg gtggagggtc cggcggtggt    780

ggatcccagt cggtggagga gtctgggggga ggcttggtcc agcctggggg gtccctgaga    840

ctctcctgta ccgcctctgg aatcgacctt aatacctacg acatgatctg ggtccgccag    900

gctccaggca aggggctaga gtgggttgga atcattactt atagtggtag tagatactac    960

gcgaactggg cgaaaggccg attcaccatc tccaaagaca ataccaagaa cacggtgtat   1020

ctgcaaatga acagcctgag agctgaggac acggctgtgt attactgtgc gagagattat   1080

atgagtggtt cccacttgtg gggccaggga accctggtca ccgtctcttc agctagcacc   1140

aagggcccat cggtcttccc cctggcaccc tcctccaaga gcacctctgg gggcacagcg   1200

gccctgggct gcctggtcaa ggactacttc cccgaaccgg tgacggtgtc gtggaactca   1260

ggcgccctga ccagcggcgt gcacaccttc ccggctgtcc tacagtcctc aggactctac   1320

tccctcagca gcgtggtgac cgtgccctcc agcagcttgg gcacccagac ctacatctgc   1380

aacgtgaatc acaagcccag caacaccaag gtggacaaga gagttgagcc caaatcttgt   1440

gacaaaactc acacatgccc accgtgccca gcacctgaag ccgcgggggc accgtcagtc   1500

ttcctcttcc ccccaaaacc caaggacacc ctcatgatct cccggacccc tgaggtcaca   1560

tgcgtggtgg tggacgtgag ccacgaagac cctgaggtca agttcaactg gtacgtggac   1620

ggcgtggagg tgcataatgc caagacaaag ccgcgggagg agcagtacaa cagcacgtac   1680
```

```
cgtgtggtca gcgtcctcac cgtcctgcac caggactggc tgaatggcaa ggagtacaag   1740
tgcgcggtct ccaacaaagc cctcccagcc cccatcgaga aaaccatctc caaagccaaa   1800
gggcagcccc gagaaccaca ggtgtatacc ctgcccccat cccgggatga gctgaccaag   1860
aaccaggtca gcctgacctg cctggtcaaa ggcttctatc ccagcgacat cgccgtggag   1920
tgggagagca atgggcagcc ggagaacaac tacaagacca cgcctcccgt gctggactcc   1980
gacggctcct tcttcctcta tagcaagctc accgtggaca agagcaggtg gcagcagggg   2040
aacgtcttct catgctccgt gatgcatgag gctctgcaca accactacac gcagaagagc   2100
ctctccctgt ctccgggtgg cggtggaggg tccggcggtg gtgggtccgg agaggtgcag   2160
ctgttggagt ctgggggagg cttggtacag cctggggggt ccctgagact ctcctgtgca   2220
gcctctggat tcaccatcag tcgctaccac atgacttggg tccgccaggc tccagggaag   2280
gggctggagt ggatcggaca tatttatgtt aataatgatg acacagacta cgcgagctcc   2340
gcgaaaggcc ggttcaccat ctccagagac aattccaaga acacgctgta tctgcaaatg   2400
aacagcctga gagccgagga cacggccacc tatttctgtg cgagattgga tgttggtggt   2460
ggtggtgctt atattgggga catctggggc cagggaactc tggttaccgt ctcttcaggc   2520
ggtggcggta gtgggggagg cggttctggc ggcggagggt ccggcggtgg aggatcagac   2580
atccagatga cccagtctcc atcctccctg tctgcatctg taggagacag agtcaccatc   2640
acttgccagt ccagtcagag tgtttataac aacaacgact tagcctggta tcagcagaaa   2700
ccagggaaag ttcctaagct cctgatctat tatgcttcca ctctggcatc tggggtccca   2760
tctcggttca gtggcagtgg atctgggaca gatttcactc tcaccatcag cagcctgcag   2820
cctgaagatg ttgcaactta ttactgtgca ggcggttatg atacggatgg tcttgatacg   2880
tttgctttcg gcggagggac caaggtggag atcaaaggcg gtggagggtc cggcggtggt   2940
gggtccggac ggtcgctggt ggagtctggg ggaggcttgg tccagcctgg ggggtccctg   3000
agactctcct gtactgcctc tggattcacc atcagtagct accacatgca gtgggtccgc   3060
caggctccag ggaaggggct ggagtacatc ggaaccatta gtagtggtgg taatgtatac   3120
tacgcaagct ccgctagagg cagattcacc atctccagac cctcgtccaa gaacacggtg   3180
gatcttcaaa tgaacagcct gagagccgag gacacggctg tgtattactg tgcgagagac   3240
tctggttata gtgatcctat gtggggccag ggaaccctgg tcaccgtctc ttcaggcggt   3300
ggcggtagtg gggaggcgg ttctggcggc ggagggtccg gcggtggagg atcagacgtt   3360
gtgatgaccc agtctccatc ttccgtgtct gcatctgtag gagacagagt caccatcacc   3420
tgtcaggcca gtcagaacat taggacttac ttatcctggt atcagcagaa accagggaaa   3480
gcccctaagc tcctgatcta tgctgcagcc aatctggcat ctggggtccc atcaaggttc   3540
agcggcagtg gatctgggac agatttcact ctcaccatca gcgacctgga gcctggcgat   3600
gctgcaactt actattgtca gtctacctat cttggtactg attatgttgg cggtgctttc   3660
ggcggaggga ccaaggtgga gatcaaa                                      3687
```

<210> SEQ ID NO 92
<211> LENGTH: 1229
<212> TYPE: PRT
<213> ORGANISM: Artificial Sequence
<220> FEATURE:
<223> OTHER INFORMATION: Synthesized

<400> SEQUENCE: 92

```
Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Ile Ser Thr Asn Ala Met Ser Trp Val Arg Gln Ala Pro Gly Lys Gly
                165                 170                 175

Leu Glu Trp Ile Gly Val Ile Thr Gly Arg Asp Ile Thr Tyr Tyr Ala
            180                 185                 190

Ser Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Gly Gly Ser Ser Ala Ile Thr Ser Asn Asn
225                 230                 235                 240

Ile Trp Gly Gln Gly Thr Leu Val Thr Val Ser Thr Gly Gly Gly Gly
                245                 250                 255

Ser Gly Gly Gly Gly Ser Gln Ser Val Glu Glu Ser Gly Gly Gly Leu
            260                 265                 270

Val Gln Pro Gly Gly Ser Leu Arg Leu Ser Cys Thr Ala Ser Gly Ile
        275                 280                 285

Asp Leu Asn Thr Tyr Asp Met Ile Trp Val Arg Gln Ala Pro Gly Lys
    290                 295                 300

Gly Leu Glu Trp Val Gly Ile Ile Thr Tyr Ser Gly Ser Arg Tyr Tyr
305                 310                 315                 320

Ala Asn Trp Ala Lys Gly Arg Phe Thr Ile Ser Lys Asp Asn Thr Lys
                325                 330                 335

Asn Thr Val Tyr Leu Gln Met Asn Ser Leu Arg Ala Glu Asp Thr Ala
            340                 345                 350

Val Tyr Tyr Cys Ala Arg Asp Tyr Met Ser Gly Ser His Leu Trp Gly
        355                 360                 365

Gln Gly Thr Leu Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
```

```
            420                 425                 430

Val Leu Gln Ser Ser Gly Leu Tyr Ser Leu Ser Ser Val Val Thr Val
        435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Arg Val Glu Pro Lys Ser Cys
465                 470                 475                 480

Asp Lys Thr His Thr Cys Pro Pro Cys Pro Ala Pro Glu Ala Ala Gly
                485                 490                 495

Ala Pro Ser Val Phe Leu Phe Pro Pro Lys Pro Lys Asp Thr Leu Met
            500                 505                 510

Ile Ser Arg Thr Pro Glu Val Thr Cys Val Val Val Asp Val Ser His
        515                 520                 525

Glu Asp Pro Glu Val Lys Phe Asn Trp Tyr Val Asp Gly Val Glu Val
    530                 535                 540

His Asn Ala Lys Thr Lys Pro Arg Glu Glu Gln Tyr Asn Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Ala Val Ser Asn Lys Ala Leu Pro Ala Pro Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Arg Asp Glu Leu Thr Lys Asn Gln Val Ser
    610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
        675                 680                 685

His Glu Ala Leu His Asn His Tyr Thr Gln Lys Ser Leu Ser Leu Ser
    690                 695                 700

Pro Gly Gly Gly Gly Gly Ser Gly Gly Gly Gly Ser Gly Glu Val Gln
705                 710                 715                 720

Leu Leu Glu Ser Gly Gly Gly Leu Val Gln Pro Gly Gly Ser Leu Arg
                725                 730                 735

Leu Ser Cys Ala Ala Ser Gly Phe Thr Ile Ser Arg Tyr His Met Thr
            740                 745                 750

Trp Val Arg Gln Ala Pro Gly Lys Gly Leu Glu Trp Ile Gly His Ile
        755                 760                 765

Tyr Val Asn Asn Asp Asp Thr Asp Tyr Ala Ser Ser Ala Lys Gly Arg
    770                 775                 780

Phe Thr Ile Ser Arg Asp Asn Ser Lys Asn Thr Leu Tyr Leu Gln Met
785                 790                 795                 800

Asn Ser Leu Arg Ala Glu Asp Thr Ala Thr Tyr Phe Cys Ala Arg Leu
                805                 810                 815

Asp Val Gly Gly Gly Gly Ala Tyr Ile Gly Asp Ile Trp Gly Gln Gly
            820                 825                 830

Thr Leu Val Thr Val Ser Ser Gly Gly Gly Gly Ser Gly Gly Gly Gly
        835                 840                 845
```

```
Ser Gly Gly Gly Gly Ser Gly Gly Gly Gly Ser Asp Ile Gln Met Thr
    850                 855                 860

Gln Ser Pro Ser Ser Leu Ser Ala Ser Val Gly Asp Arg Val Thr Ile
865                 870                 875                 880

Thr Cys Gln Ser Ser Gln Ser Val Tyr Asn Asn Asn Asp Leu Ala Trp
                885                 890                 895

Tyr Gln Gln Lys Pro Gly Lys Val Pro Lys Leu Leu Ile Tyr Tyr Ala
            900                 905                 910

Ser Thr Leu Ala Ser Gly Val Pro Ser Arg Phe Ser Gly Ser Gly Ser
        915                 920                 925

Gly Thr Asp Phe Thr Leu Thr Ile Ser Ser Leu Gln Pro Glu Asp Val
    930                 935                 940

Ala Thr Tyr Tyr Cys Ala Gly Gly Tyr Asp Thr Asp Gly Leu Asp Thr
945                 950                 955                 960

Phe Ala Phe Gly Gly Gly Thr Lys Val Glu Ile Lys Gly Gly Gly Gly
                965                 970                 975

Ser Gly Gly Gly Gly Ser Gly Arg Ser Leu Val Glu Ser Gly Gly Gly
            980                 985                 990

Leu Val Gln Pro Gly Gly Ser Leu  Arg Leu Ser Cys Thr  Ala Ser Gly
        995                 1000                1005

Phe Thr  Ile Ser Ser Tyr His  Met Gln Trp Val Arg  Gln Ala Pro
    1010                 1015                 1020

Gly Lys  Gly Leu Glu Tyr Ile  Gly Thr Ile Ser Ser  Gly Gly Asn
    1025                 1030                 1035

Val Tyr  Tyr Ala Ser Ser Ala  Arg Gly Arg Phe Thr  Ile Ser Arg
    1040                 1045                 1050

Pro Ser  Ser Lys Asn Thr Val  Asp Leu Gln Met Asn  Ser Leu Arg
    1055                 1060                 1065

Ala Glu  Asp Thr Ala Val Tyr  Tyr Cys Ala Arg Asp  Ser Gly Tyr
    1070                 1075                 1080

Ser Asp  Pro Met Trp Gly Gln  Gly Thr Leu Val Thr  Val Ser Ser
    1085                 1090                 1095

Gly Gly  Gly Gly Ser Gly Gly  Gly Gly Ser Gly Gly  Gly Gly Ser
    1100                 1105                 1110

Gly Gly  Gly Gly Ser Asp Val  Val Met Thr Gln Ser  Pro Ser Ser
    1115                 1120                 1125

Val Ser  Ala Ser Val Gly Asp  Arg Val Thr Ile Thr  Cys Gln Ala
    1130                 1135                 1140

Ser Gln  Asn Ile Arg Thr Tyr  Leu Ser Trp Tyr Gln  Gln Lys Pro
    1145                 1150                 1155

Gly Lys  Ala Pro Lys Leu Leu  Ile Tyr Ala Ala Ala  Asn Leu Ala
    1160                 1165                 1170

Ser Gly  Val Pro Ser Arg Phe  Ser Gly Ser Gly Ser  Gly Thr Asp
    1175                 1180                 1185

Phe Thr  Leu Thr Ile Ser Asp  Leu Glu Pro Gly Asp  Ala Ala Thr
    1190                 1195                 1200

Tyr Tyr  Cys Gln Ser Thr Tyr  Leu Gly Thr Asp Tyr  Val Gly Gly
    1205                 1210                 1215

Ala Phe  Gly Gly Gly Thr Lys  Val Glu Ile Lys
    1220                 1225
```

<210> SEQ ID NO 93
<211> LENGTH: 651

<212> TYPE: DNA
<213> ORGANISM: Artificial Sequence
<220> FEATURE:
<223> OTHER INFORMATION: Synthesized

<400> SEQUENCE: 93
gcctatgata tgacccagtc tccatcttcc gtgtctgcat ctgtaggaga cagagtcacc 60
atcaagtgtc aggccagtga ggacatttat agcttcttgg cctggtatca gcagaaacca 120
gggaaagccc ctaagctcct gatccattct gcatcctctc tggcatctgg ggtcccatca 180
aggttcagcg gcagtggatc tgggacagat ttcactctca ccatcagcag cctgcagcct 240
gaagattttg caacttacta ttgtcaacag ggttatggta aaaataatgt tgataatgct 300
ttcggcggag ggaccaaggt ggagatcaaa cgtacggtgg ctgcaccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 94
<211> LENGTH: 217
<212> TYPE: PRT
<213> ORGANISM: Artificial Sequence
<220> FEATURE:
<223> OTHER INFORMATION: Synthesized

<400> SEQUENCE: 94

```
Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
```

210 215

<210> SEQ ID NO 95
<211> LENGTH: 3675
<212> TYPE: DNA
<213> ORGANISM: Artificial Sequence
<220> FEATURE:
<223> OTHER INFORMATION: Synthesized

<400> SEQUENCE: 95
gacgtcgtga tgacccagtc tccttccacc ctgtctgcat ctgtaggaga cagagtcacc 60
atcaattgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagaa tttactctca ccatcagcag cctgcagcct 240
gatgattttg caacttatta ctgccaaggc tatttttatt ttattagtcg tacttatgta 300
aattctttcg gcggagggac caaggtggag atcaaaggcg gtggcggtag tgggggaggc 360
ggttctggcg gcggagggtc cggcggtgga ggatcagagg tgcagctggt ggagtctggg 420
ggaggcttgg tccagcctgg ggggtccctg agactctcct gtgcagcctc tggattcacc 480
atcagtacca atgcaatgag ctgggtccgc caggctccag ggaaggggct ggagtggatc 540
ggagtcatta ctggtcgtga tatcacatac tacgcgagct gggcgaaagg cagattcacc 600
atctccagag acaattccaa gaacacgctg tatcttcaaa tgaacagcct gagagccgag 660
gacacggctg tgtattactg tgcgagagac ggtggttctt ctgctattac tagtaacaac 720
atttggggcc agggaaccct ggtcaccgtg tcgacaggcg gtggagggtc cggcggtggt 780
ggatccgagg tgcagctgtt ggagtctggg ggaggcttgg tacagcctgg ggggtccctg 840
agactctcct gtgcagcctc tggattcacc atcagtcgct accacatgac ttgggtccgc 900
caggctccag ggaaggggct ggagtggatc ggacatattt atgttaataa tgatgacaca 960
gactacgcga gctccgcgaa aggccggttc accatctcca gagacaattc caagaacacg 1020
ctgtatctgc aaatgaacag cctgagagcc gaggacacgg ccacctattt ctgtgcgaga 1080
ttggatgttg gtggtggtgg tgcttatatt ggggacatct ggggccaggg aaccctggtc 1140
accgtctcga gcgctagcac caagggccca tcggtcttcc ccctggcacc ctcctccaag 1200
agcacctctg ggggcacagc ggccctgggc tgcctggtca aggactactt ccccgaaccg 1260
gtgacggtgt cgtggaactc aggcgccctg accagcggcg tgcacacctt cccggctgtc 1320
ctacagtcct caggactcta ctccctcagc agcgtggtga ccgtgccctc cagcagcttg 1380
ggcacccaga cctacatctg caacgtgaat cacaagccca gcaacaccaa ggtggacaag 1440
agagttgagc ccaaatcttg tgacaaaact cacacatgcc caccgtgccc agcacctgaa 1500
gccgcggggg caccgtcagt cttcctcttc cccccaaaac ccaaggacac cctcatgatc 1560
tcccggaccc ctgaggtcac atgcgtggtg gtggacgtga gccacgaaga ccctgaggtc 1620
aagttcaact ggtacgtgga cggcgtggag gtgcataatg ccaagacaaa gccgcgggag 1680
gagcagtaca acagcacgta ccgtgtggtc agcgtcctca ccgtcctgca ccaggactgg 1740
ctgaatggca aggagtacaa gtgcgcggtc tccaacaaag ccctcccagc ccccatcgag 1800
aaaaccatct ccaaagccaa agggcagccc cgagaaccac aggtgtatac cctgccccca 1860
tcccgggatg agctgaccaa gaaccaggtc agcctgacct gcctggtcaa aggcttctat 1920
cccagcgaca tcgccgtgga gtgggagagc aatgggcagc cggagaacaa ctacaagacc 1980
acgcctcccg tgctggactc cgacggctcc ttcttcctct atagcaagct caccgtggac 2040
aagagcaggt ggcagcaggg gaacgtcttc tcatgctccg tgatgcatga ggctctgcac 2100
aaccactaca cgcagaagag cctctccctg tctccgggtg gcggtggagg gtccggcggt 2160
ggtggatccc agtcggtgga ggagtctggg ggaggcttgg tccagcctgg ggggtccctg 2220
agactctcct gtaccgcctc tggaatcgac cttaatacct acgacatgat ctgggtccgc 2280
caggctccag gcaaggggct agagtgggtt ggaatcatta cttatagtgg tagtagatac 2340
tacgcgaact gggcgaaagg ccgattcacc atctccaaag acaataccaa gaacacggtg 2400
tatctgcaaa tgaacagcct gagagctgag gacacggctg tgtattactg tgcgagagat 2460
tatatgagtg gttcccactt gtggggccag ggaaccctgg tcaccgtctc ttccggtgga 2520
ggcggttcag gcggaggtgg aagtggtggt ggcggctctg gaggcggcgg atctgcctat 2580
gatatgaccc agtctccatc ttccgtgtct gcatctgtag gagacagagt caccatcaag 2640
tgtcaggcca gtgaggacat ttatagcttc ttggcctggt atcagcagaa accagggaaa 2700
gcccctaagc tcctgatcca ttctgcatcc tctctggcat ctggggtccc atcaaggttc 2760
agcggcagtg gatctgggac agatttcact ctcaccatca gcagcctgca gcctgaagat 2820
tttgcaactt actattgtca acagggttat ggtaaaaata atgttgataa tgctttcggc 2880
ggagggacca aggtggagat caaaggcggt ggagggtccg gcggtggtgg gtccggacgg 2940
tcgctggtgg agtctggggg aggcttggtc cagcctgggg ggtccctgag actctcctgt 3000
actgcctctg gattcaccat cagtagctac cacatgcagt gggtccgcca ggctccaggg 3060
aaggggctgg agtacatcgg aaccattagt agtggtggta atgtatacta cgcaagctcc 3120
gctagaggca gattcaccat ctccagaccc tcgtccaaga acacggtgga tcttcaaatg 3180
aacagcctga gagccgagga cacggctgtg tattactgtg cgagagactc tggttatagt 3240
gatcctatgt ggggccaggg aaccctggtc accgtctctt caggcggtgg cggtagtggg 3300
ggaggcggtt ctggcggcgg agggtccggc ggtggaggat cagacgttgt gatgacccag 3360
tctccatctt ccgtgtctgc atctgtagga gacagagtca ccatcacctg tcaggccagt 3420
cagaacatta ggacttactt atcctggtat cagcagaaac cagggaaagc ccctaagctc 3480
ctgatctatg ctgcagccaa tctggcatct ggggtcccat caaggttcag cggcagtgga 3540
tctgggacag atttcactct caccatcagc gacctggagc ctggcgatgc tgcaacttac 3600
tattgtcagt ctacctatct tggtactgat tatgttggcg gtgctttcgg cggagggacc 3660
aaggtggaga tcaaa 3675

<210> SEQ ID NO 96
<211> LENGTH: 1225
<212> TYPE: PRT
<213> ORGANISM: Artificial Sequence
<220> FEATURE:
<223> OTHER INFORMATION: Synthesized

<400> SEQUENCE: 96

Asp Val Val Met Thr Gln Ser Pro Ser Thr Leu Ser Ala Ser Val Gly
1 5 10 15

Asp Arg Val Thr Ile Asn Cys Gln Ala Ser Glu Ser Ile Ser Ser Trp
20 25 30

Leu Ala Trp Tyr Gln Gln Lys Pro Gly Lys Ala Pro Lys Leu Leu Ile
35 40 45

Tyr Glu Ala Ser Lys Leu Ala Ser Gly Val Pro Ser Arg Phe Ser Gly
50 55 60

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Ile Ser Thr Asn Ala Met Ser Trp Val Arg Gln Ala Pro Gly Lys Gly
                165                 170                 175

Leu Glu Trp Ile Gly Val Ile Thr Gly Arg Asp Ile Thr Tyr Tyr Ala
            180                 185                 190

Ser Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Gly Gly Ser Ser Ala Ile Thr Ser Asn Asn
225                 230                 235                 240

Ile Trp Gly Gln Gly Thr Leu Val Thr Val Ser Thr Gly Gly Gly Gly
                245                 250                 255

Ser Gly Gly Gly Gly Ser Glu Val Gln Leu Leu Glu Ser Gly Gly Gly
            260                 265                 270

Leu Val Gln Pro Gly Gly Ser Leu Arg Leu Ser Cys Ala Ala Ser Gly
        275                 280                 285

Phe Thr Ile Ser Arg Tyr His Met Thr Trp Val Arg Gln Ala Pro Gly
    290                 295                 300

Lys Gly Leu Glu Trp Ile Gly His Ile Tyr Val Asn Asn Asp Asp Thr
305                 310                 315                 320

Asp Tyr Ala Ser Ser Ala Lys Gly Arg Phe Thr Ile Ser Arg Asp Asn
                325                 330                 335

Ser Lys Asn Thr Leu Tyr Leu Gln Met Asn Ser Leu Arg Ala Glu Asp
            340                 345                 350

Thr Ala Thr Tyr Phe Cys Ala Arg Leu Asp Val Gly Gly Gly Gly Ala
        355                 360                 365

Tyr Ile Gly Asp Ile Trp Gly Gln Gly Thr Leu Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Arg Val Glu Pro Lys Ser Cys Asp Lys Thr His Thr Cys Pro Pro Cys
```

-continued

```
                485                 490                 495

Pro Ala Pro Glu Ala Ala Gly Ala Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Ala Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Asp Glu
    610                 615                 620

Leu Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Gly Gly Gly Gly Ser Gly Gly
705                 710                 715                 720

Gly Gly Ser Gln Ser Val Glu Glu Ser Gly Gly Gly Leu Val Gln Pro
                725                 730                 735

Gly Gly Ser Leu Arg Leu Ser Cys Thr Ala Ser Gly Ile Asp Leu Asn
            740                 745                 750

Thr Tyr Asp Met Ile Trp Val Arg Gln Ala Pro Gly Lys Gly Leu Glu
        755                 760                 765

Trp Val Gly Ile Ile Thr Tyr Ser Gly Ser Arg Tyr Tyr Ala Asn Trp
    770                 775                 780

Ala Lys Gly Arg Phe Thr Ile Ser Lys Asp Asn Thr Lys Asn Thr Val
785                 790                 795                 800

Tyr Leu Gln Met Asn Ser Leu Arg Ala Glu Asp Thr Ala Val Tyr Tyr
                805                 810                 815

Cys Ala Arg Asp Tyr Met Ser Gly Ser His Leu Trp Gly Gln Gly Thr
            820                 825                 830

Leu Val Thr Val Ser Ser Gly Gly Gly Gly Ser Gly Gly Gly Gly Ser
        835                 840                 845

Gly Gly Gly Gly Ser Gly Gly Gly Gly Ser Ala Tyr Asp Met Thr Gln
    850                 855                 860

Ser Pro Ser Ser Val Ser Ala Ser Val Gly Asp Arg Val Thr Ile Lys
865                 870                 875                 880

Cys Gln Ala Ser Glu Asp Ile Tyr Ser Phe Leu Ala Trp Tyr Gln Gln
                885                 890                 895

Lys Pro Gly Lys Ala Pro Lys Leu Leu Ile His Ser Ala Ser Ser Leu
            900                 905                 910
```

```
Ala Ser Gly Val Pro Ser Arg Phe Ser Gly Ser Gly Ser Gly Thr Asp
        915                 920                 925

Phe Thr Leu Thr Ile Ser Ser Leu Gln Pro Glu Asp Phe Ala Thr Tyr
    930                 935                 940

Tyr Cys Gln Gln Gly Tyr Gly Lys Asn Asn Val Asp Asn Ala Phe Gly
945                 950                 955                 960

Gly Gly Thr Lys Val Glu Ile Lys Gly Gly Gly Gly Ser Gly Gly Gly
                965                 970                 975

Gly Ser Gly Arg Ser Leu Val Glu Ser Gly Gly Gly Leu Val Gln Pro
            980                 985                 990

Gly Gly Ser Leu Arg Leu Ser Cys  Thr Ala Ser Gly Phe  Thr Ile Ser
        995                 1000                1005

Ser Tyr  His Met Gln Trp Val  Arg Gln Ala Pro Gly  Lys Gly Leu
    1010                 1015                 1020

Glu Tyr  Ile Gly Thr Ile Ser  Ser Gly Gly Asn Val  Tyr Tyr Ala
    1025                 1030                 1035

Ser Ser  Ala Arg Gly Arg Phe  Thr Ile Ser Arg Pro  Ser Ser Lys
    1040                 1045                 1050

Asn Thr  Val Asp Leu Gln Met  Asn Ser Leu Arg Ala  Glu Asp Thr
    1055                 1060                 1065

Ala Val  Tyr Tyr Cys Ala Arg  Asp Ser Gly Tyr Ser  Asp Pro Met
    1070                 1075                 1080

Trp Gly  Gln Gly Thr Leu Val  Thr Val Ser Ser Gly  Gly Gly Gly
    1085                 1090                 1095

Ser Gly  Gly Gly Gly Ser Gly  Gly Gly Gly Ser Gly  Gly Gly Gly
    1100                 1105                 1110

Ser Asp  Val Val Met Thr Gln  Ser Pro Ser Ser Val  Ser Ala Ser
    1115                 1120                 1125

Val Gly  Asp Arg Val Thr Ile  Thr Cys Gln Ala Ser  Gln Asn Ile
    1130                 1135                 1140

Arg Thr  Tyr Leu Ser Trp Tyr  Gln Gln Lys Pro Gly  Lys Ala Pro
    1145                 1150                 1155

Lys Leu  Leu Ile Tyr Ala Ala  Ala Asn Leu Ala Ser  Gly Val Pro
    1160                 1165                 1170

Ser Arg  Phe Ser Gly Ser Gly  Ser Gly Thr Asp Phe  Thr Leu Thr
    1175                 1180                 1185

Ile Ser  Asp Leu Glu Pro Gly  Asp Ala Ala Thr Tyr  Tyr Cys Gln
    1190                 1195                 1200

Ser Thr  Tyr Leu Gly Thr Asp  Tyr Val Gly Gly Ala  Phe Gly Gly
    1205                 1210                 1215

Gly Thr  Lys Val Glu Ile Lys
    1220                 1225
```

<210> SEQ ID NO 97
<211> LENGTH: 660
<212> TYPE: DNA
<213> ORGANISM: Artificial Sequence
<220> FEATURE:
<223> OTHER INFORMATION: Synthesized

<400> SEQUENCE: 97

```
gacatccaga tgacccagtc tccatcctcc ctgtctgcat ctgtaggaga cagagtcacc     60

atcacttgcc agtccagtca gagtgtttat aacaacaacg acttagcctg gtatcagcag    120

aaaccaggga aagttcctaa gctcctgatc tattatgcat ccactctggc atctggggtc    180
```

```
ccatctcggt tcagtggcag tggatctggg acagatttca ctctcaccat cagcagcctg    240

cagcctgaag atgttgcaac ttattactgt gcaggcggtt atgatacgga tggtcttgat    300

acgtttgctt tcggcggagg gaccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 98
<211> LENGTH: 220
<212> TYPE: PRT
<213> ORGANISM: Artificial Sequence
<220> FEATURE:
<223> OTHER INFORMATION: Synthesized

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Asp Thr
                85                  90                  95

Asp Gly Leu Asp Thr Phe Ala Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 99
<211> LENGTH: 3696
<212> TYPE: DNA
<213> ORGANISM: Artificial Sequence
<220> FEATURE:
<223> OTHER INFORMATION: Synthesized

<400> SEQUENCE: 99

-continued

```
gacgtcgtga tgacccagtc tccttccacc ctgtctgcat ctgtaggaga cagagtcacc     60
atcaattgcc aagccagtga gagcattagc agttggttag cctggtatca gcagaaacca    120
gggaaagccc ctaagctcct gatctatgaa gcatccaaac tggcatctgg ggtcccatca    180
aggttcagcg gcagtggatc tgggacagaa tttactctca ccatcagcag cctgcagcct    240
gatgattttg caacttatta ctgccaaggc tatttttatt ttattagtcg tacttatgta    300
aattctttcg gcggagggac caaggtggag atcaaaggcg gtggcggtag tgggggaggc    360
ggttctggcg gcggagggtc cggcggtgga ggatcagagg tgcagctggt ggagtctggg    420
ggaggcttgg tccagcctgg ggggtccctg agactctcct gtgcagcctc tggattcacc    480
atcagtacca atgcaatgag ctgggtccgc caggctccag ggaaggggct ggagtggatc    540
ggagtcatta ctggtcgtga tatcacatac tacgcgagct gggcgaaagg cagattcacc    600
atctccagag acaattccaa gaacacgctg tatcttcaaa tgaacagcct gagagccgag    660
gacacggctg tgtattactg tgcgagagac ggtggttctt ctgctattac tagtaacaac    720
atttggggcc agggaaccct ggtcaccgtg tcgacaggcg gtggagggtc cggcggtggt    780
ggatcagagg tgcagctgtt ggagtctggg ggaggcttgg tacagcctgg ggggtccctg    840
agactctcct gtgcagcctc tggattcacc atcagtcgct accacatgac ttgggtccgc    900
caggctccag ggaaggggct ggagtggatc ggacatattt atgttaataa tgatgacaca    960
gactacgcga gctccgcgaa aggccggttc accatctcca gagacaattc caagaacacg   1020
ctgtatctgc aaatgaacag cctgagagcc gaggacacgg ccacctattt ctgtgcgaga   1080
ttggatgttg gtggtggtgg tgcttatatt ggggacatct ggggccaggg aactctggtt   1140
accgtctctt cagctagcac caagggccca tcggtcttcc ccctggcacc ctcctccaag   1200
agcacctctg ggggcacagc ggccctgggc tgcctggtca aggactactt ccccgaaccg   1260
gtgacggtgt cgtggaactc aggcgccctg accagcggcg tgcacacctt cccggctgtc   1320
ctacagtcct caggactcta ctccctcagc agcgtggtga ccgtgccctc cagcagcttg   1380
ggcacccaga cctacatctg caacgtgaat cacaagccca gcaacaccaa ggtggacaag   1440
agagttgagc ccaaatcttg tgacaaaact cacacatgcc caccgtgccc agcacctgaa   1500
gccgcggggg caccgtcagt cttcctcttc cccccaaaac ccaaggacac cctcatgatc   1560
tcccggaccc ctgaggtcac atgcgtggtg gtggacgtga gccacgaaga ccctgaggtc   1620
aagttcaact ggtacgtgga cggcgtggag gtgcataatg ccaagacaaa gccgcgggag   1680
gagcagtaca acagcacgta ccgtgtggtc agcgtcctca ccgtcctgca ccaggactgg   1740
ctgaatggca aggagtacaa gtgcgcggtc tccaacaaag ccctcccagc ccccatcgag   1800
aaaaccatct ccaaagccaa agggcagccc cgagaaccac aggtgtacac cctgccccca   1860
tcccgggatg agctgaccaa gaaccaggtc agcctgacct gcctggtcaa aggcttctat   1920
cccagcgaca tcgccgtgga gtgggagagc aatgggcagc cggagaacaa ctacaagacc   1980
acgcctcccg tgctggactc cgacggctcc ttcttcctct atagcaagct caccgtggac   2040
aagagcaggt ggcagcaggg gaacgtcttc tcatgctccg tgatgcatga ggctctgcac   2100
aaccactaca cgcagaagag cctctccctg tctccgggtg gcggtggagg gtccggcggt   2160
ggtggatccg aggtgcagct gttggagtct gggggaggct tggtacagcc tggggggtcc   2220
ctgagactct cctgtgcagc ctctggattc tccttcagta gcgggtacga catgtgctgg   2280
gtccgccagg ctccagggaa ggggctggag tggatcgcat gcattgctgc tggtagtgct   2340
ggtatcactt acgacgcgaa ctgggcgaaa ggccggttca ccatctccag agacaattcc   2400
```

```
aagaacacgc tgtatctgca aatgaacagc ctgagagccg aggacacggc cgtatattac   2460

tgtgcgagat cggcgttttc gttcgactac gccatggacc tctggggcca gggaaccctg   2520

gtcaccgtct cgagcggtgg aggcggatct ggcggaggtg gttccggcgg tggcggctcc   2580

ggtggaggcg gctctgacat ccagatgacc cagtctcctt ccaccctgtc tgcatctgta   2640

ggagacagag tcaccatcac ttgccaggcc agtcagagca ttagttccca cttaaactgg   2700

tatcagcaga aaccagggaa agcccctaag ctcctgatct ataaggcatc cactctggca   2760

tctggggtcc catcaaggtt cagcggcagt ggatctggga cagaatttac tctcaccatc   2820

agcagcctgc agcctgatga ttttgcaact tattactgcc aacagggtta tagttggggt   2880

aatgttgata atgttttcgg cggagggacc aaggtggaga tcaaaggcgg tggagggtcc   2940

ggcggtggtg gctccggacg gtcgctggtg gagtctgggg gaggcttggt ccagcctggg   3000

gggtccctga gactctcctg tactgcctct ggattcacca tcagtagcta ccacatgcag   3060

tgggtccgcc aggctccagg gaaggggctg gagtacatcg gaaccattag tagtggtggt   3120

aatgtatact acgcaagctc cgctagaggc agattcacca tctccagacc ctcgtccaag   3180

aacacggtgg atcttcaaat gaacagcctg agagccgagg acacggctgt gtattactgt   3240

gcgagagact ctggttatag tgatcctatg tggggccagg gaaccctggt caccgtctct   3300

tcaggcggtg gcggtagtgg gggaggcggt tctggcggcg gagggtccgg cggtggagga   3360

tcagacgttg tgatgaccca gtctccatct tccgtgtctg catctgtagg agacagagtc   3420

accatcacct gtcaggccag tcagaacatt aggacttact tatcctggta tcagcagaaa   3480

ccagggaaag cccctaagct cctgatctat gctgcagcca atctggcatc tggggtccca   3540

tcaaggttca gcggcagtgg atctgggaca gatttcactc tcaccatcag cgacctggag   3600

cctggcgatg ctgcaactta ctattgtcag tctacctatc ttggtactga ttatgttggc   3660

ggtgctttcg gcggagggac caaggtggag atcaaa                             3696
```

<210> SEQ ID NO 100
<211> LENGTH: 1232
<212> TYPE: PRT
<213> ORGANISM: Artificial Sequence
<220> FEATURE:
<223> OTHER INFORMATION: Synthesized

<400> SEQUENCE: 100

```
Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125
```

-continued

```
Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Ile Ser Thr Asn Ala Met Ser Trp Val Arg Gln Ala Pro Gly Lys Gly
                165                 170                 175

Leu Glu Trp Ile Gly Val Ile Thr Gly Arg Asp Ile Thr Tyr Tyr Ala
            180                 185                 190

Ser Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Gly Gly Ser Ser Ala Ile Thr Ser Asn Asn
225                 230                 235                 240

Ile Trp Gly Gln Gly Thr Leu Val Thr Val Ser Thr Gly Gly Gly Gly
                245                 250                 255

Ser Gly Gly Gly Gly Ser Glu Val Gln Leu Leu Glu Ser Gly Gly Gly
            260                 265                 270

Leu Val Gln Pro Gly Gly Ser Leu Arg Leu Ser Cys Ala Ala Ser Gly
        275                 280                 285

Phe Thr Ile Ser Arg Tyr His Met Thr Trp Val Arg Gln Ala Pro Gly
    290                 295                 300

Lys Gly Leu Glu Trp Ile Gly His Ile Tyr Val Asn Asn Asp Asp Thr
305                 310                 315                 320

Asp Tyr Ala Ser Ser Ala Lys Gly Arg Phe Thr Ile Ser Arg Asp Asn
                325                 330                 335

Ser Lys Asn Thr Leu Tyr Leu Gln Met Asn Ser Leu Arg Ala Glu Asp
            340                 345                 350

Thr Ala Thr Tyr Phe Cys Ala Arg Leu Asp Val Gly Gly Gly Gly Ala
        355                 360                 365

Tyr Ile Gly Asp Ile Trp Gly Gln Gly Thr Leu Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Arg Val Glu Pro Lys Ser Cys Asp Lys Thr His Thr Cys Pro Pro Cys
                485                 490                 495

Pro Ala Pro Glu Ala Ala Gly Ala Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
```

545 550 555 560

Glu Gln Tyr Asn Ser Thr Tyr Arg Val Val Ser Val Leu Thr Val Leu
565 570 575

His Gln Asp Trp Leu Asn Gly Lys Glu Tyr Lys Cys Ala Val Ser Asn
580 585 590

Lys Ala Leu Pro Ala Pro Ile Glu Lys Thr Ile Ser Lys Ala Lys Gly
595 600 605

Gln Pro Arg Glu Pro Gln Val Tyr Thr Leu Pro Pro Ser Arg Asp Glu
610 615 620

Leu Thr Lys Asn Gln Val Ser Leu Thr Cys Leu Val Lys Gly Phe Tyr
625 630 635 640

Pro Ser Asp Ile Ala Val Glu Trp Glu Ser Asn Gly Gln Pro Glu Asn
645 650 655

Asn Tyr Lys Thr Thr Pro Pro Val Leu Asp Ser Asp Gly Ser Phe Phe
660 665 670

Leu Tyr Ser Lys Leu Thr Val Asp Lys Ser Arg Trp Gln Gln Gly Asn
675 680 685

Val Phe Ser Cys Ser Val Met His Glu Ala Leu His Asn His Tyr Thr
690 695 700

Gln Lys Ser Leu Ser Leu Ser Pro Gly Gly Gly Gly Gly Ser Gly Gly
705 710 715 720

Gly Gly Ser Glu Val Gln Leu Leu Glu Ser Gly Gly Gly Leu Val Gln
725 730 735

Pro Gly Gly Ser Leu Arg Leu Ser Cys Ala Ala Ser Gly Phe Ser Phe
740 745 750

Ser Ser Gly Tyr Asp Met Cys Trp Val Arg Gln Ala Pro Gly Lys Gly
755 760 765

Leu Glu Trp Ile Ala Cys Ile Ala Ala Gly Ser Ala Gly Ile Thr Tyr
770 775 780

Asp Ala Asn Trp Ala Lys Gly Arg Phe Thr Ile Ser Arg Asp Asn Ser
785 790 795 800

Lys Asn Thr Leu Tyr Leu Gln Met Asn Ser Leu Arg Ala Glu Asp Thr
805 810 815

Ala Val Tyr Tyr Cys Ala Arg Ser Ala Phe Ser Phe Asp Tyr Ala Met
820 825 830

Asp Leu Trp Gly Gln Gly Thr Leu Val Thr Val Ser Ser Gly Gly Gly
835 840 845

Gly Ser Gly Gly Gly Gly Ser Gly Gly Gly Gly Ser Gly Gly Gly Gly
850 855 860

Ser Asp Ile Gln Met Thr Gln Ser Pro Ser Thr Leu Ser Ala Ser Val
865 870 875 880

Gly Asp Arg Val Thr Ile Thr Cys Gln Ala Ser Gln Ser Ile Ser Ser
885 890 895

His Leu Asn Trp Tyr Gln Gln Lys Pro Gly Lys Ala Pro Lys Leu Leu
900 905 910

Ile Tyr Lys Ala Ser Thr Leu Ala Ser Gly Val Pro Ser Arg Phe Ser
915 920 925

Gly Ser Gly Ser Gly Thr Glu Phe Thr Leu Thr Ile Ser Ser Leu Gln
930 935 940

Pro Asp Asp Phe Ala Thr Tyr Tyr Cys Gln Gln Gly Tyr Ser Trp Gly
945 950 955 960

Asn Val Asp Asn Val Phe Gly Gly Gly Thr Lys Val Glu Ile Lys Gly
965 970 975

```
Gly Gly Gly Ser Gly Gly Gly Gly Ser Gly Arg Ser Leu Val Glu Ser
            980                 985                 990

Gly Gly Gly Leu Val Gln Pro Gly  Gly Ser Leu Arg Leu  Ser Cys Thr
        995                 1000                 1005

Ala Ser  Gly Phe Thr Ile Ser  Ser Tyr His Met Gln  Trp Val Arg
    1010                 1015                 1020

Gln Ala  Pro Gly Lys Gly Leu  Glu Tyr Ile Gly Thr  Ile Ser Ser
    1025                 1030                 1035

Gly Gly  Asn Val Tyr Tyr Ala  Ser Ser Ala Arg Gly  Arg Phe Thr
    1040                 1045                 1050

Ile Ser  Arg Pro Ser Ser Lys  Asn Thr Val Asp Leu  Gln Met Asn
    1055                 1060                 1065

Ser Leu  Arg Ala Glu Asp Thr  Ala Val Tyr Tyr Cys  Ala Arg Asp
    1070                 1075                 1080

Ser Gly  Tyr Ser Asp Pro Met  Trp Gly Gln Gly Thr  Leu Val Thr
    1085                 1090                 1095

Val Ser  Ser Gly Gly Gly Gly  Ser Gly Gly Gly Gly  Ser Gly Gly
    1100                 1105                 1110

Gly Gly  Ser Gly Gly Gly Gly  Ser Asp Val Val Met  Thr Gln Ser
    1115                 1120                 1125

Pro Ser  Ser Val Ser Ala Ser  Val Gly Asp Arg Val  Thr Ile Thr
    1130                 1135                 1140

Cys Gln  Ala Ser Gln Asn Ile  Arg Thr Tyr Leu Ser  Trp Tyr Gln
    1145                 1150                 1155

Gln Lys  Pro Gly Lys Ala Pro  Lys Leu Leu Ile Tyr  Ala Ala Ala
    1160                 1165                 1170

Asn Leu  Ala Ser Gly Val Pro  Ser Arg Phe Ser Gly  Ser Gly Ser
    1175                 1180                 1185

Gly Thr  Asp Phe Thr Leu Thr  Ile Ser Asp Leu Glu  Pro Gly Asp
    1190                 1195                 1200

Ala Ala  Thr Tyr Tyr Cys Gln  Ser Thr Tyr Leu Gly  Thr Asp Tyr
    1205                 1210                 1215

Val Gly  Gly Ala Phe Gly Gly  Gly Thr Lys Val Glu  Ile Lys
    1220                 1225                 1230
```

<210> SEQ ID NO 101
<211> LENGTH: 660
<212> TYPE: DNA
<213> ORGANISM: Artificial Sequence
<220> FEATURE:
<223> OTHER INFORMATION: Synthesized

<400> SEQUENCE: 101

```
gacatccaga tgacccagtc tccatcctcc ctgtctgcat ctgtaggaga cagagtcacc     60

atcacttgcc agtccagtca gagtgtttat aacaacaacg acttagcctg gtatcagcag    120

aaaccaggga aagttcctaa gctcctgatc tattatgcat ccactctggc atctggggtc    180

ccatctcggt tcagtggcag tggatctggg acagatttca ctctcaccat cagcagcctg    240

cagcctgaag atgttgcaac ttattactgt gcaggcggtt atgatacgga tggtcttgat    300

acgtttgctt tcggcggagg gaccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540
```

ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 102
<211> LENGTH: 220
<212> TYPE: PRT
<213> ORGANISM: Artificial Sequence
<220> FEATURE:
<223> OTHER INFORMATION: Synthesized

<400> SEQUENCE: 102

Asp Ile Gln Met Thr Gln Ser Pro Ser Ser Leu Ser Ala Ser Val Gly
1 5 10 15

Asp Arg Val Thr Ile Thr Cys Gln Ser Ser Gln Ser Val Tyr Asn Asn
20 25 30

Asn Asp Leu Ala Trp Tyr Gln Gln Lys Pro Gly Lys Val Pro Lys Leu
35 40 45

Leu Ile Tyr Tyr Ala Ser Thr Leu Ala Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Val Ala Thr Tyr Tyr Cys Ala Gly Gly Tyr Asp Thr
85 90 95

Asp Gly Leu Asp Thr Phe Ala Phe Gly Gly Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 103
<211> LENGTH: 3690
<212> TYPE: DNA
<213> ORGANISM: Artificial Sequence
<220> FEATURE:
<223> OTHER INFORMATION: Synthesized

<400> SEQUENCE: 103
gacgtcgtga tgacccagtc tccttccacc ctgtctgcat ctgtaggaga cagagtcacc 60
atcaattgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagag ttcactctca ccatcagcag cctgcagcct 240
gatgattttg caacttatta ctgccaaggc tatttttatt ttattagtcg tacttatgta 300
aattctttcg gcggagggac caaggtggag atcaaaggcg gtggcggtag tgggggaggc 360

-continued

```
ggttctggcg gcggagggtc cggcggtgga ggatcagagg tgcagctggt ggagtctggg    420
ggaggcttgg tccagcctgg ggggtccctg agactctcct gtgcagcctc tggattcacc    480
atcagtacca atgcaatgag ctgggtccgc caggctccag ggaaggggct ggagtggatc    540
ggagtcatta ctggtcgtga tatcacatac tacgcgagct gggcgaaagg cagattcacc    600
atctccagag acaattccaa gaacacgctg tatcttcaaa tgaacagcct gagagccgag    660
gacacggctg tgtattactg tgcgcgcgac ggtggatcat ctgctattac tagtaacaac    720
atttggggcc aaggaactct ggtcaccgtt tcttcaggcg gtggagggtc cggcggtggt    780
ggatccgagg tgcagctggt gcagtctgga gcagaggtga agaaaccagg agagtctctg    840
aagatctcct gtaagggttc tggatacagc tttagcagtt catggatcgg ctgggtgcgc    900
caggcacctg ggaaaggcct ggaatggatg gggatcatct atcctgatga ctctgatacc    960
agatacagtc catccttcca aggccaggtc accatctcag ccgacaagtc catcaggact   1020
gcctacctgc agtggagtag cctgaaggcc tcggacaccg ctatgtatta ctgtgcgaga   1080
catgttacta tgatttgggg agttattatt gacttctggg gccagggaac cctggtcacc   1140
gtctcctcag ctagcaccaa gggcccatcg gtcttccccc tggcaccctc ctccaagagc   1200
acctctgggg gcacagcggc cctgggctgc ctggtcaagg actacttccc cgaaccggtg   1260
acggtgtcgt ggaactcagg cgccctgacc agcggcgtgc acaccttccc ggctgtccta   1320
cagtcctcag gactctactc cctcagcagc gtggtgaccg tgccctccag cagcttgggc   1380
acccagacct acatctgcaa cgtgaatcac aagcccagca acaccaaggt ggacaagaga   1440
gttgagccca aatcttgtga caaaactcac acatgcccac cgtgcccagc acctgaagcc   1500
gcgggggcac cgtcagtctt cctcttcccc ccaaaaccca aggacaccct catgatctcc   1560
cggacccctg aggtcacatg cgtggtggtg gacgtgagcc acgaagaccc tgaggtcaag   1620
ttcaactggt acgtggacgg cgtggaggtg cataatgcca agacaaagcc gcgggaggag   1680
cagtacaaca gcacgtaccg tgtggtcagc gtcctcaccg tcctgcacca ggactggctg   1740
aatggcaagg agtacaagtg cgcggtctcc aacaaagccc tcccagcccc catcgagaaa   1800
accatctcca aagccaaagg gcagccccga gaaccacagg tgtataccct gcccccatcc   1860
cgggatgagc tgaccaagaa ccaggtcagc ctgacctgcc tggtcaaagg cttctatccc   1920
agcgacatcg ccgtggagtg ggagagcaat gggcagccgg agaacaacta caagaccacg   1980
cctcccgtgc tggactccga cggctccttc ttcctctata gcaagctcac cgtggacaag   2040
agcaggtggc agcaggggaa cgtcttctca tgctccgtga tgcatgaggc tctgcacaac   2100
cactacacgc agaagagcct ctccctgtct ccgggtggcg gtggagggtc cggcggtggt   2160
ggatccgagg tgcagctgtt ggagtctggg ggaggcttgg tacagcctgg ggggtccctg   2220
agactctcct gtgcagcctc tggattctcc ttcagtagcg ggtacgacat gtgctgggtc   2280
cgccaggctc cagggaaggg gctggagtgg atcgcatgca ttgctgctgg tagtgctggt   2340
atcacttacg acgcgaactg ggcgaaaggc cggttcacca tctccagaga caattccaag   2400
aacacgctgt atctgcaaat gaacagcctg agagccgagg acacggccgt atattactgt   2460
gcgagatcgg cgttttcgtt cgactacgcc atggacctct ggggccaggg aaccctggtc   2520
accgtctcga gcggtggagg cggatctggc ggaggtggtt ccggcggtgg cggctccggt   2580
ggaggcggct ctgacatcca gatgacccag tctccttcca ccctgtctgc atctgtagga   2640
gacagagtca ccatcacttg ccaggccagt cagagcatta gttcccactt aaactggtat   2700
cagcagaaac cagggaaagc ccctaagctc ctgatctata aggcatccac tctggcatct   2760
```

```
ggggtcccat caaggttcag cggcagtgga tctgggacag aatttactct caccatcagc   2820
agcctgcagc ctgatgattt tgcaacttat tactgccaac agggttatag ttggggtaat   2880
gttgataatg ttttcggcgg agggaccaag gtggagatca aaggcggtgg agggtccggc   2940
ggtggtggat cccggtcgct ggtggagtct gggggaggct tggtccagcc tggggggtcc   3000
ctgagactct cctgtacagc ctctggattc accatcagta gctaccacat gcagtgggtc   3060
cgccaggctc cagggaaggg gctggagtac atcggaacca ttagtagtgg tggtaatgta   3120
tactacgcga gctccgcgag aggcagattc accatctcca gaccctcgtc caagaacacg   3180
gtggatcttc aaatgaacag cctgagagcc gaggacacgg ctgtgtatta ctgtgcgaga   3240
gactctggtt atagtgatcc tatgtggggc cagggaaccc tggtcaccgt ctcgagcggc   3300
ggtggcggta gtgggggagg cggttctggc ggcggagggt ccggcggtgg aggatcagac   3360
gttgtgatga cccagtctcc atcttccgtg tctgcatctg taggagacag agtcaccatc   3420
acctgtcagg ccagtcagaa cattaggact tacttatcct ggtatcagca gaaaccaggg   3480
aaagccccta agctcctgat ctatgctgca gccaatctgg catctggggt cccatcaagg   3540
ttcagcggca gtggatctgg gacagatttc actctcacca tcagcgacct ggagcctggc   3600
gatgctgcaa cttactattg tcagtctacc tatcttggta ctgattatgt tggcggtgct   3660
ttcggcggag ggaccaaggt ggagatcaaa                                    3690
```

<210> SEQ ID NO 104
<211> LENGTH: 1230
<212> TYPE: PRT
<213> ORGANISM: Artificial Sequence
<220> FEATURE:
<223> OTHER INFORMATION: Synthesized

<400> SEQUENCE: 104

```
Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Ile Ser Thr Asn Ala Met Ser Trp Val Arg Gln Ala Pro Gly Lys Gly
                165                 170                 175

Leu Glu Trp Ile Gly Val Ile Thr Gly Arg Asp Ile Thr Tyr Tyr Ala
            180                 185                 190
```

```
Ser Trp Ala Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Gly Gly Ser Ser Ala Ile Thr Ser Asn Asn
225                 230                 235                 240

Ile Trp Gly Gln Gly Thr Leu Val Thr Val Ser Ser Gly Gly Gly Gly
                245                 250                 255

Ser Gly Gly Gly Gly Ser Glu Val Gln Leu Val Gln Ser Gly Ala Glu
            260                 265                 270

Val Lys Lys Pro Gly Glu Ser Leu Lys Ile Ser Cys Lys Gly Ser Gly
        275                 280                 285

Tyr Ser Phe Ser Ser Ser Trp Ile Gly Trp Val Arg Gln Ala Pro Gly
    290                 295                 300

Lys Gly Leu Glu Trp Met Gly Ile Ile Tyr Pro Asp Asp Ser Asp Thr
305                 310                 315                 320

Arg Tyr Ser Pro Ser Phe Gln Gly Gln Val Thr Ile Ser Ala Asp Lys
                325                 330                 335

Ser Ile Arg Thr Ala Tyr Leu Gln Trp Ser Ser Leu Lys Ala Ser Asp
            340                 345                 350

Thr Ala Met Tyr Tyr Cys Ala Arg His Val Thr Met Ile Trp Gly Val
        355                 360                 365

Ile Ile Asp Phe Trp Gly Gln Gly Thr Leu Val Thr Val Ser Ser Ala
    370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
        435                 440                 445

Ser Ser Val Val Thr Val Pro Ser Ser Ser Leu Gly Thr Gln Thr Tyr
    450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Ala Ala Gly Ala Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Ala Val Ser Asn Lys
            580                 585                 590

Ala Leu Pro Ala Pro Ile Glu Lys Thr Ile Ser Lys Ala Lys Gly Gln
        595                 600                 605

Pro Arg Glu Pro Gln Val Tyr Thr Leu Pro Pro Ser Arg Asp Glu Leu
```

```
    610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly Gly Gly Gly Gly Ser Gly Gly Gly
705                 710                 715                 720

Gly Ser Glu Val Gln Leu Leu Glu Ser Gly Gly Gly Leu Val Gln Pro
                725                 730                 735

Gly Gly Ser Leu Arg Leu Ser Cys Ala Ala Ser Gly Phe Ser Phe Ser
            740                 745                 750

Ser Gly Tyr Asp Met Cys Trp Val Arg Gln Ala Pro Gly Lys Gly Leu
        755                 760                 765

Glu Trp Ile Ala Cys Ile Ala Ala Gly Ser Ala Gly Ile Thr Tyr Asp
    770                 775                 780

Ala Asn Trp Ala Lys Gly Arg Phe Thr Ile Ser Arg Asp Asn Ser Lys
785                 790                 795                 800

Asn Thr Leu Tyr Leu Gln Met Asn Ser Leu Arg Ala Glu Asp Thr Ala
                805                 810                 815

Val Tyr Tyr Cys Ala Arg Ser Ala Phe Ser Phe Asp Tyr Ala Met Asp
            820                 825                 830

Leu Trp Gly Gln Gly Thr Leu Val Thr Val Ser Ser Gly Gly Gly Gly
        835                 840                 845

Ser Gly Gly Gly Gly Ser Gly Gly Gly Gly Ser Gly Gly Gly Gly Ser
    850                 855                 860

Asp Ile Gln Met Thr Gln Ser Pro Ser Thr Leu Ser Ala Ser Val Gly
865                 870                 875                 880

Asp Arg Val Thr Ile Thr Cys Gln Ala Ser Gln Ser Ile Ser Ser His
                885                 890                 895

Leu Asn Trp Tyr Gln Gln Lys Pro Gly Lys Ala Pro Lys Leu Leu Ile
            900                 905                 910

Tyr Lys Ala Ser Thr Leu Ala Ser Gly Val Pro Ser Arg Phe Ser Gly
        915                 920                 925

Ser Gly Ser Gly Thr Glu Phe Thr Leu Thr Ile Ser Ser Leu Gln Pro
    930                 935                 940

Asp Asp Phe Ala Thr Tyr Tyr Cys Gln Gln Gly Tyr Ser Trp Gly Asn
945                 950                 955                 960

Val Asp Asn Val Phe Gly Gly Gly Thr Lys Val Glu Ile Lys Gly Gly
                965                 970                 975

Gly Gly Ser Gly Gly Gly Gly Ser Arg Ser Leu Val Glu Ser Gly Gly
            980                 985                 990

Gly Leu Val Gln Pro Gly Gly Ser  Leu Arg Leu Ser Cys  Thr Ala Ser
        995                 1000                1005

Gly Phe  Thr Ile Ser Ser Tyr  His Met Gln Trp Val  Arg Gln Ala
    1010                1015                1020

Pro Gly  Lys Gly Leu Glu Tyr  Ile Gly Thr Ile Ser  Ser Gly Gly
    1025                1030                1035
```

```
Asn Val  Tyr Tyr Ala Ser Ser  Ala Arg Gly Arg Phe  Thr Ile Ser
    1040                 1045                 1050

Arg Pro  Ser Ser Lys Asn Thr  Val Asp Leu Gln Met  Asn Ser Leu
    1055                 1060                 1065

Arg Ala  Glu Asp Thr Ala Val  Tyr Tyr Cys Ala Arg  Asp Ser Gly
    1070                 1075                 1080

Tyr Ser  Asp Pro Met Trp Gly  Gln Gly Thr Leu Val  Thr Val Ser
    1085                 1090                 1095

Ser Gly  Gly Gly Gly Ser Gly  Gly Gly Gly Ser Gly  Gly Gly Gly
    1100                 1105                 1110

Ser Gly  Gly Gly Gly Ser Asp  Val Val Met Thr Gln  Ser Pro Ser
    1115                 1120                 1125

Ser Val  Ser Ala Ser Val Gly  Asp Arg Val Thr Ile  Thr Cys Gln
    1130                 1135                 1140

Ala Ser  Gln Asn Ile Arg Thr  Tyr Leu Ser Trp Tyr  Gln Gln Lys
    1145                 1150                 1155

Pro Gly  Lys Ala Pro Lys Leu  Leu Ile Tyr Ala Ala  Ala Asn Leu
    1160                 1165                 1170

Ala Ser  Gly Val Pro Ser Arg  Phe Ser Gly Ser Gly  Ser Gly Thr
    1175                 1180                 1185

Asp Phe  Thr Leu Thr Ile Ser  Asp Leu Glu Pro Gly  Asp Ala Ala
    1190                 1195                 1200

Thr Tyr  Tyr Cys Gln Ser Thr  Tyr Leu Gly Thr Asp  Tyr Val Gly
    1205                 1210                 1215

Gly Ala  Phe Gly Gly Gly Thr  Lys Val Glu Ile Lys
    1220                 1225                 1230
```

<210> SEQ ID NO 105
<211> LENGTH: 642
<212> TYPE: DNA
<213> ORGANISM: Artificial Sequence
<220> FEATURE:
<223> OTHER INFORMATION: Synthesized

<400> SEQUENCE: 105

```
gccatccagt tgacccagtc tccatcctcc ctgtctgcat ctgtaggaga cagagtcacc     60

atcacttgcc gggcaagtca gggcattagc agtgctttag cctggtatca gcagaaacca    120

gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt acccattcac tttcggccct    300

gggaccaaag tggatatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 106
<211> LENGTH: 214
<212> TYPE: PRT
<213> ORGANISM: Artificial Sequence
<220> FEATURE:
<223> OTHER INFORMATION: Synthesized

<400> SEQUENCE: 106

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Phe
85 90 95

Thr Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 107
<211> LENGTH: 3675
<212> TYPE: DNA
<213> ORGANISM: Artificial Sequence
<220> FEATURE:
<223> OTHER INFORMATION: Synthesized

<400> SEQUENCE: 107
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccattcac tttcggccct 300
gggaccaaag tggatatcaa aggcggtggc ggtagtgggg gaggcggttc tggcggcgga 360
gggtccggcg gtggaggatc agaggtgcag ctggtgcagt ctggagcaga ggtgaagaaa 420
ccaggagagt ctctgaagat ctcctgtaag ggttctggat acagctttag cagttcatgg 480
atcggctggg tgcgccaggc acctgggaaa ggcctggaat ggatggggat catctatcct 540
gatgactctg ataccagata cagtccatcc ttccaaggcc aggtcaccat ctcagccgac 600
aagtccatca ggactgccta cctgcagtgg agtagcctga aggcctcgga caccgctatg 660
tattactgtg cgagacatgt tactatgatt tggggagtta ttattgactt ctggggccag 720

-continued

```
ggaaccctgg tcaccgtctc ctcaggcggt ggagggtccg gcggtggtgg atccgaggtg    780
cagctggtgg agtctggggg aggcttggtc cagcctgggg ggtccctgag actctcctgt    840
gcagcctctg gattcaccat cagtaccaat gcaatgagct gggtccgcca ggctccaggg    900
aaggggctgg agtggatcgg agtcattact ggtcgtgata tcacatacta cgcgagctgg    960
gcgaaaggca gattcaccat ctccagagac aattccaaga acacgctgta tcttcaaatg   1020
aacagcctga gagccgagga cacggctgtg tattactgtg cgcgcgacgg tggatcatct   1080
gctattacta gtaacaacat ttggggccaa ggaactctgg tcaccgtttc ttcagctagc   1140
accaagggcc catcggtctt ccccctggca ccctcctcca agagcacctc tgggggcaca   1200
gcggccctgg gctgcctggt caaggactac ttccccgaac cggtgacggt gtcgtggaac   1260
tcaggcgccc tgaccagcgg cgtgcacacc ttcccggctg tcctacagtc ctcaggactc   1320
tactccctca gcagcgtggt gaccgtgccc tccagcagct tgggcaccca gacctacatc   1380
tgcaacgtga atcacaagcc cagcaacacc aaggtggaca agagagttga gcccaaatct   1440
tgtgacaaaa ctcacacatg cccaccgtgc ccagcacctg aagccgcggg ggcaccgtca   1500
gtcttcctct tccccccaaa acccaaggac accctcatga tctcccggac ccctgaggtc   1560
acatgcgtgg tggtggacgt gagccacgaa gaccctgagg tcaagttcaa ctggtacgtg   1620
gacggcgtgg aggtgcataa tgccaagaca aagccgcggg aggagcagta caacagcacg   1680
taccgtgtgg tcagcgtcct caccgtcctg caccaggact ggctgaatgg caaggagtac   1740
aagtgcgcgg tctccaacaa agccctccca gcccccatcg agaaaaccat ctccaaagcc   1800
aaagggcagc cccgagaacc acaggtgtat accctgcccc catcccggga tgagctgacc   1860
aagaaccagg tcagcctgac ctgcctggtc aaaggcttct atcccagcga catcgccgtg   1920
gagtgggaga gcaatgggca gccggagaac aactacaaga ccacgcctcc cgtgctggac   1980
tccgacggct ccttcttcct ctatagcaag ctcaccgtgg acaagagcag gtggcagcag   2040
gggaacgtct tctcatgctc cgtgatgcat gaggctctgc acaaccacta cacgcagaag   2100
agcctctccc tgtctccggg tggcggtgga gggtccggcg gtggtggatc cgaggtgcag   2160
ctgttggagt ctgggggagg cttggtacag cctggggggt ccctgagact ctcctgtgca   2220
gcctctggat tctccttcag tagcgggtac gacatgtgct gggtccgcca ggctccaggg   2280
aaggggctgg agtggatcgc atgcattgct gctggtagtg ctggtatcac ttacgacgcg   2340
aactgggcga aaggccggtt caccatctcc agagacaatt ccaagaacac gctgtatctg   2400
caaatgaaca gcctgagagc cgaggacacg gccgtatatt actgtgcgag atcggcgttt   2460
tcgttcgact acgccatgga cctctggggc cagggaaccc tggtcaccgt ctcgagcggt   2520
ggaggcggat ctggcggagg tggttccggc ggtggcggct ccggtggagg cggctctgac   2580
atccagatga cccagtctcc ttccaccctg tctgcatctg taggagacag agtcaccatc   2640
acttgccagg ccagtcagag cattagttcc cacttaaact ggtatcagca gaaaccaggg   2700
aaagccccta agctcctgat ctataaggca tccactctgg catctggggt cccatcaagg   2760
ttcagcggca gtggatctgg gacagaattt actctcacca tcagcagcct gcagcctgat   2820
gattttgcaa cttattactg ccaacagggt tatagttggg gtaatgttga taatgttttc   2880
ggcggaggga ccaaggtgga gatcaaaggc ggtggagggt ccggcggtgg tggatcccgg   2940
tcgctggtgg agtctggggg aggcttggtc cagcctgggg ggtccctgag actctcctgt   3000
acagcctctg gattcaccat cagtagctac cacatgcagt gggtccgcca ggctccaggg   3060
aaggggctgg agtacatcgg aaccattagt agtggtggta atgtatacta cgcgagctcc   3120
```

```
gcgagaggca gattcaccat ctccagaccc tcgtccaaga acacggtgga tcttcaaatg   3180

aacagcctga gagccgagga cacggctgtg tattactgtg cgagagactc tggttatagt   3240

gatcctatgt ggggccaggg aaccctggtc accgtctcga gcggcggtgg cggtagtggg   3300

ggaggcggtt ctggcggcgg agggtccggc ggtggaggat cagacgttgt gatgacccag   3360

tctccatctt ccgtgtctgc atctgtagga gacagagtca ccatcacctg tcaggccagt   3420

cagaacatta ggacttactt atcctggtat cagcagaaac cagggaaagc ccctaagctc   3480

ctgatctatg ctgcagccaa tctggcatct ggggtcccat caaggttcag cggcagtgga   3540

tctgggacag atttcactct caccatcagc gacctggagc ctggcgatgc tgcaacttac   3600

tattgtcagt ctacctatct tggtactgat tatgttggcg gtgctttcgg cggagggacc   3660

aaggtggaga tcaaa                                                    3675


<210> SEQ ID NO 108
<211> LENGTH: 1225
<212> TYPE: PRT
<213> ORGANISM: Artificial Sequence
<220> FEATURE:
<223> OTHER INFORMATION: Synthesized

<400> SEQUENCE: 108

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Ser Ser Ser Trp
145                 150                 155                 160

Ile Gly Trp Val Arg Gln Ala Pro Gly Lys Gly Leu Glu Trp Met Gly
                165                 170                 175

Ile Ile Tyr Pro Asp Asp Ser Asp Thr Arg Tyr Ser Pro Ser Phe Gln
            180                 185                 190

Gly Gln Val Thr Ile Ser Ala Asp Lys Ser Ile Arg Thr Ala Tyr Leu
        195                 200                 205

Gln Trp Ser Ser Leu Lys Ala Ser Asp Thr Ala Met Tyr Tyr Cys Ala
    210                 215                 220

Arg His Val Thr Met Ile Trp Gly Val Ile Ile Asp Phe Trp Gly Gln
225                 230                 235                 240

Gly Thr Leu Val Thr Val Ser Ser Gly Gly Gly Gly Ser Gly Gly Gly
                245                 250                 255
```

```
Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Thr Ile Ser
        275                 280                 285

Thr Asn Ala Met Ser Trp Val Arg Gln Ala Pro Gly Lys Gly Leu Glu
    290                 295                 300

Trp Ile Gly Val Ile Thr Gly Arg Asp Ile Thr Tyr Tyr Ala Ser Trp
305                 310                 315                 320

Ala Lys Gly Arg Phe Thr Ile Ser Arg Asp Asn Ser Lys Asn Thr Leu
                325                 330                 335

Tyr Leu Gln Met Asn Ser Leu Arg Ala Glu Asp Thr Ala Val Tyr Tyr
            340                 345                 350

Cys Ala Arg Asp Gly Gly Ser Ser Ala Ile Thr Ser Asn Asn Ile Trp
        355                 360                 365

Gly Gln Gly Thr Leu Val Thr Val Ser Ser Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Gln Thr Tyr Ile Cys Asn Val Asn
    450                 455                 460

His Lys Pro Ser Asn Thr Lys Val Asp Lys Arg Val Glu Pro Lys Ser
465                 470                 475                 480

Cys Asp Lys Thr His Thr Cys Pro Pro Cys Pro Ala Pro Glu Ala Ala
                485                 490                 495

Gly Ala Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Ala Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
```

```
        675                 680                 685

Met His Glu Ala Leu His Asn His Tyr Thr Gln Lys Ser Leu Ser Leu
    690                 695                 700

Ser Pro Gly Gly Gly Gly Gly Ser Gly Gly Gly Gly Ser Glu Val Gln
705                 710                 715                 720

Leu Leu Glu Ser Gly Gly Gly Leu Val Gln Pro Gly Gly Ser Leu Arg
                725                 730                 735

Leu Ser Cys Ala Ala Ser Gly Phe Ser Phe Ser Ser Gly Tyr Asp Met
            740                 745                 750

Cys Trp Val Arg Gln Ala Pro Gly Lys Gly Leu Glu Trp Ile Ala Cys
        755                 760                 765

Ile Ala Ala Gly Ser Ala Gly Ile Thr Tyr Asp Ala Asn Trp Ala Lys
    770                 775                 780

Gly Arg Phe Thr Ile Ser Arg Asp Asn Ser Lys Asn Thr Leu Tyr Leu
785                 790                 795                 800

Gln Met Asn Ser Leu Arg Ala Glu Asp Thr Ala Val Tyr Tyr Cys Ala
                805                 810                 815

Arg Ser Ala Phe Ser Phe Asp Tyr Ala Met Asp Leu Trp Gly Gln Gly
            820                 825                 830

Thr Leu Val Thr Val Ser Ser Gly Gly Gly Gly Ser Gly Gly Gly Gly
        835                 840                 845

Ser Gly Gly Gly Gly Ser Gly Gly Gly Gly Ser Asp Ile Gln Met Thr
    850                 855                 860

Gln Ser Pro Ser Thr Leu Ser Ala Ser Val Gly Asp Arg Val Thr Ile
865                 870                 875                 880

Thr Cys Gln Ala Ser Gln Ser Ile Ser Ser His Leu Asn Trp Tyr Gln
                885                 890                 895

Gln Lys Pro Gly Lys Ala Pro Lys Leu Leu Ile Tyr Lys Ala Ser Thr
            900                 905                 910

Leu Ala Ser Gly Val Pro Ser Arg Phe Ser Gly Ser Gly Ser Gly Thr
        915                 920                 925

Glu Phe Thr Leu Thr Ile Ser Ser Leu Gln Pro Asp Asp Phe Ala Thr
    930                 935                 940

Tyr Tyr Cys Gln Gln Gly Tyr Ser Trp Gly Asn Val Asp Asn Val Phe
945                 950                 955                 960

Gly Gly Gly Thr Lys Val Glu Ile Lys Gly Gly Gly Gly Ser Gly Gly
                965                 970                 975

Gly Gly Ser Arg Ser Leu Val Glu Ser Gly Gly Gly Leu Val Gln Pro
            980                 985                 990

Gly Gly Ser Leu Arg Leu Ser Cys  Thr Ala Ser Gly Phe  Thr Ile Ser
        995                 1000                1005

Ser Tyr  His Met Gln Trp Val  Arg Gln Ala Pro Gly  Lys Gly Leu
    1010                1015                1020

Glu Tyr  Ile Gly Thr Ile Ser  Ser Gly Gly Asn Val  Tyr Tyr Ala
    1025                1030                1035

Ser Ser  Ala Arg Gly Arg Phe  Thr Ile Ser Arg Pro  Ser Ser Lys
    1040                1045                1050

Asn Thr  Val Asp Leu Gln Met  Asn Ser Leu Arg Ala  Glu Asp Thr
    1055                1060                1065

Ala Val  Tyr Tyr Cys Ala Arg  Asp Ser Gly Tyr Ser  Asp Pro Met
    1070                1075                1080

Trp Gly  Gln Gly Thr Leu Val  Thr Val Ser Ser Gly  Gly Gly Gly
    1085                1090                1095
```

```
Ser Gly Gly Gly Gly Ser Gly Gly Gly Gly Ser Gly Gly Gly Gly
    1100                1105                1110

Ser Asp Val Val Met Thr Gln Ser Pro Ser Ser Val Ser Ala Ser
    1115                1120                1125

Val Gly Asp Arg Val Thr Ile Thr Cys Gln Ala Ser Gln Asn Ile
    1130                1135                1140

Arg Thr Tyr Leu Ser Trp Tyr Gln Gln Lys Pro Gly Lys Ala Pro
    1145                1150                1155

Lys Leu Leu Ile Tyr Ala Ala Ala Asn Leu Ala Ser Gly Val Pro
    1160                1165                1170

Ser Arg Phe Ser Gly Ser Gly Ser Gly Thr Asp Phe Thr Leu Thr
    1175                1180                1185

Ile Ser Asp Leu Glu Pro Gly Asp Ala Ala Thr Tyr Tyr Cys Gln
    1190                1195                1200

Ser Thr Tyr Leu Gly Thr Asp Tyr Val Gly Gly Ala Phe Gly Gly
    1205                1210                1215

Gly Thr Lys Val Glu Ile Lys
    1220                1225
```

<210> SEQ ID NO 109
<211> LENGTH: 657
<212> TYPE: DNA
<213> ORGANISM: Artificial Sequence
<220> FEATURE:
<223> OTHER INFORMATION: Synthesized

<400> SEQUENCE: 109

```
gacgtcgtga tgacccagtc tccttccacc ctgtctgcat ctgtaggaga cagagtcacc     60

atcaattgcc aagccagtga gagcattagc agttggttag cctggtatca gcagaaacca    120

gggaaagccc ctaagctcct gatctatgaa gcatccaaac tggcatctgg ggtcccatca    180

aggttcagcg gcagtggatc tgggacagaa ttcactctca ccatcagcag cctgcagcct    240

gatgattttg caacttatta ctgccaaggc tatttttatt ttattagtcg tacttatgta    300

aattctttcg gcggagggac caaggtggag atcaaacgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 110
<211> LENGTH: 219
<212> TYPE: PRT
<213> ORGANISM: Artificial Sequence
<220> FEATURE:
<223> OTHER INFORMATION: Synthesized

<400> SEQUENCE: 110

```
Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45
```

-continued

```
Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```